US012573494B1

(12) United States Patent

Coelho et al.

(10) Patent No.: US 12,573,494 B1
(45) Date of Patent: Mar. 10, 2026

(54) MULTI-DIMENSIONAL REINFORCEMENT LEARNING IN AN AI PLATFORM

(71) Applicant: Sword Health, S.A., Oporto (PT)

(72) Inventors: Luís Ungaro Pinto Coelho, Oporto (PT); Ana Clara Ferreira Matos, Oporto (PT); Filipe Daniel Martins Rodrigues, Oporto (PT); Virgílio António Ferro Bento, Oporto (PT); Ivo Emanuel Marques Gabriel, Oporto (PT); Pedro Henrique Oliveira Santos, Oporto (PT); Fabíola Maria Tavares Alves da Costa Moutinho, Oporto (PT); Fernando Emanuel Dias Correia, Oporto (PT)

(73) Assignee: SWORD HEALTH, S.A., Oporto (PT)

( * ) Notice: Subject to any disclaimer, the term of this patent is extended or adjusted under 35 U.S.C. 154(b) by 0 days.

(21) Appl. No.: 19/223,888

(22) Filed: May 30, 2025

(51) Int. Cl.
*G16H 20/30* (2018.01)
*G16H 50/20* (2018.01)

(52) U.S. Cl.
CPC ............. *G16H 20/30* (2018.01); *G16H 50/20* (2018.01)

(58) Field of Classification Search
CPC ............................... G16H 20/30; G16H 50/20
USPC ......................................................... 705/2–3
See application file for complete search history.

(56) References Cited

U.S. PATENT DOCUMENTS 9,898,789 B2 2/2018 Ram et al.
10,130,311 B1 11/2018 De Sapio et al.

10,413,238 B1 9/2019 Cooper et al.
11,039,763 B2 6/2021 Ye et al.
12,397,198 B1 8/2025 Bento et al.
2007/0179816 A1 8/2007 Lemme
(Continued)

FOREIGN PATENT DOCUMENTS

CN 115023763 9/2022
WO 2015103442 7/2015
(Continued)

OTHER PUBLICATIONS

Alowais et al. Revolutionizing healthcare: the role of artificial intelligence in clinical practice. BMC Med Educ. 2023;23(1):689. Published Sep. 2, 20232. doi: 10.1186/s12909-023-04698-z (Year: 2023).*

(Continued)

*Primary Examiner* — Joy Chng
(74) *Attorney, Agent, or Firm* — SCHWEGMAN LUNDBERG & WOESSNER, P.A.

(57) ABSTRACT

Examples in the present disclosure relate to multi-dimensional reinforcement learning in a digital platform. The digital platform maintains and updates user data associated with tracked users. One or more machine learning models process the user data to generate recommendation data that includes automatically generated exploratory program elements for known activity programs of respective users of the digital platform. The exploratory program elements are validated by supervising users before implementation. The digital platform continuously updates the one or more machine learning models using dual reinforcement signals: one based on supervising user-validated recommendations and another based on activity program results. Further recommendation data is generated after updating the one or more machine learning models.

20 Claims, 19 Drawing Sheets

(56) References Cited

U.S. PATENT DOCUMENTS

| | | | |
|---|---|---|---|
| 2012/0290319 A1 | 11/2012 | Saria et al. | |
| 2015/0038806 A1 | 2/2015 | Kaleal, III et al. | |
| 2015/0324532 A1 | 11/2015 | Jones et al. | |
| 2018/0330810 A1* | 11/2018 | Gamarnik | G16H 10/20 |
| 2019/0328322 A1 | 10/2019 | Inada | |
| 2020/0066390 A1 | 2/2020 | Svendrys et al. | |
| 2020/0114207 A1 | 4/2020 | Weldemariam et al. | |
| 2021/0202103 A1 | 7/2021 | Bostic et al. | |
| 2022/0016484 A1 | 1/2022 | Bissonnette et al. | |
| 2022/0076666 A1 | 3/2022 | Trehan | |
| 2022/0208385 A1 | 6/2022 | Voschina et al. | |
| 2022/0246268 A1 | 8/2022 | Hunter et al. | |
| 2022/0392611 A1* | 12/2022 | Appelbaum | G16H 50/20 |
| 2023/0071274 A1 | 3/2023 | Trehan | |
| 2025/0273351 A1 | 8/2025 | Matos et al. | |

FOREIGN PATENT DOCUMENTS

| | | |
|---|---|---|
| WO | 2019010435 | 1/2019 |
| WO | 2020198065 | 10/2020 |
| WO | WO-2022086454 A1 | 4/2022 |

OTHER PUBLICATIONS

Mosqueira-Rey et al. Human-in-the-loop machine learning: a state of the art. Artificial Intelligence Review 56, 3005-3054 (2023). https://doi.org/10.1007/s10462-022-10246-w (Year: 2023).*

Mukherjee, Subhabrata, et al., "Polaris A Safety focused LLM Constellation Architecture for Healthcare", arXiv:2403.13313v1 [cs.AI] Mar. 20, 2024, (Mar. 20, 2024), 53 pages.

Oberst, Michael, et al., "Pioneering the Science of AI Evaluation", [Online]. Retrieved from the Internet: <https://www.abridge.com/ai/science-ai-evaluation>, (Accessed online May 21, 2025), 25 pages.

"U.S. Appl. No. 18/585,380, Non Final Office Action mailed Apr. 22, 2024", 25 pgs.

"U.S. Appl. No. 18/585,380, Response filed Jul. 22, 2024 to Non Final Office Action mailed Apr. 22, 2024", 19 pgs.

"U.S. Appl. No. 18/585,380, Examiner Interview Summary mailed Jul. 26, 2024", 2 pgs.

"U.S. Appl. No. 18/585,355, Non Final Office Action mailed Jul. 30, 2024", 20 pgs.

"U.S. Appl. No. 18/585,380, Final Office Action mailed Aug. 9, 2024", 23 pgs.

"U.S. Appl. No. 18/585,380, Response filed Sep. 30, 2024 to Final Office Action mailed Aug. 9, 2024", 15 pgs.

"U.S. Appl. No. 18/585,380, Advisory Action mailed Oct. 9, 2024", 3 pgs.

"U.S. Appl. No. 18/585,355, Response filed Oct. 29, 2024 to Non Final Office Action mailed Jul. 30, 2024", 15 pgs.

"U.S. Appl. No. 18/585,380, Response filed Nov. 8, 2024 to Advisory Action mailed Oct. 9, 2024", 17 pgs.

"U.S. Appl. No. 18/585,355, Final Office Action mailed Dec. 2, 2024", 18 pgs.

"U.S. Appl. No. 18/585,380, Non Final Office Action mailed Jan. 29, 2025", 20 pgs.

"U.S. Appl. No. 18/585,355, Response filed Jan. 31, 2025 to Final Office Action mailed Dec. 2, 2024", 17 pgs.

"U.S. Appl. No. 18/585,355, Advisory Action mailed Feb. 11, 2025", 3 pgs.

"U.S. Appl. No. 18/585,355, Notice of Allowance mailed Mar. 19, 2025", 7 pgs.

"U.S. Appl. No. 18/585,380, Response filed Apr. 24, 2025 to Non Final Office Action mailed Jan. 29, 2025", 14 pgs.

"U.S. Appl. No. 18/585,380, Final Office Action mailed May 23, 2025", 19 pgs.

U.S. Appl. No. 18/585,380, Examiner Interview Summary mailed Jul. 1, 2025, 2 pages.

U.S. Appl. No. 18/585,380, Notice of Allowance mailed Aug. 4, 2025, 13 pgs.

U.S. Appl. No. 18/585,380, Response filed Jul. 17, 2025 to Final Office Action mailed May 23, 2025, 13 pgs.

Kalakoti, Yogesh, et al., "TransDTI: Transformer-Based Language Models for Estimating DTIs and Building a Drug Recommendation Workflow", ACS Publications; ACS Omega, 2706-2717, (2022), 12 pgs.

* cited by examiner

MULTI-DIMENSIONAL REINFORCEMENT LEARNING IN AN AI PLATFORM

TECHNICAL FIELD

Subject matter in the present disclosure generally relates to digital care technology. The subject matter includes, but is not limited to, artificial intelligence (AI) and machine learning techniques for improving the performance of a digital platform, such as a digital care platform.

BACKGROUND

The field of digital care, also referred to as digital therapy, encompasses a range of activities and treatments provided via digital means. The field has seen advancements in recent years, particularly with the integration of technology such as motion sensors and computer vision to assist users in remotely performing exercises or other activities. For example, a user of a digital care platform can perform activities assigned by the digital care program at home or in other convenient settings, with the digital care platform implementing technology to monitor sessions and provide remote support.

BRIEF DESCRIPTION OF THE SEVERAL VIEWS OF THE DRAWINGS

In the drawings, which are not necessarily drawn to scale, like numerals may describe similar components in different views. To easily identify the discussion of any particular element or act, the most significant digit or digits in a reference number refer to the figure number in which that element is first introduced. Some non-limiting examples are illustrated in the figures of the accompanying drawings in which.

DETAILED DESCRIPTION

Figure 1:
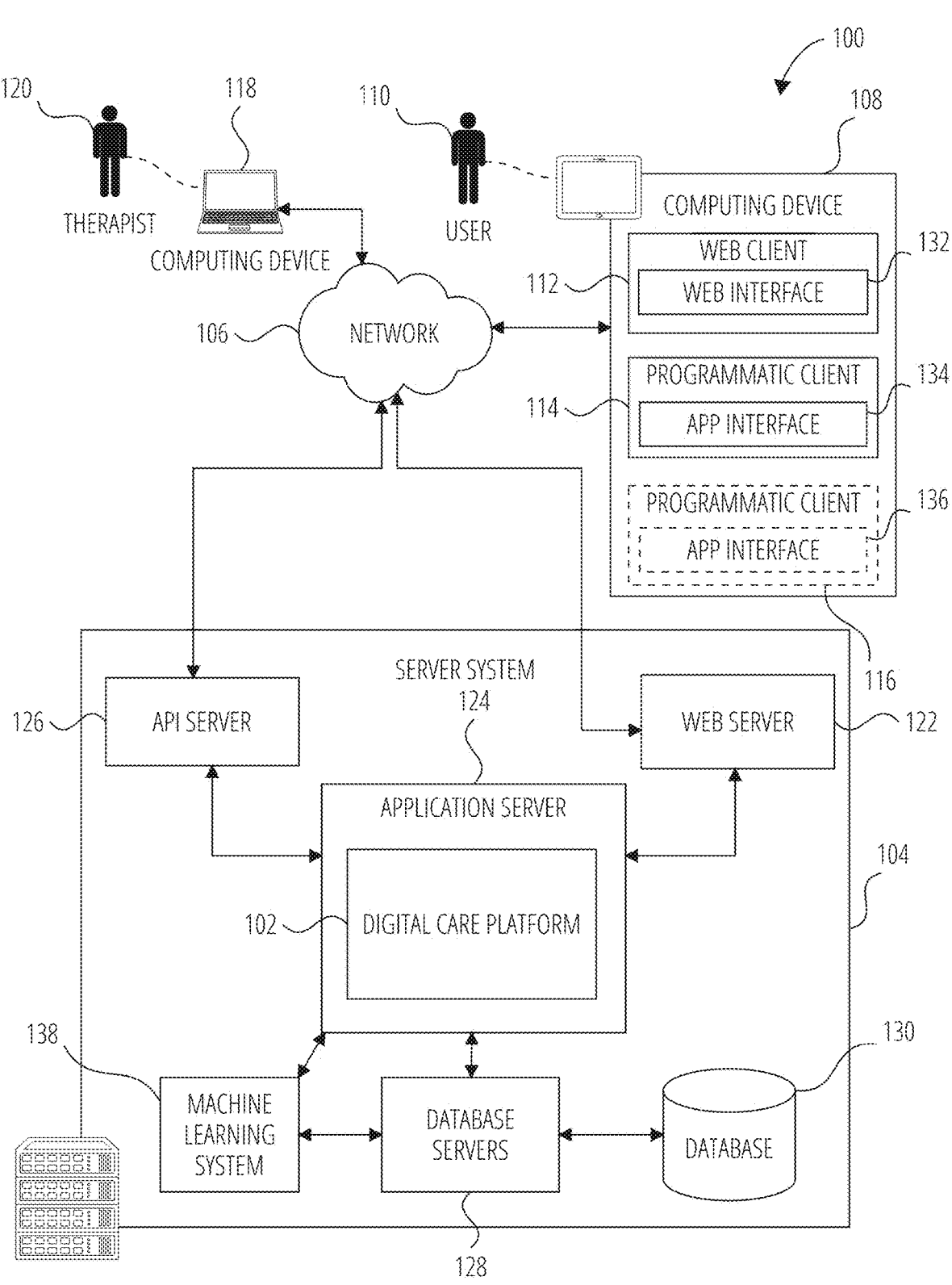
FIG. 1 is a diagrammatic illustration of a networked computing environment that includes a digital care platform, according to some examples.

Examples in the present disclosure address technical challenges related to providing effective and personalized digital care. In some examples, a three-layer technical architecture is provided, including an observation system, a reasoning system, and a communication system. The observation system captures and processes user data (e.g., using specialized hardware), the reasoning system automatically analyzes the data through specialized machine learning models to generate activity program elements, and the communication system delivers feedback. A digital care platform may process session data, behavioral data, and conversation data through coordinated components that feed into the reasoning system to generate user-specific recommendations. Recommendations can be validated using a human-in-the-loop framework, and a continuous learning cycle, in which validated recommendations and activity results are used to automatically modify machine learning model parameters, may be implemented.

Conventional healthcare systems often operate in a static manner, even where AI-based technologies are utilized. For example, a healthcare system may leverage a machine learning model that is trained on historical patient data. Systems of this nature may be able to replicate previously observed patterns, but may lack the technical capabilities to generate effective new therapeutic approaches and dynamically adapt based on patient results. This creates a technical constraint where a system's capabilities are bounded by initial or known data, limiting its ability to adapt to new user needs, identify potentially better treatment patterns, or properly account for individual variations.

Examples in the present disclosure address or alleviate technical constraints by implementing a dual-input reinforcement learning architecture. In some examples, the digital care platform continuously updates one or more machine learning models using multiple reinforcement signals, such as signals derived from both clinician validation of AI-generated recommendations and measured treatment outcomes. This technical approach may enable the digital care platform to safely explore beyond initial training data or known patterns by generating exploratory program elements (e.g., new activities, variations, or sequences) that are validated by supervising users before implementation. As such, a digital care platform can evolve beyond simply replicating historical decisions to progressively provide more personalized or effective care.

The present disclosure uses the terms "digital care," "digital care platform," and "session." As used herein, the term "digital care" may include a broad spectrum of health and wellness therapies, interventions, plans, programs, or activities delivered at least partially through digital means. Digital care may be aimed at addressing or diagnosing specific conditions and/or aimed at promoting physical fitness or well-being and/or aimed at preventative care. Accordingly, digital care may include targeted therapeutic plans, such as those for musculoskeletal (MSK) rehabilitation or pelvic-floor therapy, but may also include more general activities that are not necessarily linked to a specific therapeutic condition, such as general fitness-related exercises, strength exercises, or injury prevention, as well as mindfulness activities such as guided meditation or breathing. Digital care programs may be personalized and/or interactive, where activities are tailored to an individual's health objectives, whether for specific therapeutic purposes or more general purposes (such as general physical fitness or mental health).

As used herein, the term "digital care platform" may include a technology-based or technology-driven platform designed to facilitate one or more health-related and/or wellness-related activities. As mentioned above with reference to "digital care," activities associated with a digital care platform may be aimed at addressing or diagnosing specific conditions and/or aimed at promoting physical fitness or well-being and/or aimed at preventative care. Accordingly, utilization of a digital care platform is not necessarily limited to diagnosing, treating, or managing specific conditions, as it may also be used for general or regular exercise or mindfulness activities (for example). A digital care platform may integrate or leverage various digital tools, such as mobile applications, web applications, wearable devices, motion trackers, other sensors, and/or interactive software to provide personalized solutions.

In the context of digital care or a digital care platform, the term "session," as used herein, may include a user engagement with the digital care platform. An engagement may involve the user performing one or more exercises or activities based on instructions or guidance provided by the digital care platform. Where exercises are performed, the session can be referred to as an exercise session. A session may be tailored to address a specific health condition (e.g., through targeted exercises) or aimed at supporting general wellness, prevention, or fitness goals, without being targeted to a specific condition. Accordingly, the nature and content of a session may depend on a user's needs or selections.

An example system communicates with a plurality of tracked users (e.g., patients or other users of a digital care platform) and a plurality of supervising users (e.g., therapists, clinicians, or other humans managing or supervising digital care programs). The system may include hardware devices associated with the tracked users, such as sensors for capturing movement and/or other user data.

In some examples, the system maintains user data in a database. The user data may include user tracking data and user history data. The user tracking data may be based at least partially on sensor data from hardware devices associated with the tracked users, while the user history data may comprise user interactions related to their respective activity programs.

For example, the user tracking data can include information collected from hardware devices associated with tracked users that reflects current or recent user status, activities, or conditions. The user tracking data may comprise real-time tracking data from one or more activity sessions, performance data, biomechanical data, physiological data, behavioral data, and/or environmental data. User tracking data may include motion capture information from image sensors showing exercise form and movement patterns, heart rate measurements from wearable devices, pressure readings from specialized sensors, and/or positional data indicating user movements during therapeutic activities. The user tracking data may be collected continuously or intermittently during sessions and may be processed to generate measurements of user performance, engagement, and/or physiological responses to therapeutic interventions.

User history data can, for example, include stored information related to a tracked user's past interactions with and experiences in an activity program of a digital care platform. The user history data may comprise clinical history data, baseline assessment data, enrollment data, activity session data, progress evaluation data, communication history data, and/or supervising user feedback data stored in a database accessible by one or more machine learning models. For example, user history data can include records of previously completed exercise sessions with a user's comments, responses to questionnaires, noted symptoms, progress measurements over time, messages exchanged with supervising users, messages exchanged with the digital care platform itself, and/or documented clinical assessments. The user history data may be collected over various timeframes, from initial enrollment through ongoing participation in activity programs, and may be structured to provide contextual information about the tracked user's treatment journey, adherence patterns, response to interventions, and clinical progression.

The system processes user data using one or more machine learning models to obtain recommendation data. The recommendation data may comprise recommendations related to activity programs (e.g., a list of exercises to perform or mental health activities to complete) and user interactions (e.g., a suggested message to send to a user related to their physical or mental health).

In some examples, the recommendation data includes automatically generated exploratory program elements. For example, recommendation data may include suggestions to modify exercise sequences, increase or decrease repetitions, remove certain exercises based on detected user limitations, add or remove mental health-related activities, adjust session frequency, or introduce new therapeutic elements not previously included in a user's program. The recommendation data may be presented to supervising users for validation before implementation and may contain both standard interventions drawn from established clinical protocols as well as novel elements generated through automated analysis of patterns. In some examples, an exploratory program element defines a novel activity or activity combination not found in a user database of the digital care platform.

The system may generate validated activity program data based on user input received from supervising users in response to recommendation data. For example, a supervising user receives recommendation data as generated by a machine learning model and provides input indicating approval, denial, or updates to the recommendation data, including any exploratory program elements therein.

Validated activity program data may thus include program specifications generated based on user input received from supervising users in response to recommendation data. The validated activity program data may represent a final, approved version of activity program modifications after review by a therapist or clinical expert. For example, validated activity program data may include a set of exercises with specific repetition counts, sequences, and modifications that have been adjusted based on recommendation data and then explicitly approved by a supervising user before implementation with tracked users. The validated activity program data may incorporate some, all, or none of the automatically generated exploratory program elements from the recommendation data, depending on the supervising user's clinical judgment, and may include additional modifications introduced directly by the supervising user during the validation process. This validated data serves as the basis for activity programs that tracked users actually perform, with the results of these programs subsequently recorded in the user data.

Once validated through supervising user input, a tracked user performs activities associated with their activity program (e.g., a personalized set and schedule of exercises). The system may continuously update the user data to record results of activity programs performed by users according to their respective activity programs. For example, the system records the outcomes associated with changes made to an activity program of a user (e.g., whether the changes led to improvements).

In some implementations, the system continuously modifies parameters of the one or more machine learning models used to generate the recommendation data (e.g., through automated reinforcement learning). In some examples, the system generates and/or updates a first reinforcement learning signal based on recommendations validated by supervising users, and generates and/or updates a second reinforcement learning signal based on activity program results. Both reinforcement learning signals are then applied to modify the one or more machine learning models.

In some examples, the first reinforcement learning signal and the second reinforcement learning signal comprise or are derived from paired data comprising a supervising user-approved recommendation and a corresponding measured outcome in relation to a particular activity program.

The system's machine learning architecture may thus implement a learning approach that can improve performance of the digital care platform over time. For example, by simultaneously processing both clinician validation signals and outcome-based signals, the system can automatically modify model parameters in a way that maintains clinical safety while discovering or exploring new therapeutic patterns. The continuous feedback loop between the data collected using the observation system, analysis and recommendations generated by the reasoning system, and data delivery by the communication system, can help to improve system resource utilization, recommendation generation, user tracking, and/or other technological performance.

Hardware devices associated with tracked users may include tablet computing devices, mobile phones, wearable devices, body-mounted sensors, and/or intra-body devices. In some examples, the system utilizes image sensors (e.g., cameras of tablet computing devices and/or cameras of mobile phones) that capture images of tracked users performing exercises. These images are processed to generate real-time tracking data that updates the user tracking data. The system may display a user interface at a user device, showing a digital video feed of the images along with activity tracking output or exercise instructions.

The system may employ various types of machine learning models or AI agents, including, for example, recommender models/agents, session analyzer models/agents, behavioral analyzer models/agents, and/or user engagement models/agents to generate personalized interactions. The system can receive feedback from users in response to personalized interactions and automatically update activity programs accordingly. One or more machine learning models executed via the digital care platform may include a generative model, such as a generative language model (e.g., a Large Language Model (LLM) with a transformer architecture). In various examples, a generative model is fine-tuned on thousands or even millions of sessions to help the generative model generate better recommendation data.

The system may employ multiple software agents (e.g., AI agents). A software agent can include a software component that performs automated tasks. Software agents may be implemented as AI modules, such as modules leveraging language model capabilities, as non-AI components such as scripts, programs, or algorithms designed to execute specific functions, or combinations thereof. In some embodiments, software agents operate independently and use software tools to analyze, process, or transform data according to predefined rules or learned patterns. Software agents may communicate with each other and other components in a system, receive inputs, process data, and produce outputs without human intervention.

FIG. 1

FIG. 1 is a diagrammatic representation of a networked computing environment 100, including a digital care platform 102, in which some examples of the present disclosure may be implemented or deployed. One or more servers in a server system 104 provide server-side functionality via a network 106 to a networked device, in the example form of a computing device 108 that is accessed by a user 110. The computing device 108 may be a portable computing device, such as a tablet device or a mobile phone.

A web client 112 (e.g., a browser) or a programmatic client 114 (e.g., an "app") may be hosted and executed on the computing device 108. In some examples, the computing device 108 executes further web clients or programmatic clients, such as the programmatic client 116 shown in broken lines in FIG. 1.

The one or more servers in the server system 104 also provide server-side functionality via the network 106 to a computing device 118 that is accessed by a supervising user in the example form of a therapist 120. The computing device 118 can, for example, be a personal computer, a laptop, a tablet device, or a mobile phone.

The networked computing environment 100 may thus include a device of a user and a device of a therapist. Although not shown in FIG. 1, the computing device 118 may include a web client or a programmatic client similar to the web client 112 or programmatic client 114 (or the programmatic client 116) of the computing device 108.

The user 110 may be a person who engages with the digital care platform 102 to benefit from any of its features, or to seek guidance, support, or interventions. A user may have a specific medical condition that needs to be addressed, or may utilize digital care for more general or less defined purposes, such as regular exercise or mindfulness activities. The user may be assigned to a particular supervising user.

The therapist 120 may be a therapist, clinician, or other person involved with digital care who assists the user 110 via one or more digital channels, thus acting as a supervising user in the context of the digital care platform 102. For example, the therapist 120 can be a physical therapist, clinician, physician, healthcare professional, or other worker (e.g., a personal trainer) that treats, manages, communicates with, or otherwise assists with advising, planning, guiding, motivating, treating, or rehabilitating a user in a digital care context. For example, in the context of the present disclosure, the therapist 120 can be a person assigned to work with the user 110 by offering advice, designing, adapting, or managing digital care programs, and/or providing motivation and support. In some examples, the therapist 120 can have multiple users assigned to them.

An Application Programming Interface (API) server 126 and a web server 122 provide respective programmatic and web interfaces to components of the server system 104. An application server 124 hosts or provides the digital care platform 102, which may also be referred to as a digital care system, and which includes one or more subsystems, components, modules, or applications.

The computing device 108 and the computing device 118 can each communicate with the application server 124, for example, via the web interface supported by the web server 122 or via the programmatic interface provided by the API server 126.

It will be appreciated that, although a single computing device 108 of the user 110 and a single computing device 118 of the therapist 120 are shown in FIG. 1, a plurality of other devices may be communicatively coupled to the server system 104 in some examples. For example, multiple users may use their respective devices to access the digital care platform 102, and multiple supervising users may use their respective devices to access the digital care platform 102, with each user being assigned at least one supervising user to assist them. Further, while certain functions are described herein as being performed at either a user device (e.g., web client 112 or programmatic client 114) or the server system 104, the location of certain functionality either within a user device or the server system 104 may be a design choice.

The application server 124 is communicatively coupled to one or more database servers 128, facilitating access to one or more information storage repositories (e.g., a database 130). In some examples, the database 130 includes storage devices that store information to be processed or transmitted by the digital care platform 102.

The application server 124 accesses application data (e.g., application data stored by the database servers 128 or database 130) to provide one or more applications to the computing device 108 and the computing device 118 (e.g., via a web interface 132 or an app interface 134). The digital care platform 102 may provide a digital care application, or multiple digital care applications, to be accessible via the computing device 108 or the computing device 118.

The digital care platform 102 can operate to combine specialized hardware sensors, multi-layered machine learning models, and human clinical expertise. For example, the digital care platform 102 employs purpose-built hardware components that capture high-precision biomechanical and physiological measurements, which feed into a reasoning layer comprising multiple specialized large language models fine-tuned on clinical data. These models process complex multi-modal inputs including session data, behavioral patterns, and/or conversational interactions to generate contextually-aware clinical recommendations. In some examples, the digital care platform 102 maintains safety and clinical appropriateness through a dual-input reinforcement learning mechanism that simultaneously optimizes for human expert validation and measured treatment outcomes.

In some examples, the user 110 accesses a user portal of the digital care application to utilize various functionality, such as consulting virtually with the therapist 120, receiving a customized digital care program, receiving details of exercises to perform, receiving real-time feedback and instructions while performing exercises, interacting with the digital care platform 102 (e.g., providing input and receiving response messages), and reviewing educational content, while the therapist 120 may access a therapist portal of the digital care application to utilize various functionality, such as consulting virtually with the user 110, accessing a therapy workflow in a user management user interface, and/or tracking and managing users.

Where multiple digital care applications are provided, different aspects of digital care may be provided via the respective applications. In some examples, a first application (e.g., the programmatic client 114) is a mobile application that provides an app interface (e.g., the app interface 134) for features such as educational videos, cognitive behavioral therapy (CBT), and a communication channel with therapists, while a second application (e.g., the programmatic client 116) is a tablet application that provides access to exercises and an app interface (e.g., the app interface 136) for such purposes. The digital care application is referred to herein primarily as a single application for ease of reference and to facilitate understanding of aspects described herein. It will, however, be appreciated that, where this disclosure may refer to a single "digital care application" having certain functions, such functions may be performed by a single application or distributed across multiple applications. The digital care application, or applications, may be mobile applications, tablet applications, web applications, combinations thereof, or other types of applications.

To access the digital care application provided by the digital care platform 102, a user may create an account or access an existing account with a service provider associated with the server system 104 (e.g., a digital health services provider). The user 110 or the therapist 120 can, in some examples, access the digital care application using a dedicated programmatic client (e.g., the programmatic client 114 and/or the programmatic client 116), in which case some functionality may be provided client-side, and other functionality may be provided server-side.

Data stored in the database 130 may include various user data, including motion data, therapy data (e.g., exercise data), performance data, and the like. User data is captured, collected, or stored with applicable user notices and consents. To ensure limited and authorized use of user data, access to this data is restricted to authorized personnel only. In addition, appropriate technical and organizational measures are implemented to ensure the security and confidentiality of this user data.

The server system 104 may include multiple of the databases 130. Data stored in the database 130 or databases may originate from various data sources. The data sources may include structured data and/or unstructured data. User data of the user 110 stored in the database 130 may include, for example, data describing a therapy goal of a user, data describing a baseline condition of the user, data describing changes in a condition of the user, motion data of the user, or performance data of the user related to one or more sessions. Examples of the performance data include data relating to range of motion, exercise types, exercise completion data, or movement accuracy.

The server system 104 may further host a machine learning system 138. The machine learning system 138 may be used to implement one or more aspects of a machine learning pipeline. For example, the machine learning system 138 may include components enabled to train models based on historic data, to fine-tune models, and/or to deploy models for inference. Various aspects of machine learning pipelines and other AI-related features are described elsewhere in the present disclosure.

The machine learning system 138 may leverage one or more machine learning models to perform functions as described herein, such as performing computer vision tasks, generating real-time feedback, generating personalized recommendations for the user 110 (e.g., for review by the therapist 120) and/or generating personalized messages for the user 110.

The machine learning models may include models used in computer vision tasks, such as motion tracking, pose estimation, pose tracking, depth estimation, and so forth. Such models may include one or more of Convolutional Neural Networks (CNNs) (e.g., ResNet-based architectures, Hourglass Networks such as Stacked Hourglass Networks, Mask R-CNN, etc.), Recurrent Neural Networks (RNNs) including Long Short-Term Memory (LSTM) networks or Gated Recurrent Units (GRUs), DeepLab models (e.g., Deep-Labv3+), U-Net models, SegNet, Pyramid Scene Parsing Network (PSP), Transformer models such as Vision Transformer (ViT), Spatial Transformer Networks, Graph Convolutional Networks (GCNs), Optical Flow models such as Flow Net or PWC-Net, OpenPose, PoseNet, AlphaPose, DeepPose, DensePose, YOLO-Pose, SimpleBaseline, Mask R-CNN, MoveNet, BlazePose by Google™, VoxelPose, VIBE (Video Inference for Human Body Pose and Shape Estimation), Multi-person Pose Estimation models and/or techniques such as Associative Embedding or PersonLab, and so forth. For example, a keypoint generation component of the digital care platform 102 (e.g., implemented locally at the computing device 108 via the digital care application) can make use of a pose estimation model such as BlazePose to process images captured by the computing device 108.

The machine learning models may include generative machine learning models, such as one or more language models. As an example, an LLM is a machine learning model trained on vast amounts of data to enable it to process inputs and generate language and, in some cases, other types of content to perform a wide range of tasks. An LLM is able to perform these functions due to its large number of parameters (e.g., billions) enabling it to capture, for example, patterns in language. In some examples, an LLM serves as an engine for natural language processing tasks within a digital care system. The machine learning system 138 may leverage one or more LLMs to perform a variety of functions to support the operation of the digital care platform 102. These functions may include the generation of personalized recommendations to better manage therapy or personalized feedback, the interpretation of input and queries, and the synthesis of complex data into comprehensible reports. Various prompting techniques, such as few-shot solutions, can be implemented to improve LLM outputs.

The machine learning system 138 may employ a combination of machine learning models that are internally hosted or employed at a user device, e.g., for operations that benefit from rapid processing, and externally hosted machine learning models for operations that can benefit from the scalability and computational power of cloud-based services. Furthermore, the machine learning system 138 is designed to be flexible and scalable, enabling the integration of new models as they become available or as the needs of the digital care platform 102 evolve.

In some examples, the digital care platform 102 has continuous learning capabilities implemented through a three-layer architecture: an initial training layer using historical clinical decisions, a feedback layer incorporating newly validated decisions, and a safe experimentation layer that enables discovery of novel approaches under human oversight. This architecture allows the digital care platform 102 to go beyond simple historical pattern detection or retrieval-augmented generation by performing true contextual reasoning, such as by considering each user's current rehabilitation stage, progress metrics, and/or real-time sensor inputs when generating responses.

The digital care platform 102 can maintain procedural rigor through state machine orchestration while allowing for natural conversational flexibility, decomposing complex clinical protocols into discrete states with well-defined transitions. This can facilitate, for example, multi-turn interactions that demonstrate both clinical knowledge and contextual awareness, such as correlating reported symptoms with recent activity patterns or adapting therapeutic recommendations based on measured physiological responses.

In some examples, reinforcement learning allows one or more models leveraged by the digital care platform 102 to be continuously updated based on feedback signals derived from real-world performance data. In an automated learning cycle, a system can process both clinical validation decisions and user outcome measurements. The digital care platform 102 can evolve by generating exploratory program elements (such as variations in exercise sequencing or intensity) and learning from their effectiveness while remaining grounded in clinical safety through a human-in-the-loop framework. In this way, the digital care platform 102 can efficiently identify how slight variations in clinical management and engagement strategies help identify new patterns that contribute to improved outcomes.

In various examples, the digital care platform 102 implements an automated framework leveraging reinforcement learning signals comprising dual inputs: a first reinforcement learning signal based on validation feedback from supervising users (such as therapists approving or modifying recommended treatment adjustments), and a second reinforcement learning signal based on measured outcomes from activity programs (such as patient improvement metrics, adherence data, or engagement measurements). These signals function as evaluation mechanisms that inform the system which patterns and decisions lead to successful outcomes, enabling continuous refinement of parameters.

A learning approach in the digital care platform 102 can involve fine-tuning, such as supervised fine-tuning. Supervised fine-tuning can include a process for modifying machine learning models where human experts (such as therapists or clinicians) provide explicit guidance and corrections that directly shape parameters and future outputs. In the digital care platform context, supervised fine-tuning may involve clinicians reviewing recommendation data and providing feedback that explicitly indicates whether the recommendations align with clinical best practices or safe practices, which is then used to update model parameters. The supervised fine-tuning process may include providing corrective examples, adjusting recommendation weights, or modifying decision boundaries within the models to improve their performance.

In some examples, third-party applications can communicate with the application server 124 via the programmatic interface provided by the API server 126 (or via another channel). For example, a third-party application may support one or more features or functions on a website or platform hosted by a third party, or may perform certain methodologies and provide input or output information to the application server 124 for further processing or publication. For example, the application server 124 may utilize functionality of machine learning models that are hosted by servers external to the server system 104.

The network 106 may be any network that enables communication between or among machines, databases, and devices. Accordingly, the network 106 may be a wired network, a wireless network (e.g., a mobile or cellular network), or any suitable combination thereof. The network 106 may include one or more portions that constitute a private network, a public network (e.g., the Internet), or any suitable combination thereof.

FIG. 2

Figure 2:
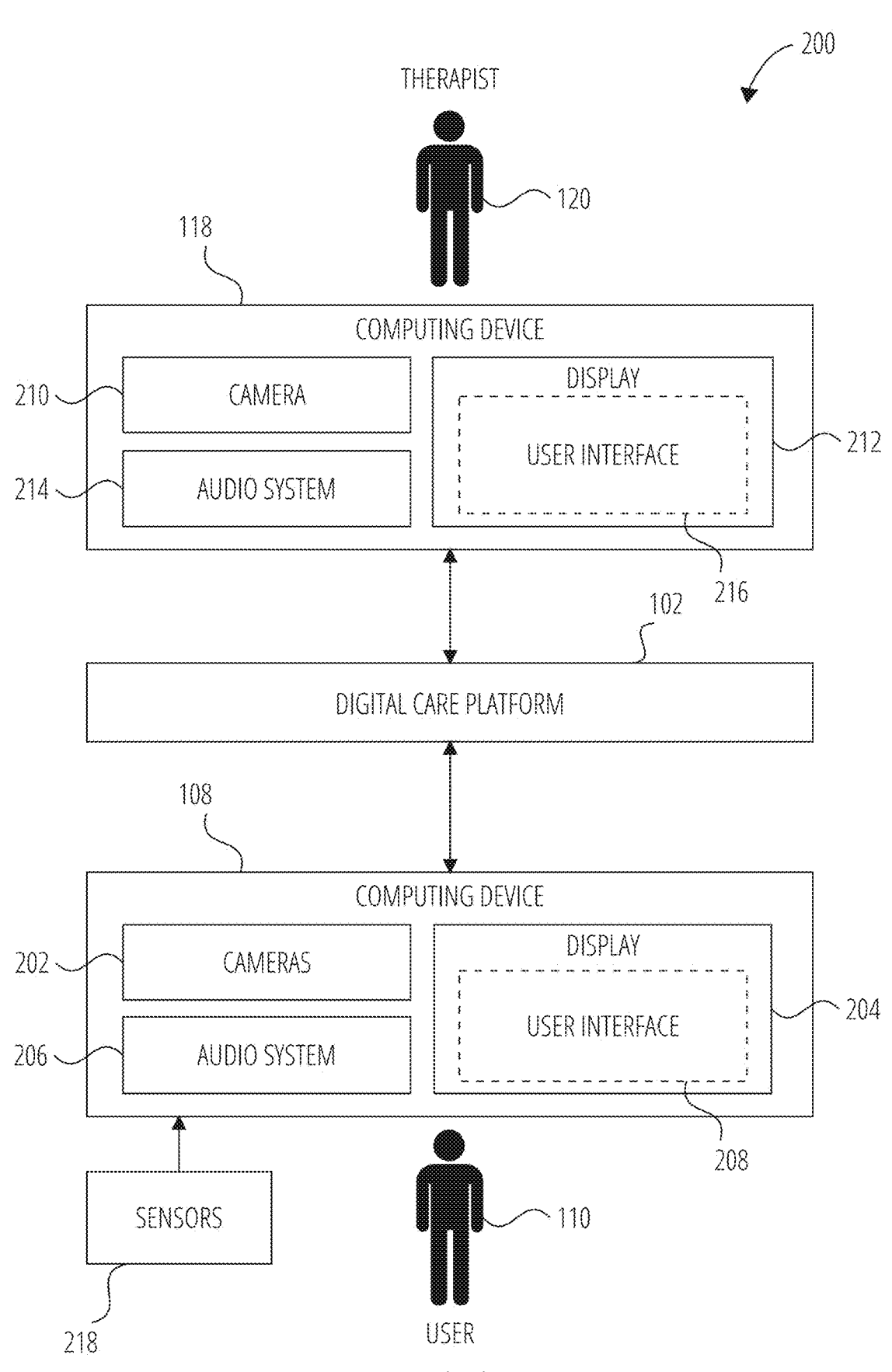
FIG. 2 is an interaction diagram illustrating interactions between computing devices in the context of a digital care platform, according to some examples.

FIG. 2 shows an interaction diagram 200 depicting interactions between a user device of a supervising user in the digital care platform 102 of FIG. 1 and a user device of a user, according to some examples. In FIG. 2, the computing device 118 of the therapist 120 of FIG. 1 and the computing device 108 of the user 110 of FIG. 1 are shown for ease of reference. It will be appreciated that similar interactions may be performed with other devices connected to the digital care platform 102. It will further be understood that only a few selected components of the computing device 108 and the computing device 118 are shown in FIG. 2 to describe certain functionality, and that the computing device 108 and the computing device 118 may include numerous other components.

As discussed with reference to FIG. 1, both the computing device 108 and the computing device 118 are devices that can communicate with or operate as part of the digital care platform 102 (e.g., by accessing a digital care application). In at least some embodiments, the computing device 108 and the computing device 118 may be mobile phones, tablets, personal computers, or combinations thereof.

The computing device 108 includes, or is connected to, cameras 202, a display 204, and an audio system 206. The computing device 108 further includes at least one processor, at least one memory, and a communication module (not shown) for communicating with the digital care platform 102 and one or more other devices.

The cameras 202 may capture images or video content of the user 110 performing exercises to allow tracking of user motion via computer vision techniques. For example, identification of anatomical landmarks, measurement of distances, and tracking of body parts may be performed using computer vision techniques such as those described elsewhere in the present disclosure.

The cameras 202 and other components of the computing device 108 (e.g., microphone loudspeaker of the audio system 206 as well as communication modules) may also facilitate virtual consultations. The user 110 may connect with the therapist 120 via the digital care platform 102, for example, to virtually consult with the therapist 120. The display 204 is used to provide a user interface 208 of the digital care platform 102, such as a user interface of the digital care application.

The audio system 206 may, for example, include one or more microphones and one or more loudspeakers or modules for connecting to external microphones and/or loudspeakers. This enables the user 110 to provide input to the digital care platform 102 in audio format and to receive audio messages from the digital care platform 102.

The user 110 may, for example, enter user data, such as demographic information, clinical history, and symptoms (e.g., identification of painful zones and pain levels), and the data is then transmitted to the digital care platform 102. The digital care platform 102 may generate a digital care program, such as an activity program, and make it available to the user 110. For example, the digital care program can be a physical therapy program that guides the user 110 through an 8-week program or a 12-week program to treat or improve Lower Back Pain (LBP) or another MSK condition through targeted physical therapy (the actual duration may vary or be dynamic, for example, based on user condition, engagement, or recovery trajectory). Activity programs can also include more general exercises, mindfulness exercises, etc.

The computing device 108 may provide (or cause another device to provide) user-perceptible signals, such as exercise instructions or messages. For example, the display 204 and one or more loudspeakers of the audio system 206 may provide such user-perceptible signals. That is to say, the computing device 108 may comprise one or more of visual output means, audio output means, vibrating means, or other means for providing user-perceptible signals in the form of sounds, vibration, animated graphics, etc.

For example, the display 204 of the computing device 108 may show instructions and/or information to the user 110 about the digital care program, such as predetermined movements that are to be performed by the user 110 or results of the exercises performed by the user 110 presented via the user interface 208. The computing device 108 may thus provide the user interface 208 to present instructions and/or information to the user and/or to receive inputs from the user.

Any of these data can be transmitted to and/or received from another electronic device thanks to communicative couplings between the computing device 118, the digital care platform 102, and the computing device 108 (e.g., over the network 106 of FIG. 1). For example, the therapist 120 is able to receive the feedback at the computing device 118 in a hospital or other facility, such as an outpatient clinic, retirement home, or elderly care facility, or even at their home, so as to monitor the evolution or progress of the user 110.

In some examples, the computing device 108 captures audio feedback via one or more audio sensors of the audio system 206 such that the audio feedback can be processed by the computing device 108 or at the digital care platform 102 (e.g., to assist in determining the case or difficulty experienced by the user 110 in performing the exercises). In some examples, while performing exercises, the computing device 108 provides real-time messages from an AI care specialist and the user 110 is enabled to respond verbally to such messages. For example, the user 110 responds, the digital care platform 102 processes the response via one or more AI agents, generates a follow-up response, and transmits the follow-up response back to the user 110 via the computing device 108.

In some examples, the user 110 is provided with additional sensors or trackers, such as sensors 218 shown in FIG. 2. For example, the user 110 may be provided with one or more body-mounted trackers and/or one or more biosensors or vital sign sensors. Such sensors or trackers can include one or more Inertial Measurement Unit (IMUs) and one or more components for detecting or measuring biological or physiological signals from the body. Examples of the sensors 218 include sensors for measuring respiration rate, body temperature, pulse rate, or a combination of two or more thereof. Sensors can be incorporated into a wearable device such as a watch or wristband. In some examples, the digital care platform 102 obtains information from environmental sensors associated with the user 110, such as an ambient temperature sensor.

The therapist 120 can manage, edit, or track the digital care programs of one or various users on the computing device 118. For example, based on sensor measurements, user-reported feedback, and AI generated analyses received with respect to the user 110, the therapist 120 is able to monitor and adjust an activity program by changing the difficulty of the movements or exercises, changing the number of repetitions thereof, prescribing new movements, and so forth. The therapist 120 may implement programs or make adjustments based on AI-generated recommendations (e.g., from the reasoning system 304 of FIG. 3, as described below).

In some examples, the digital care platform 102 provides for bidirectional communication with users, for example, through a secure chat functionality or a text messaging facility available when the digital care application is installed on the computing device 118 and the computing device 108. This may enable, for example, virtual consultations or text message-based "chats" between users and therapists (human therapists or an AI care specialist).

The computing device 118 also includes, or is connected to, a camera 210 and audio system 214, for example, to facilitate such communications. As discussed with reference to the computing device 108, the computing device 118 also includes a display 212, at least one processor, at least one memory, and a communication module (not shown) for communicating with the digital care platform 102 and one or more other devices.

A user interface 216 may be provided to the therapist 120 via the display 212 (e.g., a user interface of the digital care application). A user management user interface may allow the therapist 120 to track, manage, and/or interact with various users assigned to them in the context of the digital care platform 102.

For example, after authenticating into the digital care platform 102 (e.g., logging into the digital care application), the therapist 120 can access the user interface 216 for their assigned users (e.g., the user 110). The user interface 216 may enable the therapist 120 to visualize baseline information, changes in user data over time, including, for example, measured range of motion (e.g., using computer vision techniques), self-reported pain ratings (e.g., a reported pain level after each session), utilization data, and/or fatigue levels. The user interface 216 can also provide predicted risk alerts, next steps, tasks, and/or timeline views of exercise activity to assist the therapist 120.

The user interface 216 may enable the therapist 120 to prescribe interventions by selecting exercise regimens (these may be referred to as "prescriptions") and scheduling follow-ups. In some examples, the user interface 216 is dynamically and automatically adjusted or updated to reflect the current state of the user 110 based on the latest measurements and predictions.

The user interface 216 may provide automatically generated content. In some examples, the digital care platform 102 processes user data from various sources and automatically generates recommendations that are personalized for each user. The digital care platform 102 can leverage generative AI techniques to generate such personalized recommendations and then automatically surface them to the therapist 120 within the user interface 216. For example, the therapist 120 can access a profile of the user 110 within the user interface 216 to view and act on (e.g., approve, modify and approve, or reject) personalized recommendations that were automatically generated for the user 110.

FIG. 3

Figure 3:
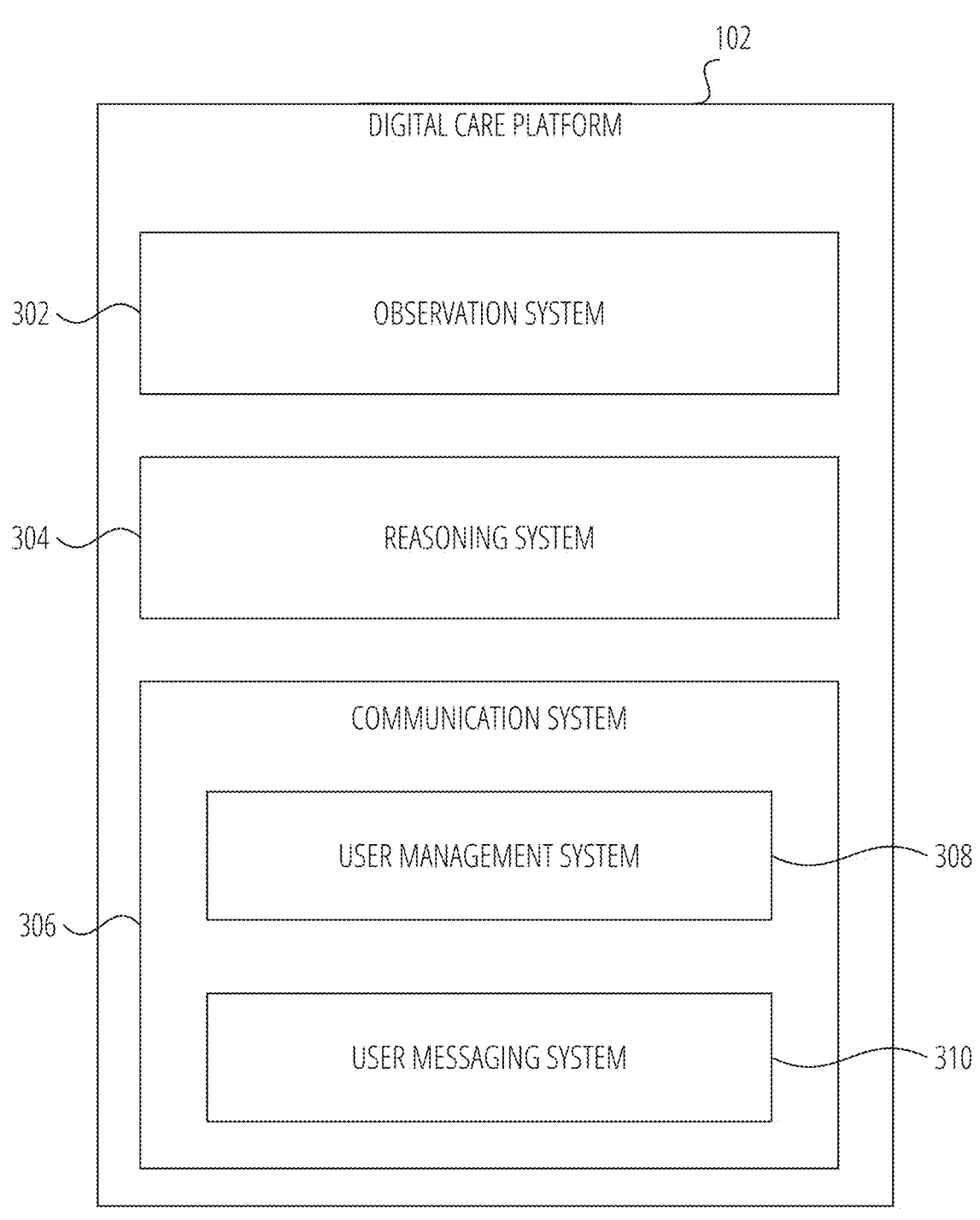
FIG. 3 is a block diagram illustrating systems within a digital care platform, including an observation system, a reasoning system, and a communication system, according to some examples.

FIG. 3 illustrates systems within the digital care platform 102 of FIG. 1, according to some examples. In FIG. 3, the digital care platform 102 is shown to include an observation system 302, a reasoning system 304, and a communication system 306. The communication system 306 includes a user management system 308 and a user messaging system 310. In some examples, through the combination of systems such as those shown in FIG. 3, the digital care platform 102 provides end-to-end, AI-powered digital care. Functions of the observation system 302, the reasoning system 304, and the communication system 306 can be performed at a remote server, locally at a user device or therapist device, or combinations thereof.

It should be understood that this and other arrangements described herein are set forth only as examples. Other arrangements and elements (e.g., machines, interfaces, components, agents, functions, orders, groupings of functions, etc.) may be used in addition to or instead of those shown, and some elements may be omitted altogether. Further, many of the elements described herein are functional entities that may be implemented as discrete or distributed components or in conjunction with other components, and in any suitable combination and location. Various functions described herein as being performed by entities may be carried out by hardware, firmware, and/or software. For instance, various functions may be carried out using one or more processor executing instructions stored in one or more memories.

In some examples, the observation system 302 captures multidimensional data through hardware and sensing technology. In some examples, the observation system 302 is designed to create an up-to-date and comprehensive view of user status and behavior that serves as a foundation for downstream clinical decision-making.

In some examples, the observation system 302 collects and processes image data from the computing device 108, such as image data captured by the computing device 108 during exercise sessions. The observation system 302 may perform pose estimation to identify and track body landmarks of the user 110 in real-time during exercise performance. This may involve analyzing the image data and positional information to create a skeletal representation of the body that can be used for movement analysis. The observation system 302 can track landmarks across different exercise types.

The observation system 302 can include a pose estimation component employing one or more pose detection and/or pose regression models, as made available by frameworks, APIs, or systems such as OpenPose, PoseNet, AlphaPose, DeepPose, DensePose, YOLO-Pose, Mask R-CNN, MoveNet, TensorFlow Pose estimation, MediaPipe Pose, BlazePose by Google™, and so forth. One or more proprietary models can be used as an alternative to, or in addition to, the aforementioned example models. In some examples, a pose estimation component uses a keypoint-based pose detection and/or keypoint-based pose regression model. For example, the observation system 302 can run a model that uses multiple keypoints covering head region keypoints (e.g., facial features, cars, etc.) and body joints.

In some examples, the observation system 302 collects alternative or additional data through other hardware, such as the sensors 218, wearable devices (e.g., wearable motion trackers or biosensors), or through other means such as user feedback. The observation system 302 may provide comprehensive observational data for clinical assessment and personalized therapeutic guidance in remote settings.

In some examples, the observation system 302 interfaces directly with users to enable session delivery with real-time feedback, creating a continuous assessment loop that may not be possible in traditional care settings. The observation system 302 may utilize specialized form factors and purpose-built systems designed for robustness to variability in uncontrolled real-world scenarios and for usability by non-technical users.

The reasoning system 304 executes decision-making through a multi-layered approach. In some examples, the reasoning system 304 processes the information collected by the observation system 302 to extract clinical insights and generate status or recommendation data. The reasoning system 304 can operate in real-time (e.g., to allow for feedback during an exercise session) and/or in response to certain triggers.

For example, the reasoning system 304 can respond to clinical triggers that signal potential changes in user status, such as enrollment of a new user requiring initial assessment, completion of a session generating new data, periods of non-engagement indicating potential adherence issues, user communications containing clinically relevant information, scheduled reassessment intervals based on clinical protocols, or significant changes in behavioral patterns detected by monitoring systems.

In some examples, the reasoning system 304 processes a user's full clinical history, explicit patient feedback and/or expert human knowledge. The reasoning system 304 may utilize specialized machine learning models trained on clinical data, activated to mimic a clinical decision-making process.

In various examples, a reasoning process executed by the reasoning system 304 (e.g., an AI agent-driven reasoning process) culminates in the generation of recommendation data for review by a supervising user such as a therapist. For example, the reasoning system 304 seeks to generate an optimal or near-optimal course of action for a user. This can include therapy adjustments, behavioral recommendations, or clinical escalation recommendations when appropriate. In various examples, outputs from the reasoning system 304 are reviewed by a human and are only implemented after human approval or validation.

The reasoning system 304 can operate to generate one or multiple exploratory program elements and learn from the outcomes thereof. For example, the reasoning system 304 generates exploratory program elements that introduce therapeutic variations not previously present in a user's activity program. The exploratory program element may comprise a new activity not contained in the user history data, an activity variation not contained in the user history data, or a new activity sequence not contained in the user history data. Exploratory program elements may include suggesting a different order for existing exercises to improve progression, introducing a modified version of a standard exercise to address a specific limitation, or recommending an entirely new exercise that addresses an identified clinical need based on recent tracking data. Exploratory program elements are validated by human reviewers, thereby expanding the range of therapeutic options beyond traditional programmatic approaches while remaining suitably grounded and safe.

The communication system 306 focuses on interactions with the user 110, which may include those on behalf of the therapist 120. In some examples, the communication system 306 allows for interactions with the user 110 during sessions and aims to drive engagement in various stages of treatment.

The communication system 306 may provide real-time feedback and guidance based on motion tracking data generated by the observation system 302 and/or the reasoning system 304. The communication system 306 may display, on a display screen of the computing device 108 and while the user is performing exercises, a user interface comprising a digital video feed with motion tracking output, responses to user queries, or instructions for performing exercises.

The communication system 306 may include different conversation agents (e.g., language model-based agents) for various purposes, including agents with state machine flow control. This may include guardrail agents that employ language models as judges and content revision mechanisms to help with content safety. The communication system 306 may also incorporate retrieval augmented generation (RAG) databases to allow for factual and up-to-date information communication, as well as speech-to-text and text-to-speech algorithms.

In some examples, the user management system 308 handles the overall administration of therapy programs in a manner that enables interfacing the supervising user. The user management system 308 tracks user progress across multiple sessions, manages exercise prescriptions, and adjusts therapy parameters based on performance data (e.g., together with the reasoning system 304). The user management system 308 is configured to work with the reasoning system 304 to process user data and detect events, such as completion of a session, arrival of a new chat message, or lack of user engagement for a predetermined number of days. When such events occur, the user management system 308 works with the reasoning system 304 to recommend actions or interventions.

The user management system 308 can inform the therapist 120 of a proposed initial prescription based on baseline data (e.g., individual characteristics, clinical conditions, user needs, and goals). The user management system 308 can also monitor progress over time and introduce tailored prescription adjustments, presenting recommended modifications for therapist review and approval. In some examples, the user management system 308 provides, to the therapist 120, a user interface with information and recommendations related to the user 110.

In some examples, the user management system 308 allows therapists to track, manage, and interact with various users assigned to them in the context of the digital care platform 102. In some examples, after authenticating into the digital care platform 102, therapists may access user interfaces for their assigned users to visualize baseline information, changes in user data over time, and other relevant clinical information. The user management system 308 may enable therapists to prescribe interventions by selecting exercise regimens and scheduling follow-ups. In some examples, the user management system 308 may be dynamically and automatically adjusted or updated to reflect the current state of users based on the latest measurements and predictions. The system may provide automatically generated content, such as personalized recommendations generated using artificial intelligence techniques that therapists can approve, modify, or reject for their users.

The user messaging system 310 facilitates communication between users and the digital care platform 102 (e.g., its therapists or AI systems). In some examples, the user messaging system 310 enables asynchronous messaging between users and their therapists, allowing for questions, feedback, and guidance outside of scheduled sessions. The user messaging system 310 may be responsible for in-session interactions with the user, generating personalized messages delivered at certain points in time, and automatically responding to queries during a session.

In some examples, when interacting with the user in real time during a session, the user messaging system 310 generates and transmits messages rapidly using AI technology, simulating the role of a human therapist working with and encouraging the user in real time. The user messaging system 310 can also deliver messages originating from the user management system 308, such as motivational messages recommended by the user management system 308 (e.g., as approved by the therapist 120).

The user messaging system 310 can communicate with the reasoning system 304 to allow for the generation of, for example, real-time AI-driven responses to user queries. In some examples, when the user messaging system 310 interacts directly with the user 110 without live human supervision (such as by using an "AI care specialist" to interact with the user during sessions), state-machine-driven language model orchestration is employed. This breaks down complex procedures into multiple steps, forcing an AI system (e.g., a language model-based agent) to follow one step at a time while using it to determine the next step based on user input. This approach may combine the model's ability to handle natural language with the rigorous flow that a state machine provides.

The user messaging system 310 provides bidirectional communication capabilities between users and therapists. In some examples, the user messaging system 310 enables secure chat functionality or text messaging facilities available when the digital care application is installed on computing devices. The user messaging system 310 may facilitate virtual consultations or text message-based communications between users and therapists, which may include human therapists or AI care specialists. In some examples, the user messaging system 310 may integrate with the communication system 306 to deliver personalized messages designed to improve understanding and adherence based on user communication preferences, past engagement patterns, and current clinical status. The user messaging system 310 may employ natural language processing capabilities to understand user inquiries and generate appropriate responses.

The communication system 306, together with the reasoning system 304, can utilize generative machine learning models, such as an LLM, to generate personalized recommendations or personalized messages. For example, the communication system 306 or the reasoning system 304 dynamically generates a prompt including user data and an instruction for generating a personalized recommendation or message. The prompt may then automatically be provided to a generative machine learning model (e.g., an LLM) to obtain the personalized recommendation or message, substantially in real-time. Prompt engineering may be employed to describe the task to the model, incorporating, for example, movement statistics and relevant past information from user history. This can result in feedback or recommendations that are more appropriate to the user's situation and also motivational, acknowledging improvements and encouraging continued effort. Such models can also be used to respond, in real-time, to questions or queries received from users.

FIG. 4

Figure 4:
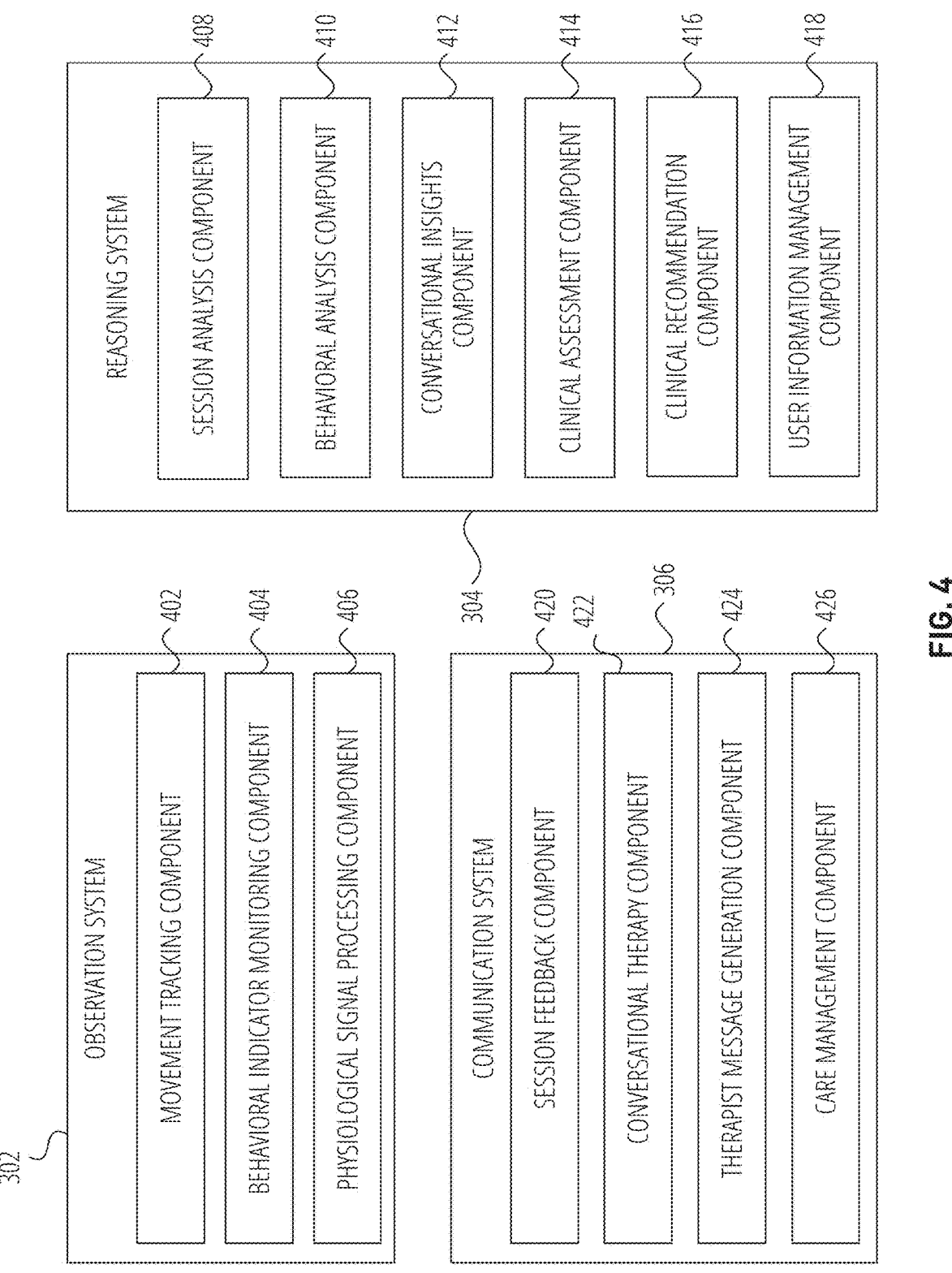
FIG. 4 is a block diagram further illustrating the systems of FIG. 3, according to some examples.

FIG. 4 further illustrates the systems of FIG. 3, according to some examples. In FIG. 3, the observation system 302 of the digital care platform 102 is shown to include a movement tracking component 402, a behavioral indicator monitoring component 404, and a physiological signal processing component 406.

The movement tracking component 402 is configured to capture and analyze user movements during sessions. The movement tracking component 402 processes input from hardware such as cameras or other sensors. In some examples, the movement tracking component 402 utilizes computer vision technology to track body movements.

The behavioral indicator monitoring component 404 can monitor or detect behavioral patterns. In some examples, this behavioral indicator monitoring component 404 monitors signals from specialized sensors including wearable technology to develop insights into a user's daily functioning or adherence patterns. The behavioral indicator monitoring component 404 can collect or analyze data such as sleep patterns, activity levels, or stress indicators. In some examples, the behavioral indicator monitoring component 404 detects patterns such as periods of effective engagement with the digital care platform 102 or periods of non-engagement that indicate potential adherence issues, which may trigger clinical intervention.

The physiological signal processing component 406 operates to process biological signals collected from one or various sensors. For example, the physiological signal processing component 406 can operate to derive insights related to heart rate, heart rate variability, breathing patterns, and/or blood oxygen levels. These physiological signals may be transformed into higher-level insights such as stress levels, sleep quality, and/or recovery status. The physiological signal processing component 406 can incorporate filtering mechanisms to compensate for movement artifacts or environmental challenges that affect signal quality.

The reasoning system 304 of the digital care platform 102 is shown to include a session analysis component 408, a behavioral analysis component 410, a conversational insights component 412, a clinical assessment component 414, a clinical recommendation component 416, and a user information management component 418. The session analysis component 408 operates to evaluate sessions and extract meaningful clinical insights. In some examples, the session analysis component 408 triggered each time a user performs a new session, processing detailed session data to produce a holistic analysis stored in a database. The session analysis component 408 can use one or more machine learning models for specific therapeutic domains to interpret session data. In some examples, the session analysis component 408 identifies patterns across multiple sessions to detect trends in user performance, engagement, and clinical progress that inform subsequent decision-making.

The behavioral analysis component 410 is configured to examine activities and behavioral patterns outside structured sessions. In some examples, the behavioral analysis component 410 analyzes signals from wearable technology and application interactions to develop insights into daily functioning and adherence to recommendations. In some examples, the behavioral analysis component 410 detects correlations between environmental factors, behavioral patterns, and clinical outcomes to inform treatment adjustments. In some examples, the behavioral analysis component 410 identifies circumstances where abnormal stress levels or other physiological changes occur, such as specific days of the week, helping to generate clinically-informed behavioral recommendations.

The conversational insights component 412 operates to analyze interactions between the user and the digital care platform 102. This may include verbal and text-based interactions between the user and both AI-driven care specialists and human clinicians. In some examples, conversational insights component 412 can identify clinically or engagement-relevant information embedded within casual conversation that might not be explicitly stated. For example, the conversational insights component 412 extracts themes, concerns, and engagement indicators from communication transcripts to inform clinical assessment. In some examples, conversational insights component 412 detects subtle indicators of changing conditions or adherence challenges through linguistic analysis. For example, unlike general sentiment analyzers, the conversational insights component 412 can include one or more models specifically trained to identify patterns relevant to clinical outcomes and treatment adherence in healthcare conversations.

The clinical assessment component 414 serves as an integrative element within the reasoning system 304 that synthesizes available information into a comprehensive clinical assessment. In some examples, the clinical assessment component 414 performs holistic reasoning that mirrors or seeks to mirror a clinician's thought process when reassessing a patient. The clinical assessment component 414 can incorporate multiple data streams, including insights from the session analysis component 408, the behavioral analysis component 410, and/or the conversational insights component 412, as well as established clinical guidelines, to form a comprehensive understanding of user status.

The clinical recommendation component 416 can generate output based on the relevant clinical assessment and other relevant data. For example, the clinical recommendation component 416 communicates with other components in the reasoning system 304 and generates one of three types of outputs: a therapy recommendation (e.g., a new therapy program or modifications to an existing therapy program), behavioral recommendations (e.g., suggestions for activities outside formal therapy), or clinical escalation recommendations (e.g., for additional intervention when needed).

In some examples, the user information management component 418 maintains and organizes user data. For example, the user information management component 418 helps to securely store and manages user preferences, communication history, and engagement patterns to inform future interactions. The user information management component 418 may track which communication channels and styles have been most effective for each individual user. In some examples, the user information management component 418 provides temporal awareness for future action scheduling, such as when users request appointment changes or require follow-up communications.

Still referring to FIG. 4, the communication system 306 of the digital care platform 102 is shown to include a session feedback component 420, a conversational therapy component 422, a therapist message generation component 424, and a care management component 426. Aspects of the session feedback component 420, the conversational therapy component 422, the therapist message generation component 424, and/or the care management component 426 can be provided by the user management system 308 or the user messaging system 310 as discussed with reference to FIG. 3.

The session feedback component 420 is configured to provide real-time guidance during sessions. In some examples, the session feedback component 420 generates contextually relevant feedback based on data received from the observation system 302, including movement tracking data, physiological signals, and/or in-session feedback from the user. For physical therapy applications, the session feedback component 420 can provide visual and audio guidance through displays and speakers when exercises are performed incorrectly or compensations are detected.

The therapist message generation component 424 serves as an interface within the communication system 306 that assists supervising users in crafting effective user communications. In some examples, the therapist message generation component 424 works with clinicians in an iterative process to develop appropriate messages for users. The therapist message generation component 424 can suggest message content based on clinical patterns, user history, and communication preferences while allowing clinicians to modify suggestions before approval. In some examples, the therapist message generation component 424 analyzes previous successful communications with similar users to inform its suggestions.

The care management component 426 can be configured to handle certain administrative and operational elements of a care journey. In some examples, the care management component 426 operates across multiple communication channels including email, support chat, and/or phone calls to provide an integrated care experience. The care management component 426 may manage appointment scheduling, follow-up coordination, enrollment, and other administrative tasks. In some examples, the care management component 426 guides users through multi-step processes such as onboarding, utilizing conversational frameworks that adapt based on user responses while maintaining procedural integrity.

FIG. 5

Figure 5:
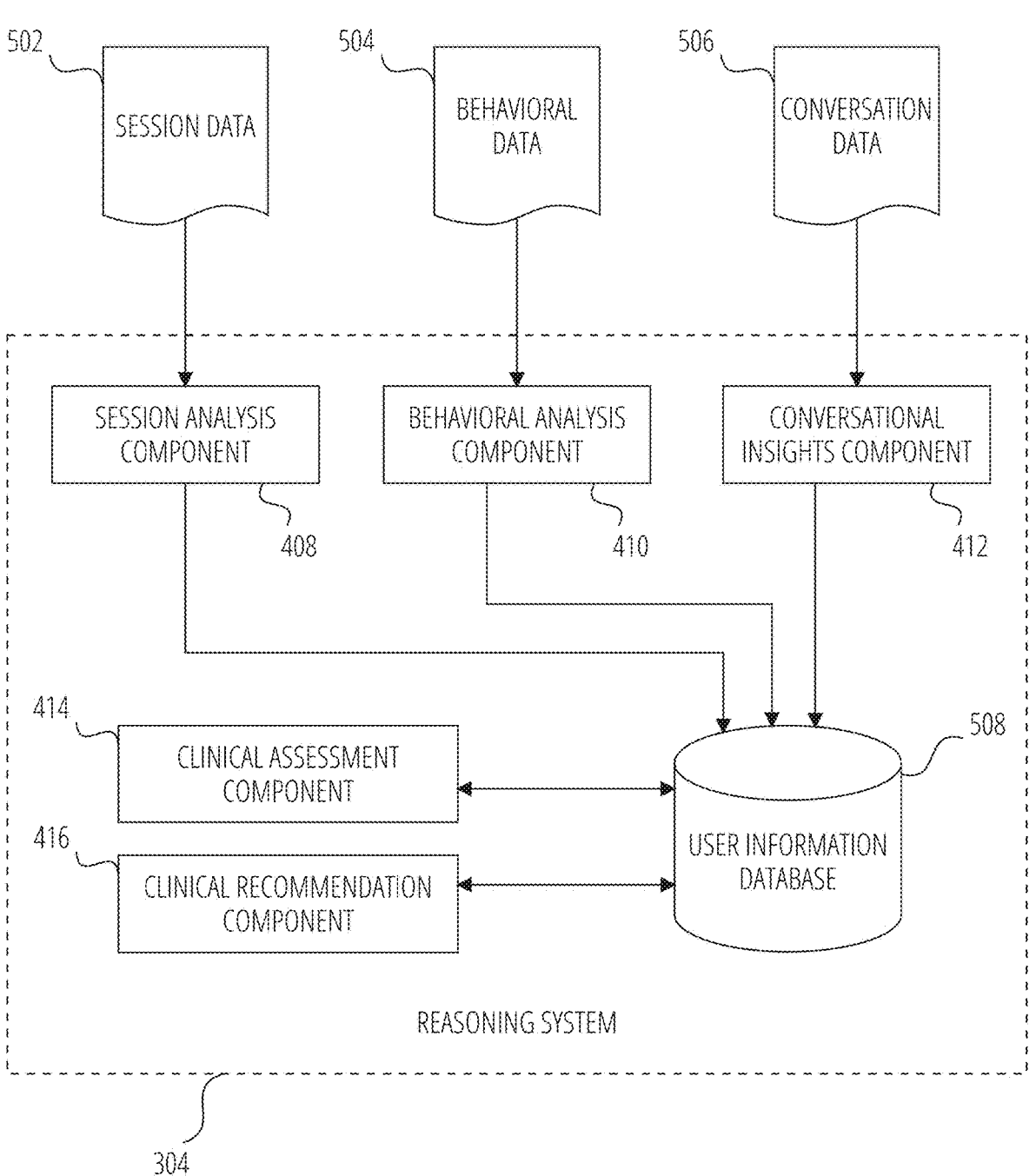
FIG. 5 is a diagrammatic illustration of operation of the reasoning system of FIG. 4, according to some examples.

FIG. 5 illustrates operation of the reasoning system 304 of FIG. 4, according to some examples. FIG. 5 shows that the reasoning system 304 receives input data including session data 502, behavioral data 504, and conversation data 506. A user information database 508 is further illustrated in FIG. 5, which may include various types of user data.

The session data 502 flows into the session analysis component 408, which evaluates sessions to extract meaningful insights. In some examples, the session analysis component 408 is triggered each time a user performs a new session, processing detailed session data to produce an analysis stored in the user information database 508.

The behavioral data 504 are directed to the behavioral analysis component 410, which examines activities and behavioral patterns outside structured therapy sessions. In some examples, the behavioral analysis component 410 detects correlations between environmental factors, behavioral patterns, and/or clinical outcomes to inform treatment adjustments. The conversation data 506 is processed by the conversational insights component 412, which analyzes verbal and/or text-based interactions, as discussed with reference to FIG. 4.

Outputs from the session analysis component 408, behavioral analysis component 410, and behavioral analysis component 410 are stored in the user information database 508, from where they are accessed by the clinical assessment component 414. The clinical assessment component 414 synthesizes available information into a comprehensive assessment.

Based on the comprehensive assessment, the clinical recommendation component 416 generates recommendation data. For example, the clinical recommendation component 416 processes the comprehensive assessment for a particular user through one or more recommender machine learning models which output recommendation data for an activity program of the user. The reasoning system 304 can analyze temporal patterns and progression trajectories.

As discussed, the recommendation data can include automatically generated exploratory program elements, which may comprise new activities, activity variations, or new activity sequences not contained in user history data. In some examples, the exploratory program elements include recommended changes in exercise order for particular tracked users.

In some examples, the user information database 508 functions as both a source of historical information consumed by the reasoning system 304 and the destination for newly generated insights or recommendations, establishing a bidirectional data flow that helps with continuous learning or personalization.

The user information database 508 may store multiple categories of data organized in a unified structure, including user tracking data, user history data, and processed versions of such data (e.g., as processed by the session analysis component 408, the behavioral analysis component 410, or the conversational insights component 412). In some examples, the user information database 508 stores pre-existing medical history from prior to enrollment in the digital care platform 102. The user information database 508 can further contain baseline assessment data captured during initial evaluation processes and subsequent reassessment data documenting changes in user status over time. Information submitted directly by users through enrollment forms can also be integrated into the information in the user information database 508.

In some examples, the user information database 508 further stores the outputs generated by the specialized components of the reasoning system 304, including therapy session analyses, behavioral tracking information, conversation histories with extracted insights, and clinical evaluations, decisions, and/or recommendations. In some examples, the user information database 508 retains supervising user notes and overrides, which document human expert judgments that modify or supplement AI-generated content.

Thus, in some examples, a continuous read-write interaction creates an evolving clinical picture that becomes increasingly comprehensive and personalized as users progress through their care journey. In some examples, the user information database 508 employs data validation protocols to provide consistency and clinical appropriateness of stored information, particularly when integrating inputs from multiple sources. Vectorized storage can be implemented to improve the speed or efficiency of access to relevant information, such as for information retrieval by the clinical assessment component 414 or the clinical recommendation component 416.

In some examples, to obtain a personalized recommendation, a base prompt structure is utilized that includes a scaffold of base data points, such as recent user data changes, areas requiring attention, and motivational triggers identified from the user's historical data. The clinical recommendation component 416 can employ programmatic techniques to embed these data points into a structured prompt such that each element is placed within the prompt in a manner that maintains a logical flow. The prompt can be input to a model such as an LLM. The model processes the prompt, analyzing the embedded data points and contextual information to understand the user's current therapeutic state and generate a personalized recommendation.

In some examples, the personalized recommendations are designed to be actionable and engaging, providing therapists with clear insights into user condition and suggested interventions. The therapist can validate and/or adapt AI-generated recommendations for clinical accuracy and/or appropriateness. In this way, a robust framework is provided for generating personalized recommendations.

In some examples, a prompt generation process is designed to create multiple types of prompts for model processing. This process includes the generation of a scenario descriptor, a system prompt, and a user prompt, each serving a specific purpose. The event descriptor can inform the model of the event that triggered the generation process. For example, the event descriptor outlines a significant occurrence or pattern within the therapy journey that requires attention. It provides a high-level overview of the event, such as lack of engagement or a notable change in condition. The event descriptor is used to inform the system prompt and user prompt by providing context for the recommendation to be generated.

The system prompt equips the model with the persona and context information related to the event described. It may instruct the model to adopt the role of an AI-powered therapy management assistant, providing clinically relevant and data-driven recommendations. The system prompt includes context such as the therapy history, compliance data, and any relevant reported outcomes. It guides the model on the tone and content of the recommendation. The system prompt may also specify the desired format or structure of the recommendation output. In some examples, the system prompt may prompt the model to generate a specific recommendation type based on a predetermined correspondence between an event and a recommendation type.

The user prompt provides detailed specifics regarding the event, including relevant or potentially relevant user data for analysis. The user prompt is designed to elicit a personalized recommendation from the model, which directly addresses therapy management needs and supports the therapist in decision-making. The recommendation may include suggestions for therapy plan adjustments, patient engagement strategies, or additional assessments required.

The table below provides non-limiting examples of an event descriptor, a system prompt, and a user prompt designed to generate personalized recommendations for therapist review.

| Event descriptor | Patient reports increased discomfort following specific exercises. |
|---|---|
| System prompt | You are an AI-powered therapy management assistant tasked with analyzing patient feedback and performance data. Analyze the data and generate a recommendation that addresses the patient's reported discomfort and suggests alternatives that may alleviate the issue. If your recommendation involves changing an exercise, specify the exercise to be replaced and the proposed alternative. |
| User prompt | Patient ID 12345 has reported increased discomfort following the completion of "Weighted Lunges." The patient has a history of knee sensitivity, and recent session data indicates a spike in reported pain levels post-exercise. Review the patient's history and generate a recommendation for the therapist to modify the patient's exercise program. |

-continued

|  |  |
|---|---|
|  | Patient history data: |
|  | Exercise completion data: [ . . . ] |
|  | Pain levels: [ . . . ] |
|  | Sensitivity data: [ . . . ] |
| Example of | Proposed change: |
| LLM-generated | Switch "Weighted Lunges" with "Static Wall Sits" for subsequent |
| response | sessions. |
|  | Reasons: |
|  | Based on Patient ID 12345's feedback and history of knee sensitivity, it is |
|  | recommended to replace the "Weighted Lunges" exercise with "Static |
|  | Wall Sits." This alternative exercise is designed to strengthen the same |
|  | muscle groups while minimizing the strain on the knees. It is important to |
|  | ensure that the patient's discomfort is addressed to prevent potential |
|  | injury and to maintain engagement with the therapy program. |

In the example table, once the LLM returns the example output, the personalized recommendation (change to activity program) can be presented to the therapist for approval, together with the LLM's additional comments (reasons for the recommendation). This allows the therapist to easily review, edit, and approve or reject the personalized recommendation. This also saves the therapist time in that less information review is needed.

FIG. 6

Figure 6:
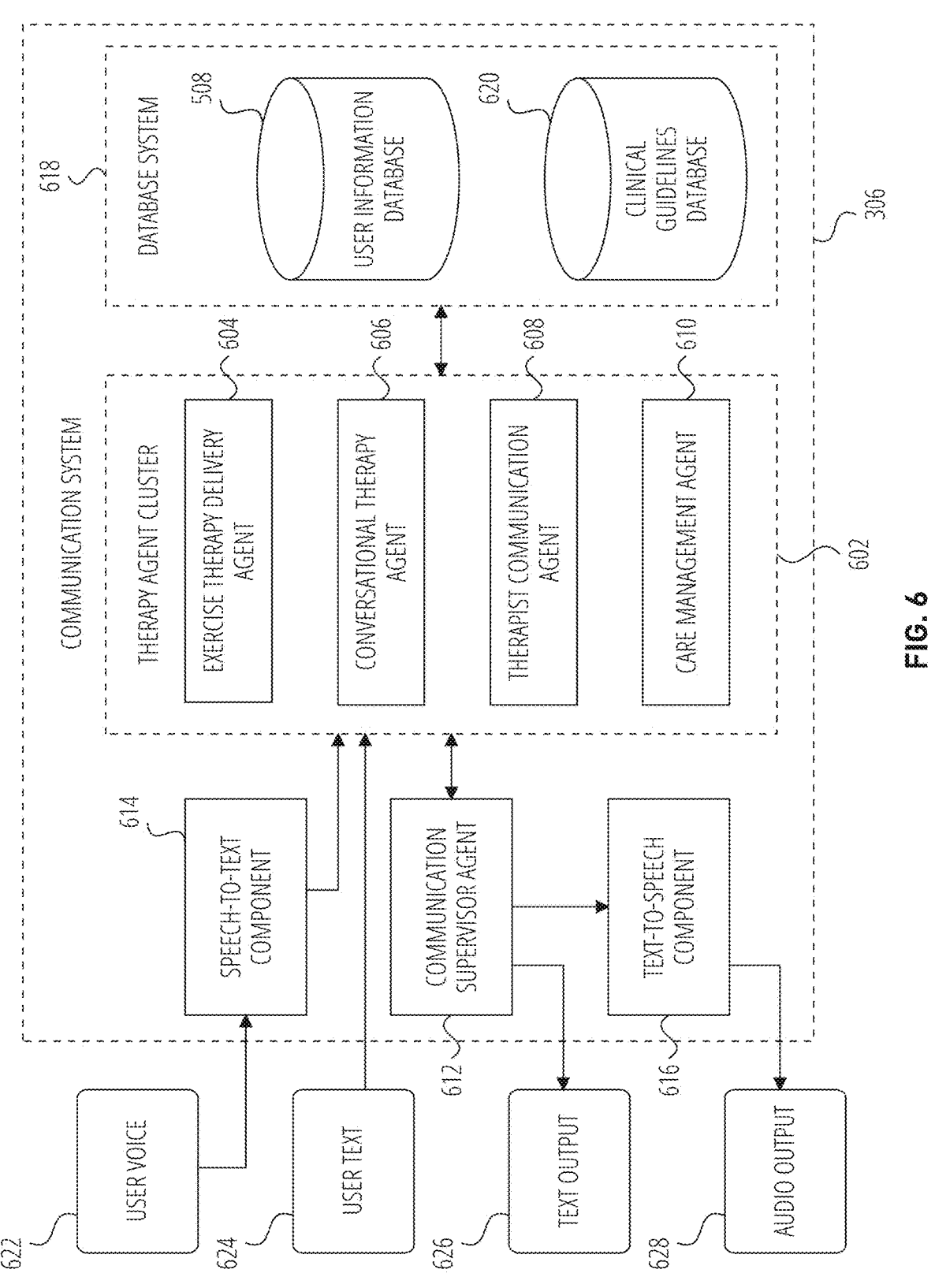
FIG. 6 is a diagrammatic illustration of operation of the communication system of FIG. 4, according to some examples.

FIG. 6 illustrates operation of the communication system 306 of FIG. 4, according to some examples. The communication system 306 operates to execute a therapy agent cluster 602. Specifically, in FIG. 6, the therapy agent cluster 602 operates to implement various AI agents: the session feedback component 420 is implemented via an exercise therapy delivery agent 604, the conversational therapy component 422 is implemented via a conversational therapy agent 606, the therapist message generation component 424 is implemented via a therapist communication agent 608, and the care management component 426 is implemented via a care management agent 610.

The communication system 306 of FIG. 6 further executes a communication supervisor agent 612, a speech-to-text component 614, and a text-to-speech component 616, and includes a database system 618 providing access to the user information database 508 and a clinical guidelines database 620. In some examples, the user information database 508 and the clinical guidelines database 620 are provided as vector databases that are accessible to the various AI agents in the therapy agent cluster 602 on demand, while the communication supervisor agent 612 monitors interactions and controls which outputs are passed on to users of the digital care platform 102.

In some examples, the communication system 306 implements a state machine orchestration approach. Rather than allowing agents to navigate entire clinical protocols independently, complex procedures are decomposed into discrete states with well-defined transitions. The communication system 306 maintains awareness of the current state and valid transitions while machine learning models handle natural language understanding and generation within that context.

However, naive implementations of state machines can create unnatural interactions where agents rigidly follow predefined steps regardless of context. For example, an AI agent may ask the user a question that was already addressed in a prior step. This technical challenge is addressed, in some examples, by embedding state awareness directly into model training, for example, by training agents to maintain procedural integrity while recognizing and incorporating information that users volunteer out of sequence. This approach can help the communication system 306 to skip unnecessary steps, acknowledge previously provided information, and adapt the conversation flow dynamically without sacrificing protocol adherence.

Turning now specifically to the AI agents in the therapy agent cluster 602, the exercise therapy delivery agent 604 functions as a foundation for asynchronous exercise therapy sessions, serving as a clinically knowledgeable companion throughout rehabilitation activities. The exercise therapy delivery agent 604 interfaces with the observation system 302, receiving real-time tracking data, exercise performance metrics, and/or user feedback. This allows the exercise therapy delivery agent 604 to generate immediate, contextually relevant feedback and adjustments while collecting clinically significant information for subsequent clinician review.

The conversational therapy agent 606 is configured for dialogue-based interventions, such as mental health therapies including guided meditation, structured journaling, and/or cognitive behavioral therapy protocols. The conversational therapy agent 606 maintains both appropriate communication style and procedural integrity through state machine orchestration.

In some examples, the therapist communication agent 608 works with a therapist in an iterative process to develop appropriate messages for users. The care management agent 610 manages administrative and operational elements of the care journey, operating across multiple communication channels, as discussed with reference to FIG. 4. The communication supervisor agent 612 reviews communications produced by other agents, evaluating safety and factual accuracy of content before it reaches users. In some examples, after generating a response but before presenting it to the user, agents submit their proposed communication along with identifiers of specific articles from databases used as reference sources to the communication supervisor agent 612, with the communication supervisor agent 612 acting as a gatekeeper or quality control component.

During operation, and as shown in FIG. 6, the communication system 306 receives input through user voice 622 and/or user text 624. Voice inputs are processed by the speech-to-text component 614 before reaching the therapy agent cluster 602. After processing by the therapy agent cluster 602, outputs are generated as text output 626 or converted to audio output 628 via the text-to-speech component 616.

The user information database 508 stores user data, while the clinical guidelines database 620 stores approved clinical information, such as approved exercises, self-care recommendations, and/or guidance in numerous articles. This enables the various AI agents to retrieve relevant information in real-time without the need to "memorize" extensive clinical knowledge within model parameters.

FIG. 7

Figure 7:
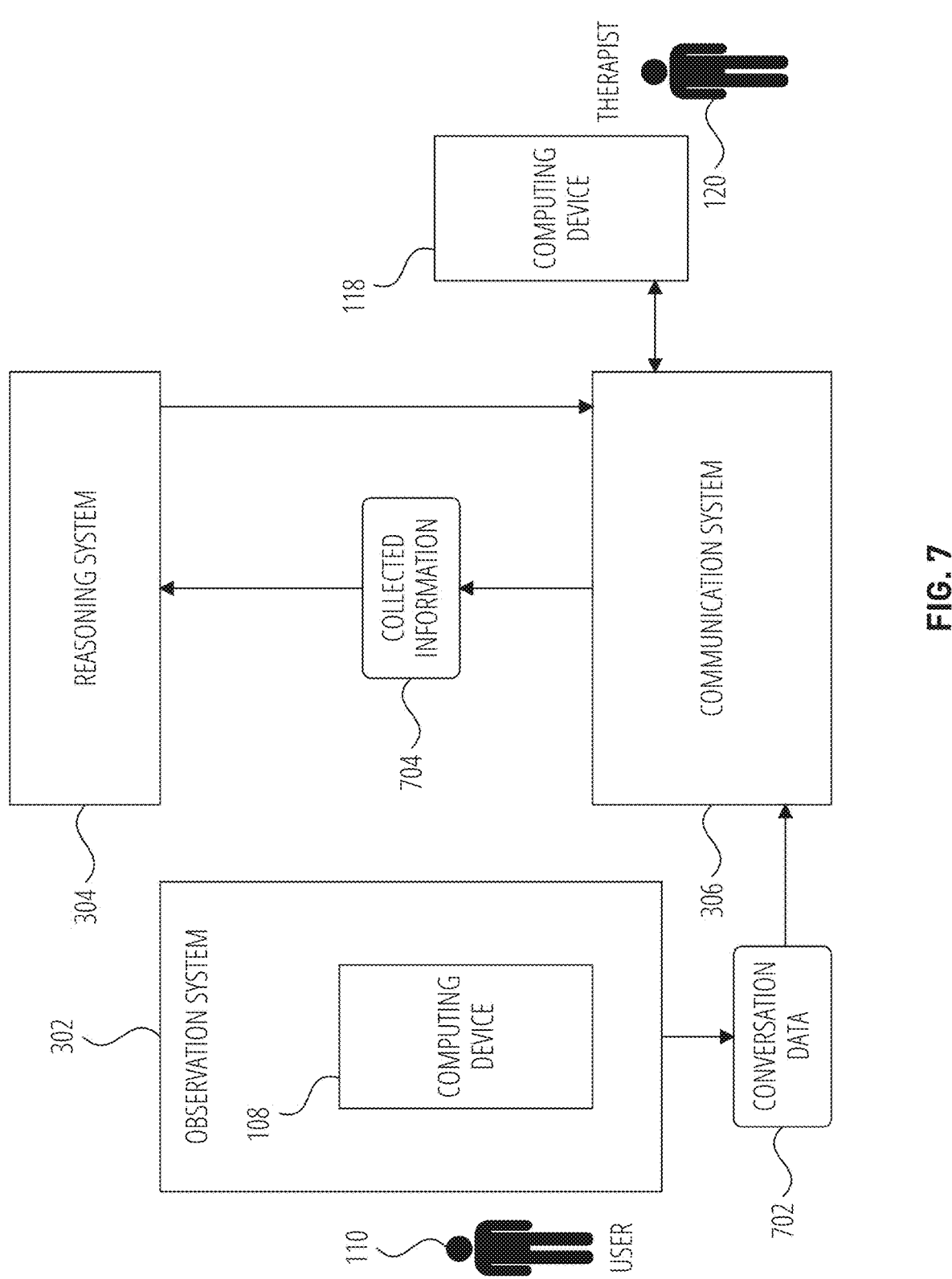
FIG. 7 is a diagrammatic illustration of operation of a digital care platform, according to some examples.

FIG. 7 depicts interactions between the observation system 302, the reasoning system 304, and the communication system 306, according to some examples. These interactions can, for example, take place during user onboarding and/or during ongoing clinical communication.

The observation system 302 captures and processes conversation data 702 from the computing device 108 associated with the user 110 based on interactions between the user 110 and the digital care platform 102. This allows the communication system 306 to process the conversation data 702 into collected information 704, and to relay the collected information 704 to the reasoning system 304 for processing.

In some examples, the observation system 302 and/or communication system 306 work together to receive communications from a prospective user. The communication system 306 can generate communications to explain a therapy approach, address questions about the treatment process, and guide the user 110 through interdependent assessment questions. The communication system 306 may execute conversational protocols designed as multi-step sequences with branching logic that adapts based on user responses while maintaining the ability to handle open-ended inquiries.

In some examples, the system captures user responses to clinical assessment questions, processes this information through the reasoning system 304, and presents relevant insights to the therapist 120 via the computing device 118 of the therapist 120. The therapist 120 may then provide input, make clinical decisions, or approve AI-generated recommendations via computing device 118. In some examples, after or during onboarding, the reasoning system 304 generates an initial prescription suggestion for therapist review. In some examples, the reasoning system 304 analyzes the collected information 704 to identify patterns and make personalized care recommendations based on the specific needs and characteristics of the user 110.

FIG. 8

Figure 8:
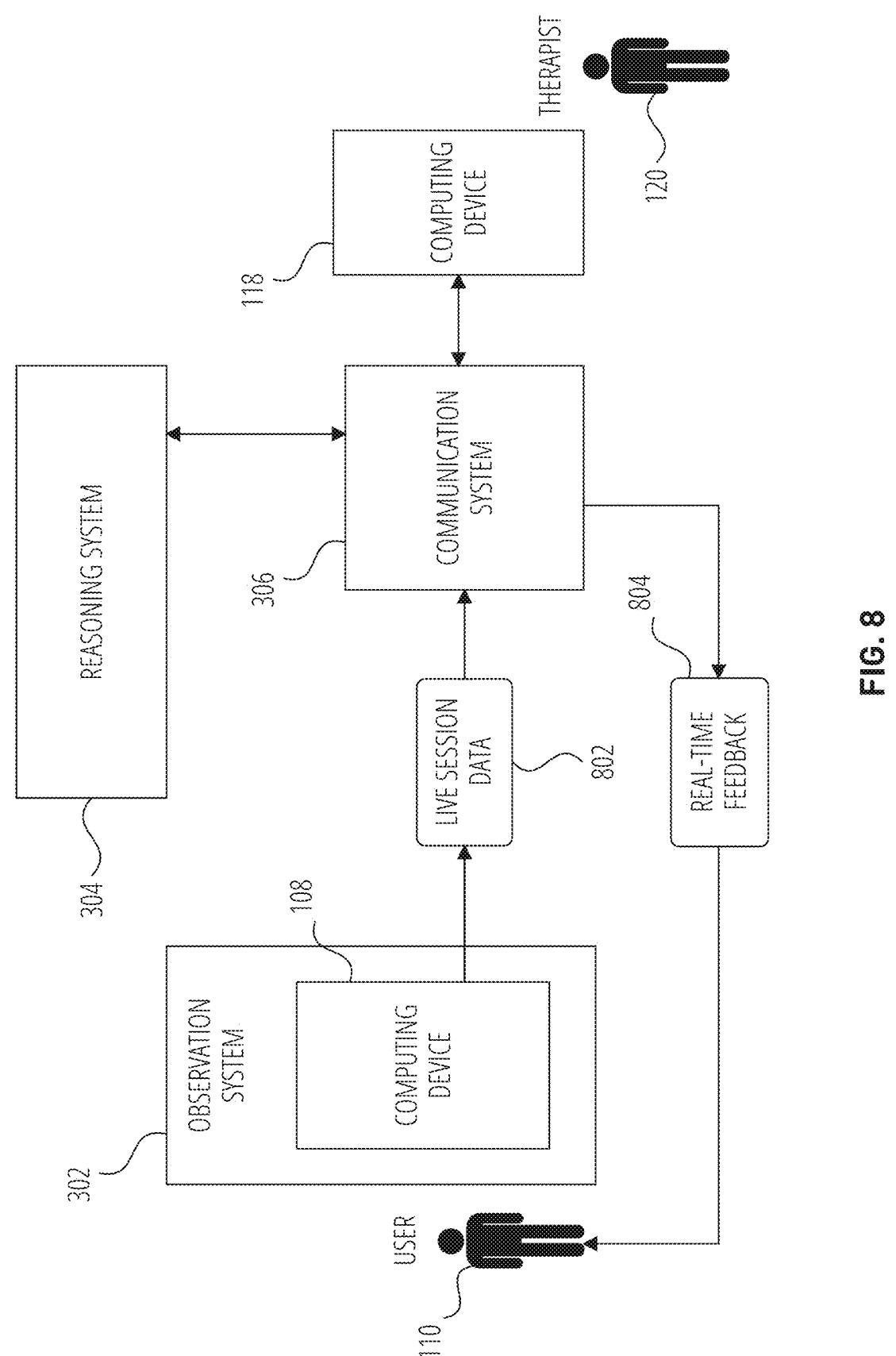
FIG. 8 is a further diagrammatic illustration of operation of a digital care platform, according to some examples.

FIG. 8 depicts further interactions between the observation system 302, the reasoning system 304, and the communication system 306, according to some examples. These interactions can, for example, take place during a session that forms part of an activity program assigned to the user 110 to provide continuous feedback to the user 110 during the session.

The observation system 302 captures and processes real-time data related to how the user is performing during the session. This data is shown as live session data 802 in FIG. 8. For example, the cameras 202 of the computing device 108 are used to capture images, with computer vision techniques being applied by the observation system 302 to generate the live session data 802.

The live session data 802 flows from the observation system 302 to the communication system 306, which relays the live session data 802 to the reasoning system 304 for analysis. For example, the reasoning system 304 executes one or more user interaction machine learning models with the context of the user's clinical history and treatment protocol, and generates recommendations for feedback or specific messages.

The communication system 306 receives input from the reasoning system 304 and generates real-time feedback 804 based thereon, that is delivered to the user 110 (e.g., via the computing device 108). The real-time feedback 804 may include contextually relevant guidance, exercise corrections, encouragement, or instructions based on the user's current performance as detected by the observation system 302 and analyzed by the reasoning system 304. The real-time feedback 804 can also include dynamic adjustments to the activity program itself (e.g., adjusting exercises if the user 110 is having difficulty).

The communication system 306 also connects to the computing device 118 associated with the therapist 120, enabling therapist oversight of the session where needed. In some examples, this maintains a human-in-the-loop architecture while allowing for automated session delivery.

FIG. 9

Figure 9:
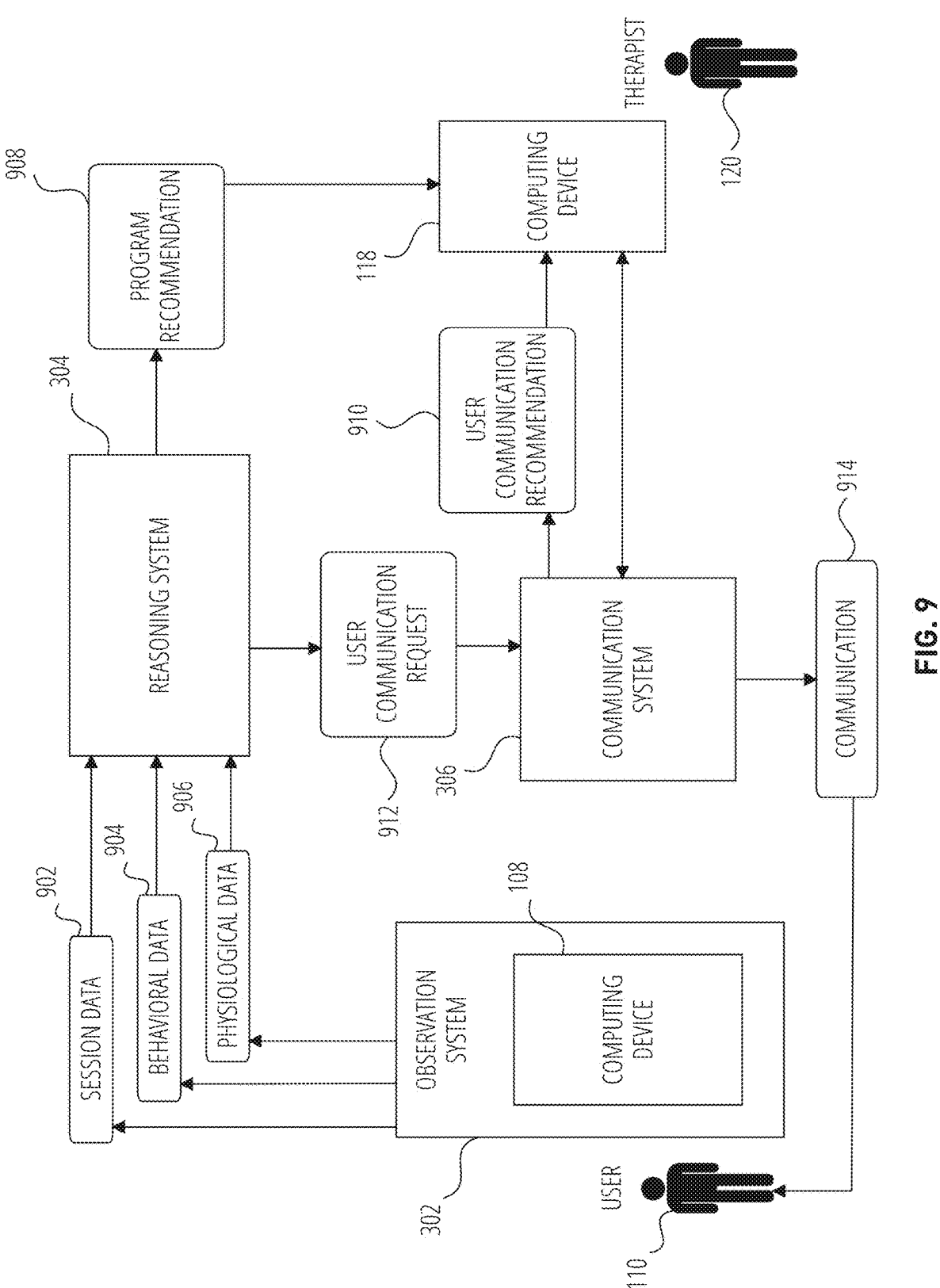
FIG. 9 is a further diagrammatic illustration of operation of a digital care platform, according to some examples.

FIG. 9 depicts further interactions between the observation system 302, the reasoning system 304, and the communication system 306, according to some examples. These interactions can, for example, take place when the observation system 302 collects user data or when another event triggers the generation of recommendation data by the reasoning system 304. FIG. 9 depicts a human-in-the-loop approach in which the therapist 120 validates recommendations generated by the reasoning system 304 or the communication system 306 before implementation.

The observation system 302 continuously collects relevant data from multiple sources connected to or associated with the computing device 108 of the user 110. In some examples, the observation system 302 receives session data 902, behavioral data 904, and physiological data 906 from sensors or other data collection mechanisms associated with the computing device 108. For example, the session data 902 includes data captured during sessions, the behavioral data 904 comprises information about activities performed outside structured sessions, and the physiological data 906 includes biological signals indicative of physical state.

The collected data items are automatically transmitted to the reasoning system 304, which processes the information through a multi-layered analysis pipeline. In some examples, the reasoning system 304 transforms raw data into specific program suggestions or adjustments as well as suggested user communications.

For example, the reasoning system 304 generates a program recommendation 908 based on its analysis of the user data. A program recommendation can include a suggested program provided as a starting point to a user, e.g., a first or initial prescription. A program recommendation can also include an adjustment to an existing program of a user. For example, program adjustment communications can include modifications to an activity program itself, such as exercise progression, session frequency changes, or intensity adjustments. The program recommendation 908 is transmitted to the computing device 118 of the therapist 120 for validation (e.g., approval, denial, or approval with adjustments).

When the reasoning system 304 determines communication with the user 110 is needed, the reasoning system 304 activates the communication system 306 by transmitting a user communication request 912. The communication system 306 then formulates a communication strategy. In some examples, the communication system 306 processes the user communication request 912 and generates a user communication recommendation 910 that is transmitted to the computing device 118 associated with the therapist 120.

Both types of communications are generated by the digital care platform 102 in an automated fashion but clinician review and approval are obtained before implementation. In some examples, recommendation data such as the user communication recommendation 910 or the program recommendation 908 are presented to the therapist 120 along with supporting data and clinical rationale.

In some examples, the therapist 120 reviews these recommendations and provides input via the computing device 118. After validation, the communication system 306 generates a communication 914 that is delivered to the user 110 via the computing device 108. The communication 914 can contain a personalized message associated with the user communication recommendation 910, or can communicate adjustments as implemented via the program recommendation 908.

As an example, the observation system 302 captures movement data during exercises over multiple weeks and transmits the data as part of the session data 902 to the reasoning system 304. The reasoning system 304 analyzes the session data 902 (e.g., by processing the session data 902 together with other user context using a trained model) and identifies a pattern: the user 110 consistently shows decreased range of motion and increased compensation behaviors during knee exercises when performed after high-intensity upper body exercises within the same session. The reasoning system 304 also detects that exercises performed in morning sessions consistently show better form quality and reduced compensatory movements compared to evening sessions. Based on this comprehensive analysis, the reasoning system 304 suggests reordering the sequence of exercises within each session, positioning knee rehabilitation exercises before upper body strengthening work (even though, for example, the standard activity program for this user profile does not contain this activity sequence). Additionally, the reasoning system 304 recommends shifting more challenging knee exercises to morning sessions, reserving simpler maintenance exercises for evening sessions when fatigue is more likely to impact performance. These recommendations form part of the program recommendation 908.

Simultaneously or shortly thereafter, the communication system 306 is triggered to generate the user communication recommendation 910 in the form of a recommended personalized message explaining the clinical importance of this program modification: "Based on your exercise data from the past three weeks, I've noticed your knee exercises show better form when performed earlier in your sessions and during morning hours. To optimize your recovery, I've adjusted your program to schedule knee rehabilitation exercises before upper body work and placed your more challenging knee exercises in your morning sessions. This sequencing helps ensure proper form during your most critical exercises when your muscles are fresh, potentially reducing compensatory movements that could slow your progress." The therapist 120 reviews both the program recommendation 908 and the user communication recommendation 910 with their supporting data (e.g., showing comparative movement quality metrics across different session times and exercise sequences). After confirming the pattern in the movement data, the therapist 120 approves both components for implementation, enabling this personalized optimization of the user's activity program.

As another example, the observation system 302 captures physiological data through a wearable device over multiple days and transmits the data as part of the physiological data 906 to the reasoning system 304. The reasoning system 304 analyzes the physiological data 906 (e.g., by processing the data together with other user context using a trained model) and identifies a pattern: the user 110 consistently shows elevated stress levels during specific days of the week at similar times. The reasoning system 304 also detects that stress indicators appear to be significantly more pronounced during "low activity" days or "low activity" periods (e.g., days or parts thereof where the number of measured steps was below a minimum threshold or days or parts thereof where no physical activities were logged or captured). Based on this comprehensive analysis, the reasoning system 304 suggests incorporating breathing and mindfulness exercises on those specific days, scheduled proactively before the times when stress peaks typically occur (even though, for example, a standard or default mental health program for this user profile does not contain this preventative approach). Additionally, the reasoning system 304 recommends increasing activity, such as taking more steps, on days or parts of days (e.g., mornings or early evenings) that historically show higher stress patterns. These recommendations form part of the program recommendation 908.

Simultaneously or shortly thereafter, the communication system 306 is triggered to generate the user communication recommendation 910 in the form of a recommended personalized message explaining the clinical importance of this program modification: "Based on your data from the past two weeks, I've noticed your stress levels tend to increase during specific periods, particularly when you've been less active. To help manage this pattern, I've added breathing and mindfulness exercises to your program, scheduled before the times when stress typically peaks. These proactive practices can help regulate your nervous system before stress escalates, while increasing your activity levels can positively impact your mood and stress regulation pathways." The therapist 120 reviews both the program recommendation 908 and the user communication recommendation 910 with their supporting data (e.g., showing comparative stress metrics across different days and times). After confirming the pattern in the measured data, the therapist 120 approves both components for implementation, enabling this personalized optimization of the user's mental health program (which may be a separate activity program or part of a larger activity program that also includes physical exercises).

FIG. 10

Figure 10:
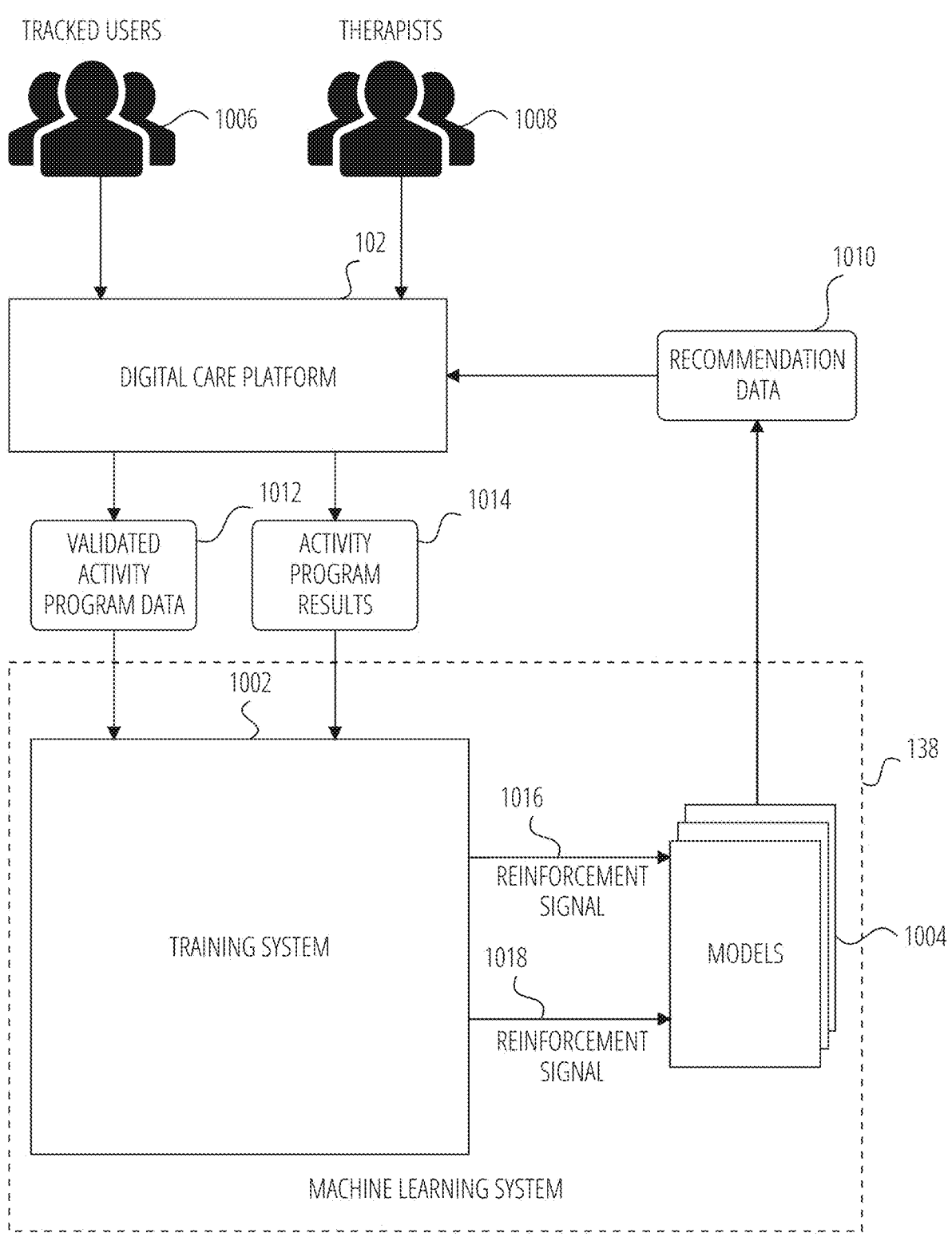
FIG. 10 is a diagrammatic illustration of machine learning operations performed using a training system associated with a digital care platform, according to some examples.

FIG. 10 shows machine learning operations performed using a training system 1002 of the machine learning system 138 of FIG. 1 to update models 1004 leveraged by the digital care platform 102, according to some examples.

In some examples, the training system 1002 implements a three-layer architecture that enables continuous system evolution beyond initial training parameters. In a first layer, an analysis of aggregated historical clinical decisions and interactions is performed, extracting patterns and relationships from clinician expertise at a scale. In a second layer, the training system 1002 continuously incorporates new clinician-approved decisions into an evolving knowledge base. Where relevant, the training system 1002 uses clinician-approved decisions and corresponding measured outcomes to create an ongoing refinement cycle. In a third layer, the training system 1002 enables the models 1004 to safely explore treatment variations within clinician-validated boundaries.

FIG. 10 illustrates tracked users 1006 and therapists 1008 interacting with the digital care platform 102 of FIG. 1, which is communicatively coupled to the training system 1002 and to the models 1004. During operation, the digital care platform 102 uses the models 1004 to generate recommendation data 1010. The recommendation data 1010 can include suggestions for various activity program elements, such as the program recommendation 908 or the user communication recommendation 910 described with reference to FIG. 9.

In some examples, the recommendation data 1010 includes automatically generated exploratory program elements, which may include new activities, activity variations, or new activity sequences. These exploratory recommendations are not immediately delivered to the tracked users 1006 but are first presented to respective ones of the therapists 1008 for review.

The digital care platform 102 produces two outputs that feed into the machine learning system 138: validated activity program data 1012 and activity program results 1014. The validated activity program data 1012 can include therapist-approved AI recommendations, therapist-adjusted AI recommendations, or details of programs that include at least one such data AI-generated or AI-assisted item associated with one of the models 1004. In some examples, the validated activity program data 1012 sent to the training system 1002 can include an indication of an original AI-generated recommendation and how it was modified or adjusted based on supervising user input as part of the validation process.

The activity program results 1014 include data about actual outcomes or results. The activity program results 1014 can include performance metrics from implemented therapy programs. In some examples, the activity program results 1014 can include tracking data showing biomechanical measurements and form analysis during activity sessions; performance metrics measuring range of motion, completion rates of exercises, and/or movement accuracy; physiological data from sensors tracking vital signs and biological signals; behavioral patterns showing program adherence and engagement levels; and/or progress evaluation data measuring whether users met specific therapeutic goals or milestones in their recovery journey.

In some examples, the validated activity program data 1012 and the activity program results 1014 are fed into the training system 1002 and function as paired data. For example, a pair can include a clinician-approved recommendation or decision and its corresponding activity program result. The training system 1002 can thus leverage this dual feedback approach to continuously refine its understanding of which therapeutic approaches work best. The dual-input reinforcement learning mechanism is illustrated through a reinforcement signal 1016 and a reinforcement signal 1018 flowing into the models 1004, as depicted in FIG. 10. For example, the reinforcement signal 1016 seeks to account for clinical appropriateness or clinical safety through therapist-approved inputs and the reinforcement signal 1018 seeks to account for clinical effectiveness through measured outcomes.

Thus, where one or more of the models 1004 generate suggestions with variations in clinical management or engagement strategies to identify new patterns that contribute to improved clinical outcomes, the feedback on those suggestions, as provided by the therapists 1008, will influence the future adjustment of model parameters by the training system 1002. This can allow the training system 1002 to incrementally improve the models 1004 while allowing safety to explore due to the "human-in-the-loop" framework provided by the therapists 1008.

The models 1004 can include one or more types of machine learning models that are used to generate the recommendation data 1010. In some examples, a machine learning model is in the form of a transformer-based language model. The architecture of the language model may include a multi-layer transformer with self-attention mechanisms, designed for sequence modeling and context-aware inference. For instance, the model may include multiple transformer blocks (e.g., twelve) with multi-head attention and feed-forward layers, optimized for handling long-term dependencies in user input data.

The language model can initially be trained using supervised or self-supervised learning (e.g., on a base training data set), depending on the nature of the training objective. For supervised tasks, training involves minimizing a function when predicting target labels. In self-supervised configurations, masked language modeling (MLM) or next-sentence prediction (NSP) objectives may be used. The training process utilizes stochastic gradient descent or variants such as Adam optimizer, with hyperparameters including a learning rate of 3e-5, weight decay, and gradient clipping for stability.

In some examples, training data for the model is drawn from a combination of publicly available corpora and proprietary datasets specific to digital health interactions. These datasets may include anonymized user logs, in-app chat transcripts, behavioral assessments, and usage patterns. For example, the training corpus may include millions of text sequences reflecting diverse user intents and contextual scenarios, enriched with domain-specific ontologies related to healthcare and wellness. In some examples, training data includes therapist-approved recommendations and program elements, such as initial program prescriptions (e.g., 300,000-500,000 samples) with baseline exercise plans; prescription adjustments throughout therapy programs (e.g., 1-5 million samples) showing how treatments were modified over time; clinical assessment notes and updates (e.g., 500,000-700,000 samples) documenting patient progress; messages sent to users (e.g., 10-20 million samples) for engagement and instruction; transcripts from cognitive behavioral therapy sessions, guided meditation sessions, and/or journaling sessions.

Input to the transformer model may consist of structured and unstructured data elements, including free-text messages, survey responses, interaction timestamps, and usage logs. Preprocessing steps may involve tokenization using subword units (e.g., WordPiece or Byte-Pair Encoding), positional encoding, and normalization of structured fields. Categorical variables may be embedded and concatenated with text-based representations to form unified input sequences.

The model output may include ranked lists of recommended actions, generated text messages, or predicted user engagements. In some examples, a recommendation decoder module interprets latent representations from the transformer to produce actionable outputs, using techniques such as beam search for message generation or softmax classification for discrete action selection. Outputs can be postprocessed to ensure alignment with clinical guidelines, relevance filters, or personalization rules.

Model parameters may be selected and optimized using hyperparameter tuning methods, such as random search or Bayesian optimization. Parameters can include the number of attention heads, hidden layer size, dropout rate, and maximum input sequence length. For example, the model may use 8 attention heads, 768-dimensional embeddings, and a maximum input length of 512 tokens to balance accuracy and computational efficiency.

In some examples, data quality and integrity are maintained through preprocessing checks and validation routines. This may include filtering out incomplete records, normalizing text input, and enforcing schema constraints. Outlier detection techniques, such as isolation forests or embedding-based distance thresholds, may be used to identify and exclude anomalous interaction patterns.

To support deployment in real-time or resource-constrained environments, the model may be compressed using techniques such as knowledge distillation, quantization, or model sparsification. For example, distillation may reduce a base model into a lightweight student model with 20 million parameters while retaining most of its performance. Quantization to 8-bit integers may further reduce memory usage and inference latency.

Deployment considerations include ensuring compatibility with mobile platforms, privacy requirements, and inference speed. The model can be integrated into a digital care application via a cloud API or deployed directly on user devices with appropriate optimization. Containerization technologies such as Docker or model-serving frameworks such as ONNX Runtime may be used to facilitate scalability and interoperability.

As also discussed elsewhere in the present disclosure, after initial training and once feedback has started flowing into the training system 1002 as shown in FIG. 10, the transformer-based language model may be updated to improve its performance over time.

In some examples, the transformer-based language model is updated using reinforcement learning techniques to optimize the relevance and effectiveness of the recommendations it generates. Reinforcement fine-tuning can be leveraged to optimize for outcomes. Reinforcement learning with human feedback (RLHF) may be employed, wherein human evaluators rank or score different outputs, and this feedback is used to train a reward model. The language model may be updated using a policy optimization algorithm, such as Proximal Policy Optimization (PPO), to increase the likelihood of generating higher-reward outputs. For instance, if a generated message leads to higher user engagement or reported satisfaction, or if a generated activity program adjustment leads to better treatment outcomes, the system learns to prefer similar outputs.

Thus, in reinforcement learning approaches, reward signals can be used to assign rewards to actions, which guide the model to favor behaviors that lead to better results over time. A model is therefore allowed to learn from its own choices (as validated by the therapists 1008, for example).

In some examples, where therapists approve or modify the exploratory program elements in the recommendation data 1010, the relevant model can learn which types of recommendations align with clinical expertise or appropriate. Simultaneously, as users engage with the validated programs, the activity program results 1014 provide objective measurements of which interventions actually produce the best outcomes. By processing both signals, the model can identify patterns where these multiple objectives align, while also discovering cases where outcomes suggest effective approaches that might not have been initially apparent to human experts.

In addition to reinforcement learning, or as an alternative, supervised fine-tuning may be applied to improve model performance based on curated datasets. This process can involve collecting labeled examples of input sequences and corresponding recommended outputs, such as exercises or communication templates reviewed by healthcare professionals. The model is then trained using a supervised objective, such as a cross-entropy loss, to minimize the discrepancy between its predictions and the labeled targets.

FIG. 11

Figure 11:
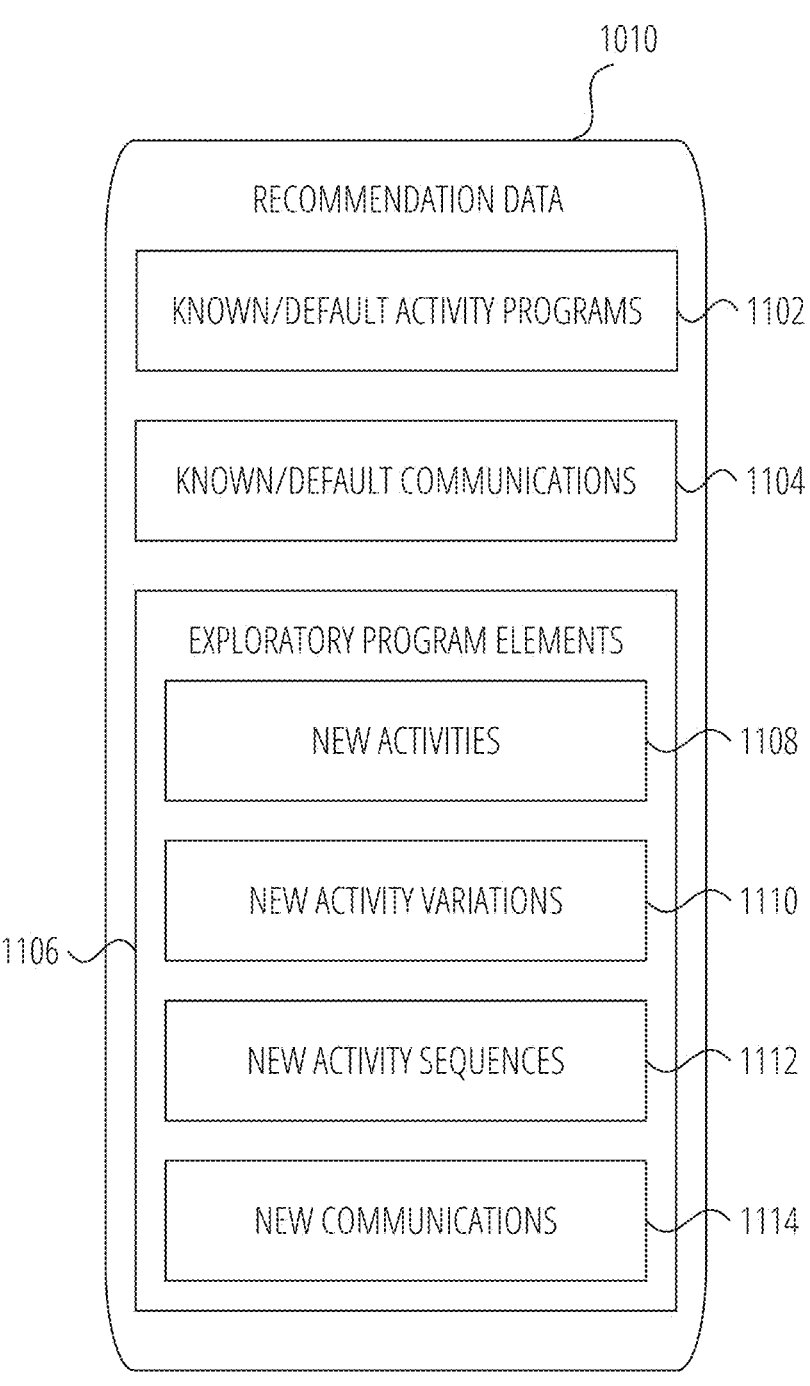
FIG. 11 is a block diagram illustrating different types of recommendation data generated by machine learning models associated with a digital care platform, according to some examples.

FIG. 11 illustrates examples of the recommendation data 1010 of FIG. 10. The recommendation data 1010 includes: known/default activity programs 1102, known/default communications 1104, and exploratory program elements 1106.

The known/default activity programs 1102 may include activities or exercise programs that have been previously validated or exist as default or template programs, for example, in the user information database 508 of the digital care platform 102. These data items may represent standard therapeutic interventions with established parameters that are already available within the digital care platform 102 for assignment to users.

The known/default communications 1104 may include standardized or previously approved messaging templates stored in the user information database 508. These communications can include predefined feedback patterns, adherence prompts, or response templates that have demonstrated effectiveness through prior use and validation within the digital care platform 102.

The exploratory program elements 1106 represent the capability of the digital care platform 102, through one or more of the models 1004 trained in the manner described in the present disclosure, to generate novel approaches beyond replicating known effective treatments or communications. Unlike the known/default elements, the exploratory program elements 1106 are newly generated, using AI, by the digital care platform 102. The exploratory program elements 1106 may include new activities 1108, new activity variations 1110, new activity sequences 1112, and/or new communications 1114.

New activities 1108 can include novel exercises or therapeutic tasks not previously included in a user's program or user history data, allowing for the introduction of entirely new therapeutic options when appropriate. New activity variations 1110 can include modifications to existing exercises or activities, such as adjustments to repetitions, intensity, duration, or execution technique, enabling fine-tuning of therapy. New activity sequences 1112 present novel ordering of existing exercises or activities, which can impact therapeutic outcomes. New communications 1114 may include novel messaging approaches or content that differ from the standard communications templates contained in the known/default communications 1104.

Exploratory program elements 1106, such as new activities 1108, new activity variations 1110, new activity sequences 1112, or new communications 1114, can be produced automatically through a controlled process implemented by the digital care platform 102. For example, the digital care platform 102 works with the machine learning system 138 to dynamically adjust a temperature parameter of the relevant machine learning model during interference time. In this way, the statistical randomness of the machine learning model's output distribution can be varied (e.g., increased) in a controlled manner.

Generally, a lower temperature (closer to 0) can make a model more deterministic and focused, while a higher temperature (closer to 1 or above) introduces more randomness and diversity, which can include a higher proportion of unexpected outputs. For instance, where a language model is utilized, when the temperature parameter is increased above baseline values (e.g., above 1), the probability distribution over the model's next-token predictions is flattened, effectively reducing the likelihood gap between high-probability and lower-probability tokens. This controlled introduction of entropy by the digital care platform 102 or the machine learning system 138 can enable the model to explore beyond the most statistically likely recommendations that would be derived from strict pattern recognition within training data.

In some examples, the digital care platform 102 implements an automated and calibrated approach where temperature values are algorithmically modulated based on factors such as the clinical domain, user adherence patterns, treatment phase, user condition, and/or the observed effectiveness of previous exploratory elements. For example, the temperature can be increased early in the treatment phase to find exploratory elements that could be effective for a particular user. As another example, higher temperature values could be applied for certain types of injuries or treatments than for others. In some examples, the exploration strategy is refined through a dual reinforcement learning framework, where both clinician validation signals and measured treatment outcomes provide feedback loops that continuously improve the exploration-exploitation balance.

The exploratory program elements 1106 may embody the "safe experimentation layer" provided by the digital care platform 102. The digital care platform 102 can discover potentially more effective approaches while maintaining safety through human oversight.

FIG. 12

Figure 12:
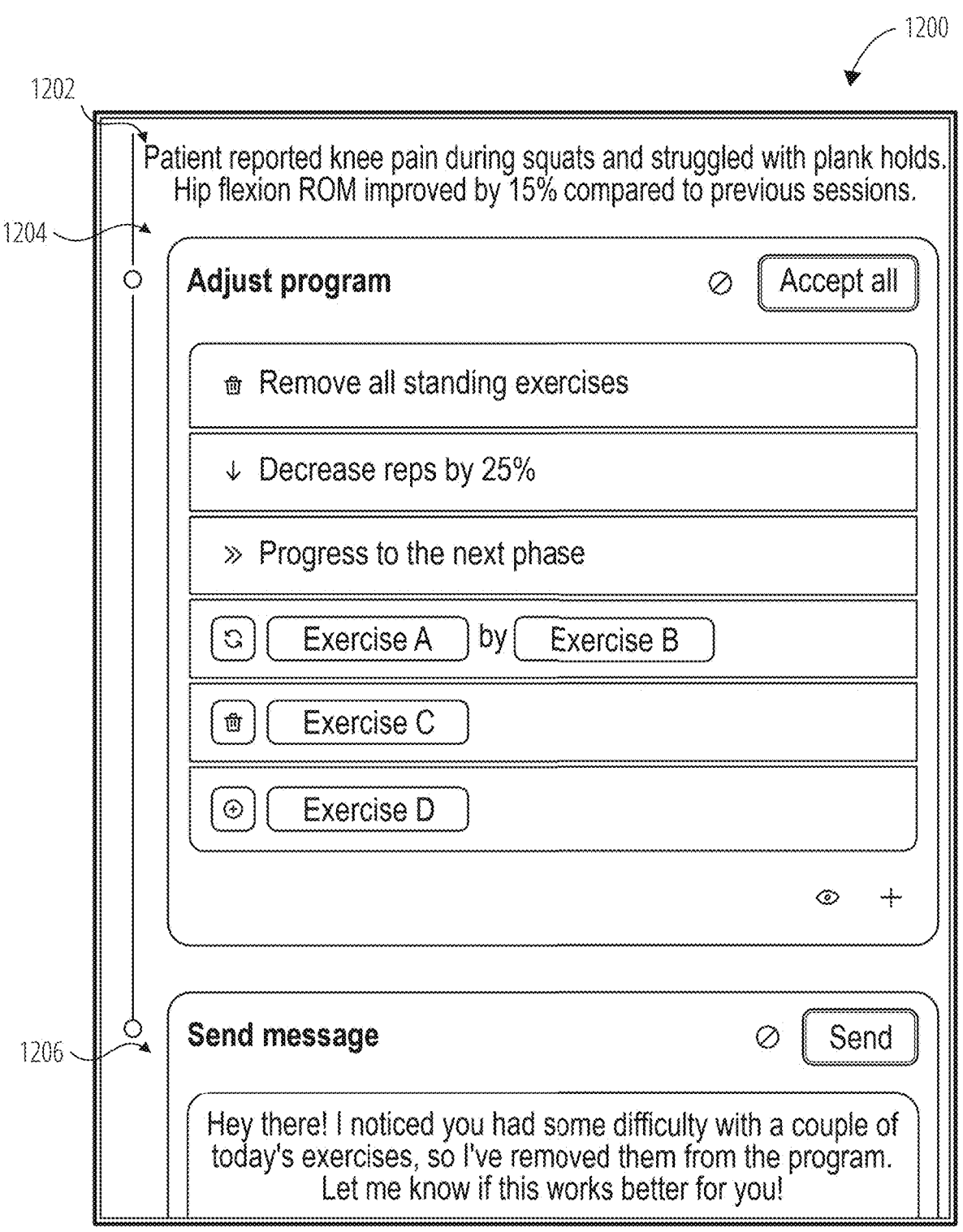
FIG. 12 is a user interface diagram illustrating a recommendation that can be automatically generated and presented in a user interface of a supervising user associated with a digital care platform, according to some examples.

FIG. 12 illustrates a recommendation report 1200 that can be automatically generated and presented in a user interface of a supervising user, according to some examples. For example, the recommendation report 1200 can be presented at the computing device 118 of the therapist 120 of FIG. 1 for validation (e.g., approval, denial, approval of some elements, or approval with certain adjustments).

The recommendation report 1200 presents a set of AI-generated suggestions for review. AI-generated feedback 1202 appears at the top of the recommendation report 1200, providing clinical context derived from patient data analysis. This section displays objective observations regarding patient performance and progress, noting "Patient reported knee pain during squats and struggled with plank holds. Hip flexion ROM (range of motion) improved by 15% compared to previous sessions." This presents the supervising user with insights that inform the subsequent recommendations (e.g., providing reasons for suggested adjustments to the activity program or for suggesting a particular message).

The recommendation report 1200 then suggests specific program adjustments in a program adjustment recommendation 1204, including removing all standing exercises, decreasing repetitions by 25%, progressing to the next phase, and modifying specific exercises (indicated as Exercise A, B, C, and D). The latter allows for specific adjustments to individual exercises including potential reordering or replacement of activities.

In addition to the program adjustment recommendation 1204, the recommendation report 1200 includes a user interaction recommendation 1206, presenting a draft message composed by the AI system (e.g., one of the models 1004) for potential communication with the user. The message "Hey there! I noticed you had some difficulty with a couple of today's exercises, so I've removed them from the program. Let me know if this works better for you!" demonstrates how the digital care platform 102 generates personalized, contextually appropriate communications that maintain a conversational tone while conveying relevant information.

The recommendation report 1200 in the interface includes action controls that allow the supervising user to efficiently review and act upon the AI-generated recommendations. The action controls include control for removing or adding exercises, an "Accept All" button for approving the complete set of recommendations, and a "Send" button for transmission of the user interaction recommendation 1206 to the user.

FIG. 13

Figure 13:
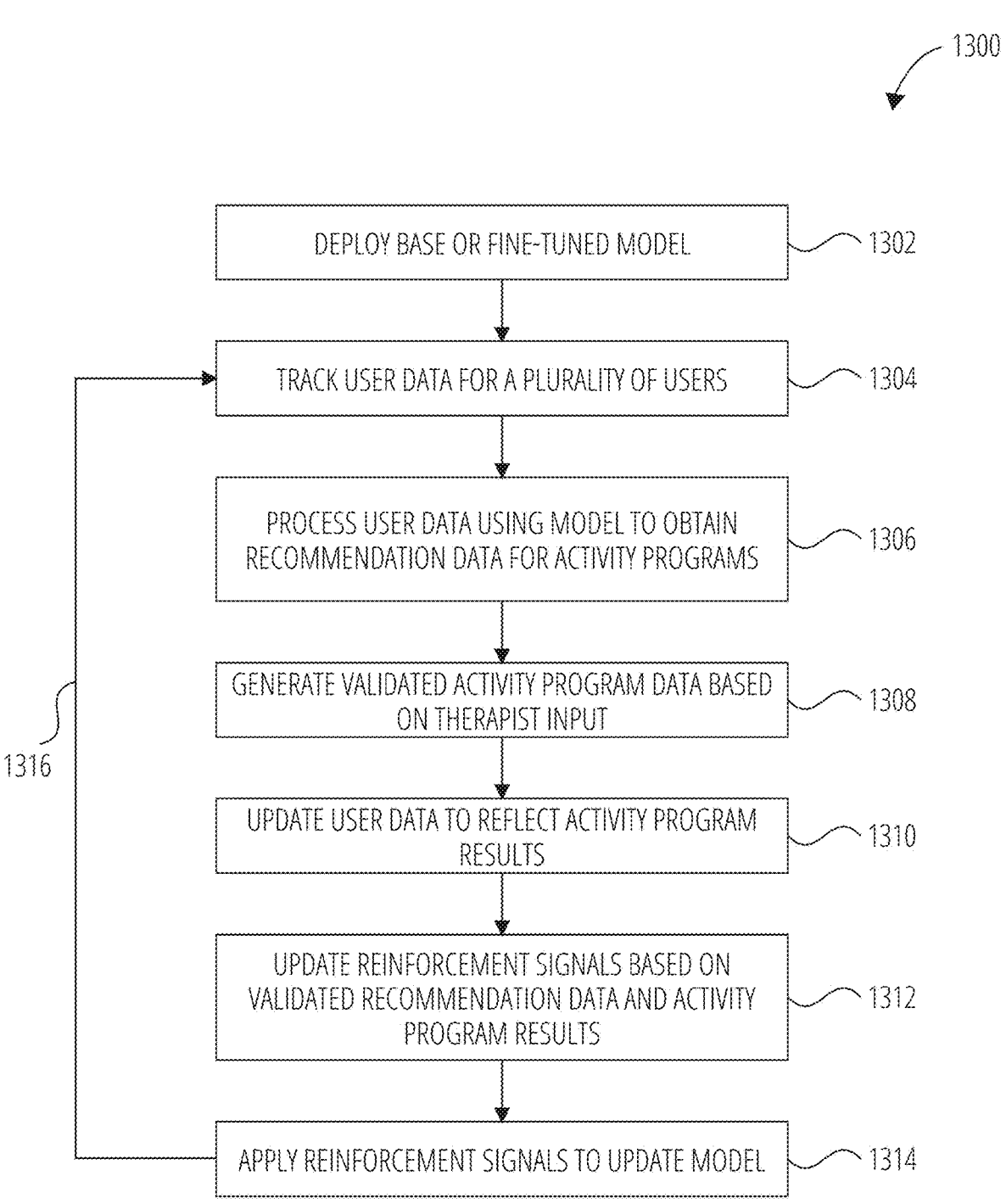
FIG. 13 is a flowchart illustrating a method of training and updating a machine learning model associated with a digital care platform, according to some examples.

FIG. 13 is a flowchart illustrating a method of training and updating a machine learning model associated with the digital care platform 102 of FIG. 1, according to some examples. The model can, for instance, be one of the models 1004 of FIG. 10 that is used to generate the recommendation data 1010.

Each block of the method 1300 comprises a computing process that may be performed using any combination of hardware, firmware, and/or software. For instance, various functions may be carried out using one or more processors executing instructions stored in one or more memories. The method may also be embodied as computer-usable instructions stored on computer storage media. The method may be provided by a standalone application, a service or hosted service (standalone or in combination with another hosted service), as a microservice via an application programming interface (API) or a plug-in to another product, to name a few.

The method 1300 starts at operation 1302, where the digital care platform 102 deploys a model into a production environment. The deployment process may include configuring the model for real-time inference based on incoming user data. In some examples, the deployment operation implements specialized hardware-software interfaces that enable the model to process inputs from the observation system 302, such as biomechanical, physiological, environmental, and/or behavioral data from users.

The deployed model can be a base model (e.g., a foundational model) or a model that has already undergone fine-tuning. As an example of the latter case, the machine learning system 138 performs initial fine-tuning of a base model using a base dataset. The base dataset can include historical clinical data such as past clinical decisions, patient interactions, and corresponding outcomes collected from therapists. In some examples, this operation utilizes supervised learning techniques to train a language model on multiple data types, including initial program prescriptions, prescription adjustments throughout therapy programs, clinical assessment notes, user messages, and/or therapy session transcripts. The model learns patterns from these historical data sources to establish baseline recommendation capabilities.

At operation 1304, the digital care platform 102 tracks user data for a plurality of users. Tracking is performed continuously by the observation system 302 that collects multi-dimensional data from users interacting with the digital care platform 102. In some examples, operation 1304 captures real-time session data through computer vision systems that monitor user movements, wearable devices that record physiological signals, and/or interaction logs that document user engagement patterns. The collected data is processed and stored in the user information database 508.

The method 1300 proceeds to operation 1306, where the digital care platform 102 processes the user data using the model to obtain recommendation data. For example, the reasoning system 304 leverages the model to generate various recommendations, tailored to each user's specific needs and progress. Although the method 1300 is described with reference to a single model, it will be appreciated that multiple models can be trained to cooperate to produce the recommendation data. In some examples, operation 1306 activates multiple specialized models in sequence, with session analyzers processing therapy session data, behavioral analyzers examining patterns outside structured sessions, and clinical recommender models integrating these inputs to generate specific recommendations.

In some examples, the method 1300 does not include the tracking operation (operation 1304) in all instances. For example, initial (e.g., baseline) user data can be processed at operation 1306 to generate a recommendation for an initial prescription, without prior tracking being needed.

At operation 1308, the digital care platform 102 generates validated activity program data based on therapist input. The recommendation data from operation 1306 can be presented to therapists through a user interface that enables review, modification, and approval of the AI-generated suggestions. In some examples, the validation operation maintains the human-in-the-loop architecture that provides a safety foundation for the digital care platform 102. The therapist input can include validation of exploratory program elements generated by the relevant model as the model seeks to explore novel activity or treatment options.

At operation 1310, the digital care platform 102 updates user data to reflect activity program results. As users engage with the validated activity programs, the digital care platform 102 records performance metrics, adherence patterns, and/or clinical outcomes. In some examples, operation 1310 integrates data from the observation system 302 that continuously monitor user progress, including movement tracking during exercises, physiological responses to activities, and/or behavioral patterns between sessions. This updated user data provides objective measurements of program effectiveness that feed back into a learning cycle, such as the learning cycle described with reference to FIG. 10.

The method 1300 proceeds to operation 1312, where the digital care platform 102 updates reinforcement signals based on both validated recommendation data and activity program results. This dual-input reinforcement mechanism combines human clinical expertise with measured outcomes to create comprehensive learning signals for the model. In some examples, a first reinforcement signal is associated with therapist approval or adjustments to AI recommendations, while a second reinforcement signal is associated with the outcomes of those recommendations.

The digital care platform 102 then applies the reinforcement signals to update the model at operation 1314. The reinforcement signals are used to modify model parameters through reinforcement learning techniques, as described in greater detail elsewhere herein. In some examples, operation 1314 implements policy optimization algorithms to adjust model weights based on the dual reinforcement signals, progressively improving the model's ability to generate effective recommendations.

The method 1300 includes a feedback loop 1316 that connects operation 1314 back to operation 1304. Thus, as the model is updated, the updated model is used to generate further recommendation data, enabling continuous learning as the digital care platform 102 processes new user data, including new outcomes. Whereas initial operations (e.g., prior to initial deployment) may include training on baseline data, the method 1300 allows the model to additionally explore potentially novel elements and sequences after initial training, with automated reinforcement learning then occurring to progressively improve the model's performance compared to the initial performance level. This continuous learning process can enable the model to discover patterns across large user populations that might not be apparent to individual clinicians, while maintaining alignment with clinical expertise through the human validation component.

FIG. 14

Figure 14:
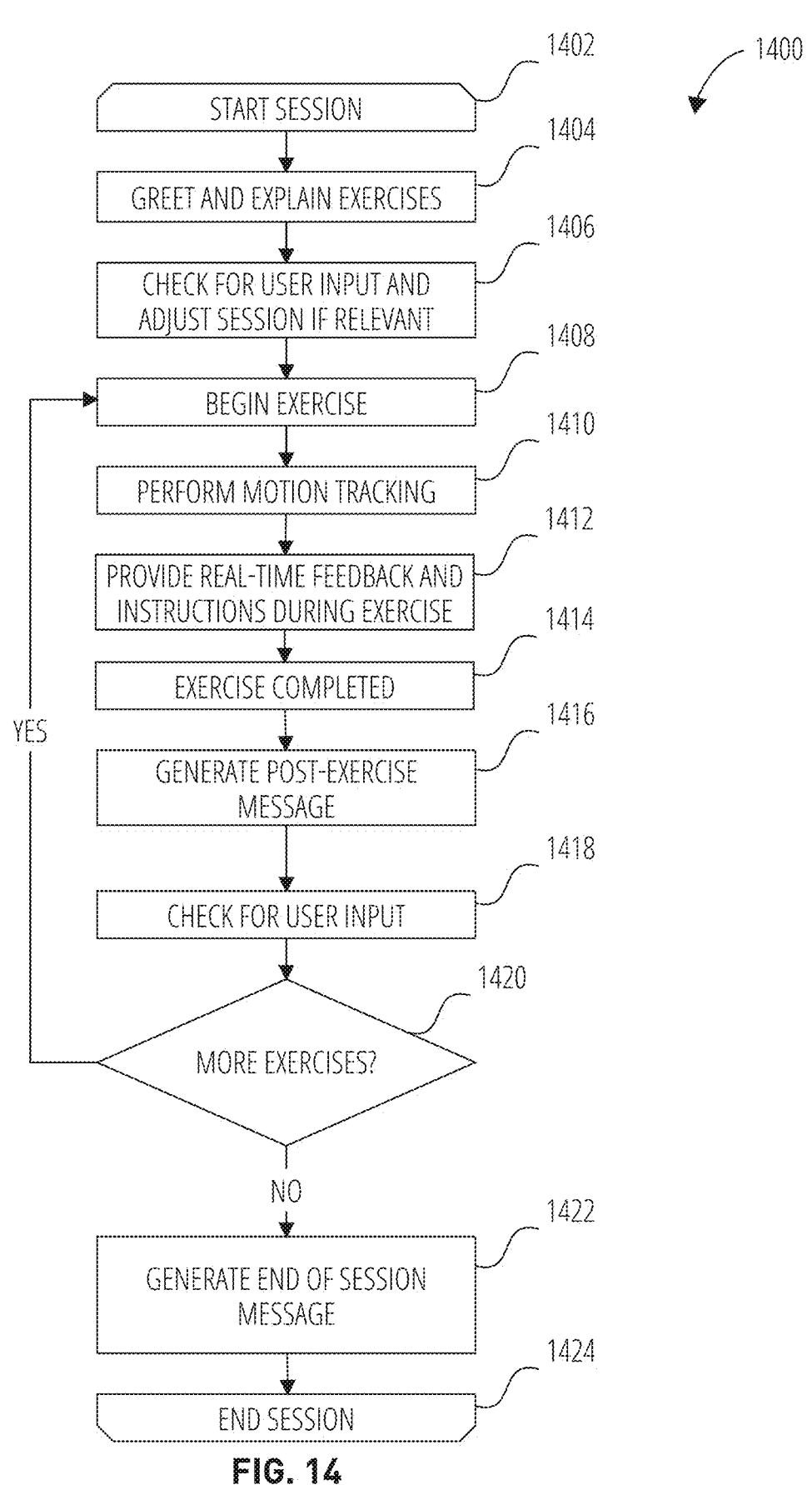
FIG. 14 is a flowchart illustrating a method of conducting an interactive digital care session, according to some examples.

FIG. 14 illustrates a method 1400 of conducting an interactive digital care session, according to some examples. The method 1400, as may be performed by the digital care platform 102 using components shown in FIG. 1 to FIG. 4, seeks to enhance the user's experience by providing timely and contextually relevant AI-generated messages that serve as touchpoints throughout a session. These messages may be delivered at various points in time, such as at the beginning of the session, after the completion of an exercise, during an exercise, and/or at the session's conclusion.

In some examples, at the onset of the session, the digital care platform 102 generates a welcoming message that is personalized to the user's profile, taking into account factors such as their progress in a therapy program, the date, or the specific time of day. This initial interaction may set a positive and encouraging tone, aiming to motivate the user and prepare them mentally for the session ahead.

The session may comprise performance of a plurality of exercises. In some examples, the exercises are generated by the reasoning system 304 and approved by the therapist 120. The exercises may include one or more exploratory program elements, with the digital care platform 102 tracking the results associated with such exploratory program elements for further training of one or more machine learning models, as described elsewhere in the present disclosure.

During the session, following each exercise, the digital care platform 102 may conduct an analysis of the user's performance using algorithms that assess a variety of metrics, such as range of motion, completion of repetitions, form, and/or the accuracy of movements. Based on this analysis, the digital care platform 102 crafts a post-exercise message that provides personalized feedback. This feedback is informative, giving the user insight into their performance, and also, where relevant, motivational, highlighting their achievements and areas of improvement in a manner that encourages perseverance and dedication.

In some examples, the digital care platform 102 can also generate personalized messages while the user is performing a particular exercise. For example, the digital care platform 102 detects that the user is not performing an exercise correctly (e.g., their back is not straight) and provides real-time feedback to help the user correct the issue.

As the session draws to a close, the digital care platform 102 may synthesize data from the session to generate a concluding message. This message serves as a summary of the user's performance throughout the session, reinforcing positive behaviors and accomplishments while also setting goals and expectations for future sessions.

In some examples, the digital care platform 102, through its intelligent use of AI messaging, creates a supportive environment that mirrors the interaction a user would have with a human therapist. By providing real-time, adaptive feedback, the digital care platform 102 can provide a feeling of a personalized and engaging experience, fostering an atmosphere conducive to recovery and rehabilitation. Such real-time, adaptive messaging or feedback can be facilitated by machine learning models such as LLMs, e.g., through the dynamic generation of prompts including relevant information to guide an LLM in generating an appropriate message.

Referring now specifically to the flowchart in FIG. 14, according to some examples, the method 1400 includes starting a session at opening loop element 1402. The digital care platform 102 initiates a new session when the user logs in, opts to start, or when a scheduled session time arrives. The user can use a computing device such as a tablet for the session, e.g., to run the digital care application. The digital care platform 102 loads the user's profile (e.g., as part of the digital care application), including scheduled exercises and historical data from previous sessions.

At operation 1404, the digital care platform 102 engages in an initial user interaction and instructional phase of the session (e.g., through the communication system 306). As the session commences, the digital care platform 102 activates a personalized communication protocol, generating a welcoming message that is tailored to the user's identity and current context. For example, this message is not merely a generic greeting; it is a thoughtful composition that incorporates the user's name, acknowledging their presence and participation. Additionally, the digital care platform 102 intelligently considers contextual factors such as the time of day—for example offering a bright "Good morning" or a calming "Good evening"—and the user's journey within the therapy program, recognizing milestones or encouraging continued progress.

Following the personalized greeting, the digital care platform 102 transitions to an educational mode, where it provides a detailed and understandable explanation of the exercises that are slated for the session. In some examples, this instructional content is designed to be clear and succinct, ensuring that the user comprehensively understands the activities they are about to undertake.

To cater to diverse learning preferences and accessibility needs, the digital care platform 102 employs a variety of instructional mediums. This can include audio output that is accompanied by appropriate visuals displayed at the user's device. Visual learners may benefit from illustrative aids such as diagrams or animated sequences that demonstrate the exercises, while auditory learners may prefer spoken instructions delivered through a text-to-speech conversion system of the digital care platform 102. For users 110 who favor reading or require written instructions to supplement their understanding, the digital care platform 102 can generate descriptive text. In some examples, the choice of instructional medium is determined by the user's pre-set preferences and the technological capabilities of the digital care platform 102.

In some examples, and as shown at operation 1406 of the method 1400, the digital care platform 102 checks for user input at this stage of the session. For example, the user may have provided new inputs, such as an indication of any new injury, their energy level, or what they are looking to achieve in the session. The digital care platform 102 can dynamically process such input and adjust the exercises accordingly (e.g., to accommodate an injury or energy level). For example, the reasoning system 304 can dynamically generate new exploratory program elements or novel exercise combinations based on real-time feedback and the trained machine learning model/s leveraged by the digital care platform 102.

The method 1400 initiates the exercise regimen at operation 1408. This stage marks the transition from preparatory activities to the active engagement of the user in their prescribed exercises. As the user embarks on the first exercise, the digital care platform 102 serves as an interactive guide, providing real-time instructions to help the user perform movements with precision and care.

The digital care platform 102, equipped with monitoring capabilities such as those described elsewhere in the present disclosure, digitally captures data regarding the user's movements (and, in some cases, other data, such as vital signs). Utilizing computer vision and/or other tracking technology, the digital care platform 102 captures a detailed account of the user's kinematics, providing a comprehensive analysis of each motion (e.g., using the observation system 302). Thus, the digital care platform 102 performs motion tracking at operation 1410. More details of motion tracking methodologies are described elsewhere herein.

In some examples, as the user progresses through the exercise, the digital care platform 102 analyzes each movement for accuracy and consistency. Should the user deviate from the prescribed form, the digital care platform 102 may intervene. The digital care platform 102 may do so by offering corrective cues, which are designed to be intuitive and easily actionable, allowing the user to adjust their movements in real-time.

Specifically, in some examples, the method 1400 includes providing real-time, personalized cues during exercise at operation 1412 (e.g., via the communication system 306). As the user performs the exercise, the digital care platform 102 analyzes the movement or other data in real-time. If deviations from the correct form are detected, the digital care platform 102 provides cues tailored to the user's immediate needs to correct their posture or movement. These personalized cues can facilitate an interactive conversation between the "AI care specialist," or "digital therapist," provided by the digital care platform 102, and the user, enhancing the adaptability of the session to the user's capabilities and responses.

For example, the AI care specialist might observe and comment, "You're struggling a bit with the upward part of the movement as you are losing your balance." If the user acknowledges the difficulty, responding with "Indeed, but I don't seem to be able to do it!" the AI care specialist can then offer actionable advice, such as, "Just focus on keeping your knees in place and rise slowly." The communication is designed to be actionable, providing the user with specific, real-time guidance that can be immediately implemented to improve performance. As mentioned, such communication can be implemented by dynamically prompting a model such as an LLM with relevant information (e.g., user and session context) and requesting a response in a particular format and style. Systems such as the reasoning system 304 and the communication system 306 can work together to generate and deliver such messages.

In some examples, the digital care platform 102 leverages specialized domain-specific language models to facilitate the interactive communications throughout a session. These models may be implemented as transformer-based architectures that have undergone multi-phase training processes tailored specifically for the relevant contexts, such as musculoskeletal care and pain management. An initial model may be trained on a comprehensive base dataset that includes clinical guidelines, evidence-based protocols, and proprietary datasets of therapeutic interactions, creating a foundation of knowledge about physical therapy exercises, musculoskeletal conditions, and recovery protocols, for example.

This training can then be enhanced through fine-tuning using supervised learning on labeled datasets of effective therapeutic communications, followed by reinforcement learning where the model's outputs are optimized based on dual reinforcement signals: explicit therapist validations of generated content and measurable outcomes from subsequent sessions. This specialized training enables the model to understand domain-specific terminology and nuances beyond generic language models, allowing it to recognize clinically significant information (such as "I felt a sharp twinge in my lower back during the last rep") and respond with contextually appropriate guidance.

In some examples, the specialized language model's integration with multiple data streams allows it to simultaneously process text data (such as context about the user) and sensor data from hardware components that track the user's movements. For instance, as a user performs an exercise, camera-based computer vision systems may detect that the knee is not bending to the full instructed angle, prompting the language model to generate contextually relevant feedback such as "Try bending a bit further, you have 5° more to go" in real time. This hardware-software synergy represents an advancement over conventional healthcare systems, as the language model's understanding of physical therapy principles combines with both the user's context information and real-time biomechanical data to generate personalized guidance that adapts to actual performance, not just reported experience.

Additionally, the digital care platform 102 may be equipped to handle requests from the user, such as asking the AI care specialist to skip an exercise due to pain. In such cases, the AI care specialist can respond with understanding and adapt the session accordingly, either by suggesting an alternative exercise (e.g., via the reasoning system 304) or by providing reassurance and instructions for managing discomfort.

According to some examples, the method 1400 includes automatically determining that an exercise is completed at operation 1414. Once the user completes the exercise, the digital care platform 102 processes the performance data to determine the quality of the exercise execution, such as the range of motion achieved and the accuracy of movements. This data may include the speed, acceleration, and trajectory of limbs, as well as the overall posture and alignment of the body during the exercise. Upon the completion of an exercise, the digital care platform 102 automatically detects this event using criteria such as the cessation of movement, the achievement of a target range of motion, or the completion of the expected number of repetitions.

According to some examples, the method 1400 includes generating a post-exercise message at operation 1416. For example, the digital care platform 102 may use performance data to generate a post-exercise message. This message includes personalized feedback on the user's performance, highlighting achievements such as improved range of motion or a high percentage of correct movements. The message may be crafted (e.g., using LLM prompting) to be motivational and encouraging, using positive reinforcement techniques.

In some examples, and as shown at operation 1418 of the method 1400, the digital care platform 102 checks for user input at this stage of the session. For example, the user may have provided the AI care specialist with an update on their energy level or pain level, or indicated a preference for the rest of the session. The digital care platform 102 can dynamically process such input and adjust the rest of the session accordingly.

At decision operation 1420, the digital care platform 102 determines whether the session includes further exercises scheduled for the session. If more exercises are planned, the digital care platform 102 proceeds to guide the user to the next exercise at operation 1408. If not, the digital care platform 102 transitions to the end-of-session phase.

Following a determination, at decision operation 1420, that no further exercises are scheduled for the session, the digital care platform 102 triggers ending of the session. At the culmination of the session, the digital care platform 102 engages in a process of data compilation and synthesis.

For example, the digital care platform 102 evaluates the user's performance, distilling the essence of their efforts, including the relevant motion tracking data, into a coherent end-of-session message which is generated at operation 1422. For example, the reasoning system 304 and the communication system 306 work together to process the relevant data and generate the message. This message serves as an overview, providing the user with a clear picture of their performance, including progress made towards their goals. Moreover, the end-of-session message may include motivational elements, designed to motivate the user to persist with their therapy regimen. The message may highlight specific accomplishments, such as achieving a new personal best in range of motion or maintaining a consistent pattern of correct movements.

According to some examples, the method 1400 includes ending the session at closing loop element 1424. The digital care platform 102 ends the session, logs the session data for future use (e.g., transmits the session data to the reasoning system 304 or for use in further machine learning model training), and may schedule the next session based on the user's program or schedule. The user may then log out or be logged out (e.g., of the digital care application as described above), or the computing device shuts down.

FIG. 15

Figure 15:
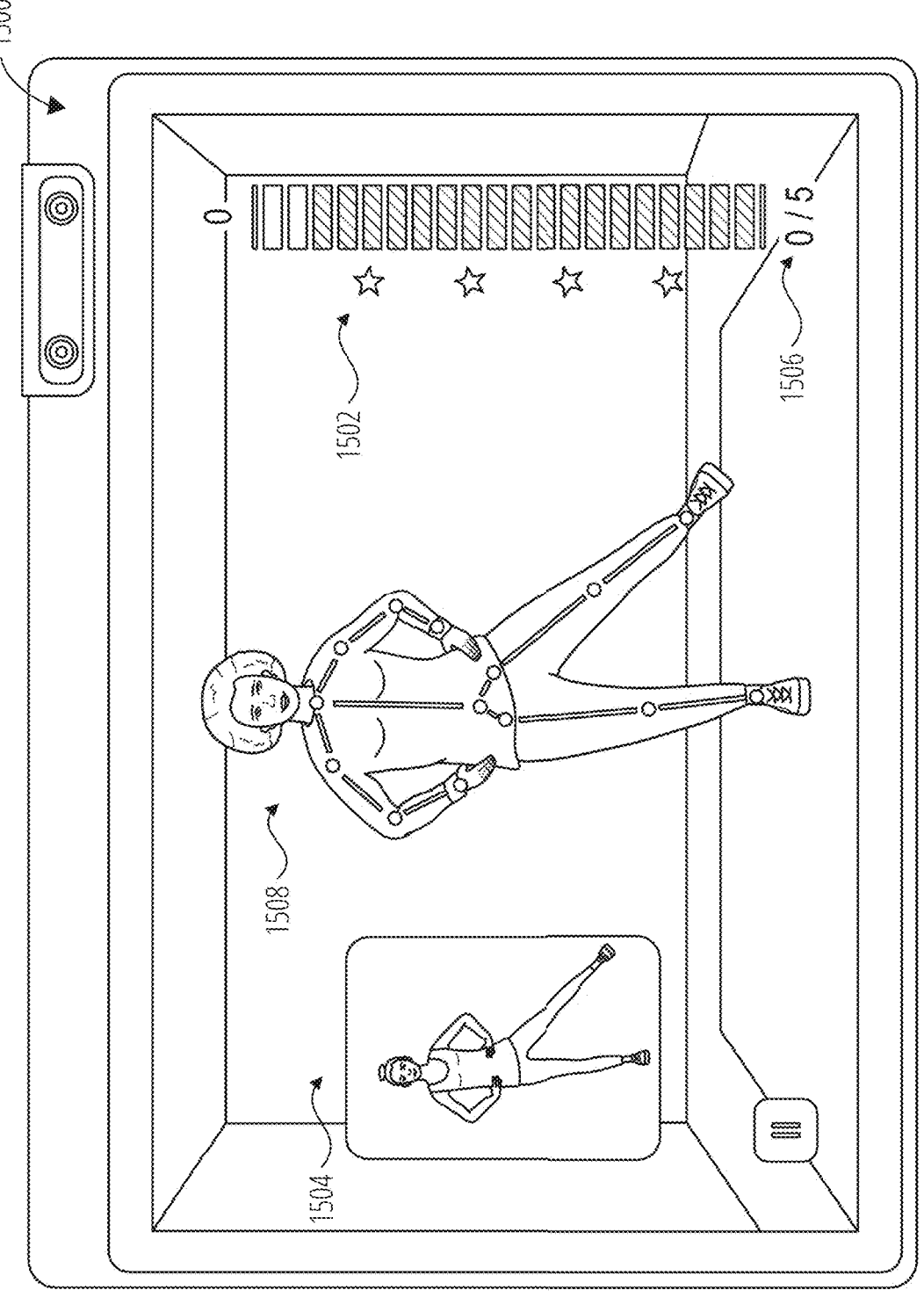
FIG. 15 is a user interface diagram illustrating a user interface presented to a tracked user during a session of a digital care platform, according to some examples.

FIG. 15 illustrates a user interface 1500 presented to a tracked user 1508 (e.g., the user 110 of the digital care platform 102) during an exercise session, according to some examples. For example, an interface such as the user interface 1500 can be presented while operations of the method 1400 of FIG. 14 or operations of FIG. 8 are performed.

The user interface 1500 illustrates example data presented via a display of a portable computing device (e.g., a tablet device), which is an example of the computing device 108 of FIG. 1. FIG. 15 shows real-time visual feedback elements during exercise performance, according to some examples. The user interface 1500 displays multiple elements to guide and provide feedback to the tracked user 1508.

The user interface 1500 shows the tracked user 1508, as captured by one or more cameras of the portable computing device. In other words, the portable computing device provides a real-time video feed to allow the tracked user 1508 to see themselves performing the relevant exercises. The tracked user 1508 is shown with the keypoints overlaid onto their body. It is noted that the keypoints are shown mainly for illustrative purposes and are not necessarily visible and/or not necessarily shown in the user interface 1500 during operation.

The user interface 1500 further presents real-time visual feedback elements 1502 (represented by bars and star symbols), and a real-time instructions section 1504 showing a smaller figure demonstrating the proper form for the relevant exercise. Thus, the tracked user 1508 can actively perform an exercise while watching their form on the display, while the portable computing device is capturing and processing images in real time to provide immediate feedback on their performance. A progress tracker 1506 in the user interface 1500 shows how many exercises or repetitions of an exercise (depending on the setting) have been completed.

In some examples, in addition to the real-time instructions section 1504 and the live feed of the tracked user 1508, the user interface 1500 can show and/or provide, via audio, an AI care specialist component. The AI care specialist component can operate as an AI-driven automated assistant or "digital therapist," providing guidance during exercise performance. For example, the AI care specialist can convey messages generated by the reasoning system 304 or the communication system 306 directly to the tracked user 1508, in real time. In some examples, in addition or as an alternative to the AI care specialist component providing audio output, the user interface 1500 can include a section with text output displaying the messages from the AI care specialist.

Figure 16:
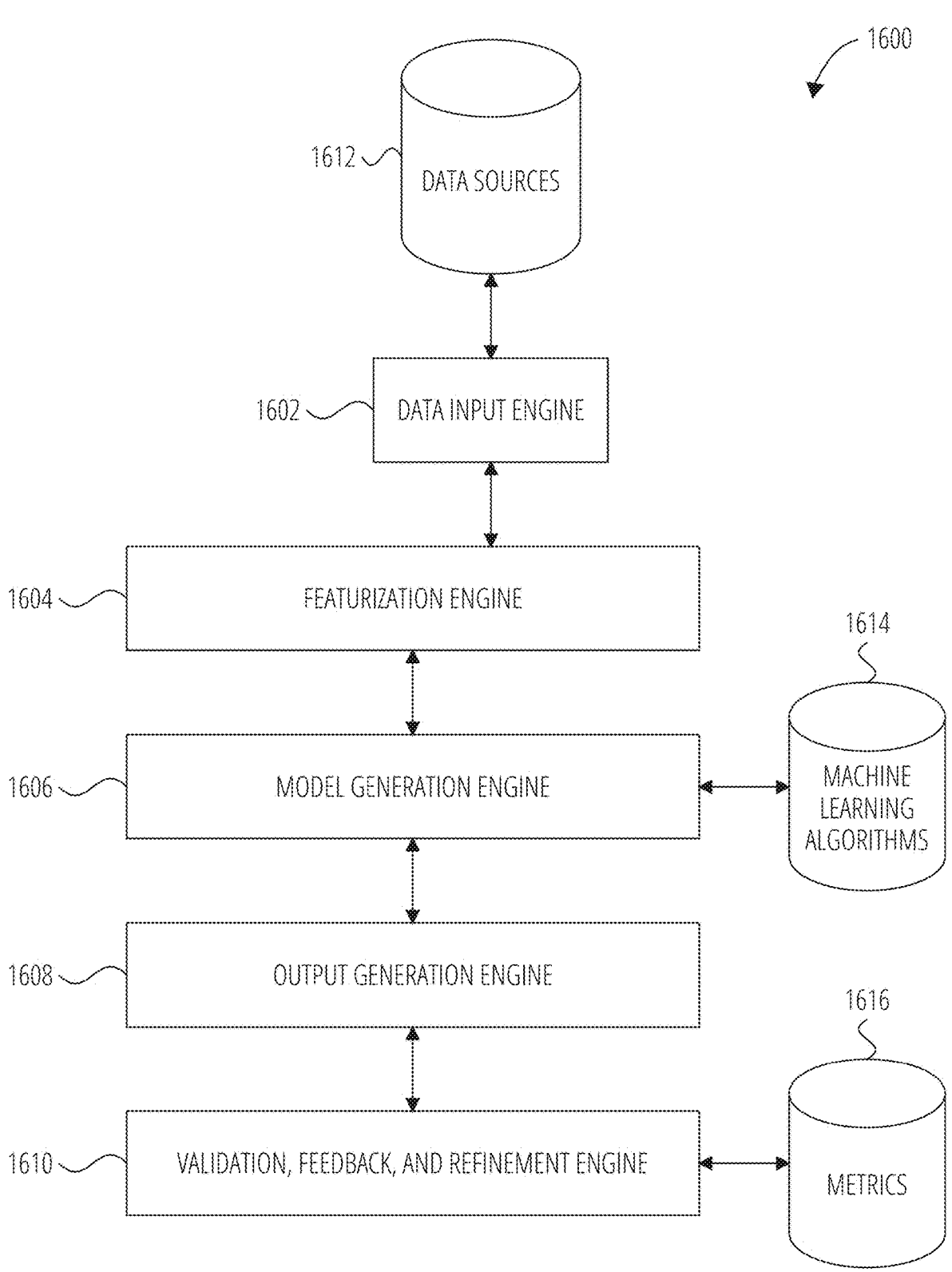
FIG. 16 is a block diagram illustrating components of a machine learning system, according to some examples.
Figure 17:
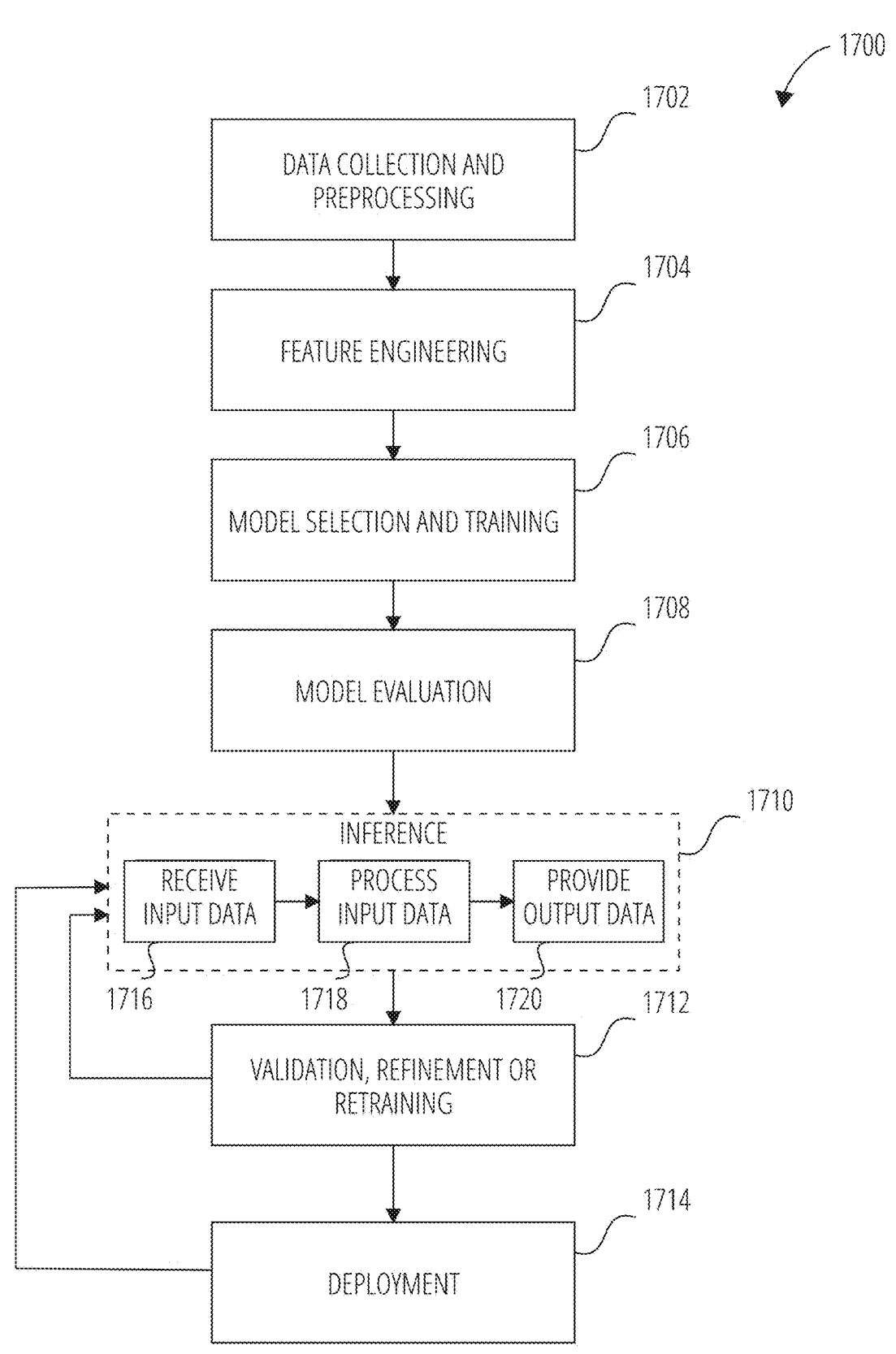
FIG. 17 is a flowchart illustrating a machine learning pipeline, according to some examples.
Figure 18:
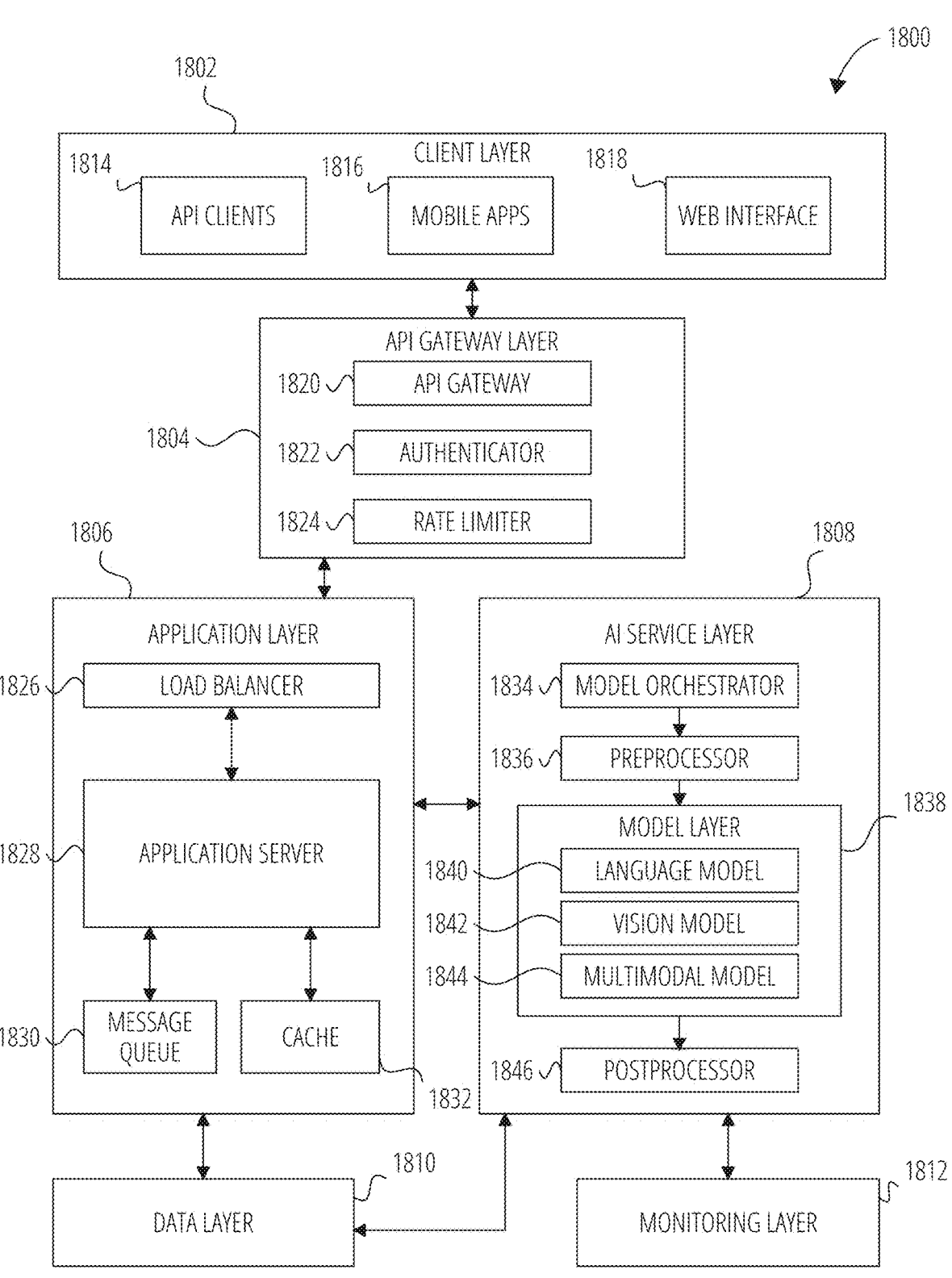
FIG. 18 is a system architecture diagram showing a layered view of an AI integrated system, according to some examples.

Example AI Systems and Methodologies (FIG. 16 to FIG. 18)

FIG. 16 illustrates a machine learning system 1600, according to some examples. The machine learning system 1600 may be used to implement one or more aspects of the present disclosure. The machine learning system 1600 is shown to include a data input engine 1602, a featurization engine 1604, a model generation engine 1606, an output generation engine 1608, and a validation, feedback, and refinement engine 1610.

The data input engine 1602 may be configured to access, interpret, request, format, re-format, or receive input data from data sources 1612. Data sources 1612 may include training data (e.g., data for training machine learning models), validation data (e.g., data for comparing model output with known results to evaluate performance), or reference data (e.g., data used to establish baselines or inform model creation). The data input engine 1602 can interact with external data systems via input/output (I/O) devices, network interfaces, or storage elements to ensure input data is processed and stored in a suitable format for further operations.

The featurization engine 1604 may be configured to transform input data into features that can be utilized by machine learning algorithms, which may include feature extraction, feature selection, normalization, encoding, and dimensionality reduction techniques. The featurization engine 1604 can handle feature extraction, scaling, or selection, helping the machine learning system 1600 to identify and process relevant data attributes for subsequent modeling. For example, features extracted from raw data may be annotated, labeled, or transformed into numerical representations suitable for machine learning algorithms 1614. The featurization engine 1604 can work iteratively with other components to refine features based on model requirements or outcomes.

The model generation engine 1606 is responsible for creating, training, and configuring one or more machine learning models based on input data and selected features. The model generation engine 1606 may include functionality for model selection, hyperparameter tuning, or algorithm implementation.

Machine learning broadly involves using computer algorithms to automatically learn patterns and/or relationships in data, often without the need for explicit programming. Thus, the machine learning algorithms 1614 may include various algorithms, including supervised, unsupervised, or reinforcement learning approaches, such as decision trees, neural networks, Support Vector Machines (SVMs), or deep learning architectures such as transformers or CNNs. The model generation engine 1606 may also support iterative model adjustment and validation cycles, which may allow for updates to the model based on new training data or changes in defined performance criteria as measured by, for example, metrics 1616.

In some examples, the output generation engine 1608 is responsible for model inference. The output generation engine 1608 processes data to produce predictions, classifications, or other results. The output generation engine 1608 can also apply post-processing techniques such as aggregation, thresholding, or confidence scoring to ensure outputs are in a format suitable for downstream systems or user interpretation.

The validation, feedback, and refinement engine 1610 may be configured to validate, monitor, or improve the performance and relevance of machine learning models over time. The validation, feedback, and refinement engine 1610 may apply validation data to compare model outputs against validation data, and may incorporate feedback from users or automated systems to potentially improve model performance based on specific metrics 1616. Metrics 1616 may be used to evaluate and compare model outputs against validation data or other useful data, providing insights into model performance, accuracy, reliability, or generalization. Refinement operations may involve retraining models with updated data or adjusting model parameters to account for changing conditions or newly observed patterns. Metrics 1616 may include performance evaluation measures such as accuracy, precision, recall, F1-score, area under the ROC curve (AUC), mean squared error (MSE), or log loss, depending on the type of machine learning task being performed.

Components of the machine learning system 1600 may be implemented by hardware processors and may communicate via network interfaces or shared storage elements to facilitate data exchange and coordination. The architecture shown in FIG. 16 provides a framework that may be configured for deployment in different machine learning applications, such as certain natural language processing tasks, computer vision implementations, or predictive analytics scenarios, with appropriate modifications to each component based on the particular application requirements.

FIG. 17 is a flowchart depicting a machine learning pipeline 1700, according to some examples. The machine learning pipeline 1700, or parts thereof, may be used to generate a trained machine learning model for use in one or more examples of the present disclosure.

The machine learning pipeline 1700 commences with a data collection and preprocessing stage 1702, in which data is acquired, cleaned, or formatted for compatibility with machine learning algorithms. The data collection and preprocessing stage 1702 may also involve addressing issues such as duplicate entries, missing values, or data inconsistencies.

During a feature engineering stage 1704, training data can be formatted, transformed, or selected as needed to create features that are useful for predicting target data. Feature engineering may include (1) receiving features (e.g., as structured or labeled data in supervised learning) and/or (2) identifying features (e.g., unstructured or unlabeled data for unsupervised learning) in training data. In this context, a feature may be a variable or attribute, such as a measurable property of a process, article, system, or phenomenon represented by a data set. Features may also be of different types, such as numeric features, strings, and graphs, and may include one or more of content, concepts, attributes, historical data, or user data, merely for example. During feature engineering stage 1704, raw data may be transformed into representative features through techniques such as normalization, one-hot encoding, binning, embedding generation, or feature crossing, which can improve model performance and generalization capabilities.

A model selection and training stage 1706 can include selecting an appropriate machine learning algorithm or strategy and training the relevant model on training data. The model selection and training stage 1706 may involve splitting the data into training and testing sets, using cross-validation to evaluate the model, and tuning hyperparameters to improve performance. During training, the model may be trained to find features that affect a predicted outcome. The result of the training is a trained machine learning model.

During training, the model may learn to optimize parameters through techniques such as gradient descent, stochastic gradient descent (SGD), or adaptive optimization methods such as Adam or RMSprop, which can help minimize the loss function and improve model convergence. In some examples, techniques such as model quantization, pruning, or knowledge distillation can reduce the computational complexity of a trained model. Quantization involves reducing the precision of weights and activations (e.g., from 32-bit floating-point to 8-bit integers), which may help with efficient deployment on hardware-constrained environments such as edge devices. Pruning removes redundant or non-contributory connections within a model, thereby reducing memory and processing requirements. Knowledge distillation transfers the learned knowledge of a large, complex model into a smaller, lightweight model.

A model evaluation stage 1708 may include evaluating the performance of a trained model on a separate testing dataset. This can help determine if the model is overfitting or underfitting and determine whether the model is suitable for deployment. Regularization techniques, such as dropout or L2 regularization, may also be employed to help reduce overfitting and improve generalization.

FIG. 17 further shows an inference stage 1710, in which a trained model generates outputs on new, unseen data. For example, for each input, at operation 1716, the model receives input data (e.g., from external sources, such as real-time sensors, databases, or user-provided queries, or internal sources such as test inputs). At operation 1718, the trained model processes the input data. This can include various operations that are performed to arrive at output data, such as feature extraction, transformation, and embedding generation, depending on the model architecture. For example, a CNN may process input images by applying convolutional filters, while a transformer model might encode textual input using self-attention mechanisms. The trained model may perform inference, mapping inputs to outputs, such as predictions or classifications, thereby providing the output data at operation 1720.

It is noted that output data may take various forms. In classification AI examples, outputs may include data classifications or probabilities linked to particular classifications. In generative AI examples, outputs may include new content, such as translations, summaries, answers, new media content, or combinations thereof. In some examples, outputs are further processed into usable output, such as probabilities, labels, or continuous values tailored for downstream systems. Post-processing may include confidence scoring, aggregation, or error correction, to ensure outputs are accurate and actionable for the intended application.

The machine learning pipeline 1700 may also include a validation, refinement, or retraining stage 1712. This may include updating a model based on feedback generated from the inference stage 1710, such as new data or user feedback. In some examples, validation is performed using a separate dataset known as the validation dataset. The validation dataset can be used to tune or fine-tune the hyperparameters of a model, such as the learning rate and the regularization parameter. The hyperparameters may be adjusted to improve the model's performance on the validation dataset.

During deployment stage 1714, the trained model is integrated into or connected with a more extensive or real-world system, application, or environment, such as a web service, mobile app, or Internet of Things (IOT) device. This phase can involve setting up APIs, building a user interface, and ensuring that the model is scalable and can handle large volumes of data. In some examples, the trained model is deployed on a single device, such as locally on an end user's computing device or on an edge device, as opposed to being deployed on a server system. This may provide lower latency or offline functionality in certain scenarios. Accordingly, various trained models can be deployed as server-based deployments or on-device deployments.

In some examples, a trained model includes one or more neural networks. The neural network may include a hierarchical (e.g., layered) organization of neurons or nodes, with each layer consisting of multiple neurons or nodes. Neurons in the input layer receive the input data, while neurons in the output layer produce the final output of the network. Between the input and output layers, there may be one or more hidden layers, each consisting of multiple neurons.

Each neuron may operationally compute a function, such as an activation function, which takes as input the weighted sum of the outputs of the neurons in the previous layer, as well as a bias term. The output of this function is then passed as input to the neurons in the next layer. If the output of the activation function exceeds a certain threshold, an output is communicated from that neuron (e.g., transmitting neuron) to a connected neuron (e.g., receiving neuron) in successive layers. The connections between neurons have associated weights, which define the influence of the input from a transmitting neuron to a receiving neuron. During the training phase, these weights are adjusted by the learning algorithm to optimize the performance of the network. Different types of neural networks may use different activation functions and learning algorithms, affecting their performance on different tasks. The layered organization of neurons and the use of activation functions and weights help neural networks to model complex relationships between inputs and outputs, and to generalize to new inputs that were not seen during training.

A neural network can be applied in various scenarios. In some cases, the neural network is configured to perform an image or video processing task. For example, the task may be image classification. As another example, the task can be image embedding generation and the output generated by the neural network can be a numeric embedding of the input image. As yet another example, the task can be object detection and the output generated by the neural network can identify locations in the input image at which particular types of objects are depicted. As another example, if the input to the neural network is a sequence of text in one language, the output generated by the neural network may be a piece of text in the other language that is a predicted proper translation of the input text into the other language.

In some cases, a machine learning task is a multi-modal processing task that requires processing multi-modal data. In general, multi-modal data is a combination of two or more different types of data, e.g., two or more of audio data, image data, text data, or graph data. As one example, the multi-modal data may comprise audio-visual data, comprising a combination of pixels of an image or of video and audio data representing values of a digitized audio waveform. As another example, the multi-modal data may comprise a combination of text data representing text in a natural language and pixels of an image.

In some examples, the neural network may also be one of several different types of neural networks, such as a single-layer feed-forward network, a Multilayer Perceptron (MLP), an Artificial Neural Network (ANN), a Recurrent Neural Network (RNN), a Long Short-Term Memory Network (LSTM), a Bidirectional Neural Network, a symmetrically connected neural network, a Deep Belief Network (DBN), a CNN, a Generative Adversarial Network (GAN), an Autoencoder Neural Network (AE), a Restricted Boltzmann Machine (RBM), a Hopfield Network, a Self-Organizing Map (SOM), a Radial Basis Function Network (RBFN), a Spiking Neural Network (SNN), a Liquid State Machine (LSM), an Echo State Network (ESN), a Neural Turing Machine (NTM), or a Transformer Network, merely for example.

As mentioned, a generative AI model can generate new content. For example, generative AI can produce text, images, video, audio, code, or synthetic data. In some examples, the generated content may be similar to original data, but not identical.

Some of the techniques or architectures that may be used in generative AI are GANs, Variational autoencoders (VAEs), and transformers. GANs may include two neural networks: a generator and a discriminator. The generator network attempts to create realistic content that can "fool" the discriminator network, while the discriminator network attempts to distinguish between real and fake content. The generator and discriminator networks operate in an adversarial relationship where, through iterative training, the generator may produce increasingly realistic outputs while the discriminator may become more effective at distinguishing between real and generated content. VAEs may encode input data into a latent space (e.g., a compressed representation) and then decode it back into output data. The latent space can be manipulated to generate new variations of the output data. VAEs may use self-attention mechanisms to process input data, allowing them to handle long text sequences and capture complex dependencies. Transformer models may use attention mechanisms to learn the relationships between different parts of input data (such as words or pixels) and generate output data based on these relationships. In some examples, transformer models can handle sequential data, such as text or speech, as well as non-sequential data, such as images or code.

Example Machine Learning Model Specifications, Training, and Configuration

In some examples, the machine learning model is in the form of a transformer-based language model used by a digital care platform to analyze user interaction data and generate personalized recommendations for program elements and/or user interactions, as discussed elsewhere in the present disclosure.

In some examples, the machine learning model is in the form of a computer vision model for human pose tracking to allow a digital care platform to assess how a user is performing certain exercises. The architecture of this machine learning model includes, for example, a lightweight convolutional neural network (CNN) topology. For instance, a neural network may include 34 layers with ReLU activation functions and convolutional connections, designed for efficiency and real-time performance on resource-constrained devices.

The example machine learning model is trained using supervised learning. The training process employs gradient descent with backpropagation, with a focus on minimizing a loss function such as mean squared error to optimize keypoint localization accuracy. The model parameters are adjusted iteratively based on a training strategy involving a batch size of 32 and an exponentially decaying learning rate schedule.

In some examples, the training data used for the machine learning model is sourced from publicly available datasets, such as COCO and MPII Human Pose, supplemented with proprietary motion capture data. The training data may include representative variations of the relevant parameters, such as joint angles, body orientations, and lighting conditions. For instance, the training dataset is structured to cover diverse human poses and movements and includes 100,000 or more examples.

Input data to the machine learning model may include RGB video frames or image sequences captured from a camera. In some examples, these inputs are preprocessed using normalization and resizing to a fixed resolution (e.g., 256×256 pixels). For example, pixel intensities are normalized to a range of [0, 1] using min-max normalization to ensure consistent input scaling. In some examples, input may also include depth information, such as depth map data.

The output of the machine learning model represents 2D or 3D coordinates of human keypoints (e.g., joints such as shoulders, elbows, and knees). In some examples, the machine learning model generates outputs such as predicted joint positions in a format compatible with downstream processes, using postprocessing methods such as heatmap decoding and coordinate regression to refine predictions.

The example machine learning model uses specific parameters for its computations, including a learning rate, momentum, and weight decay coefficients. These parameters can be chosen based on hyperparameter optimization using grid search or random search. For example, the learning rate is set to 0.001 to balance convergence speed and stability. To ensure the effectiveness of the machine learning model, input parameters are selected based on their relevance to the predicted output. For instance, pixel intensities and spatial relationships have been identified as parameters influencing joint position accuracy. Parameters that are less relevant, such as background textures, may be omitted or weighted lower during training.

In some examples, training data undergoes validation to ensure quality and representativeness. This can include checks for missing values, mislabeled keypoints, or inconsistent annotations. For example, outlier detection is performed using interquartile range (IQR) analysis, and invalid data points are either corrected or excluded.

The machine learning model may be adapted periodically using new data from real-time user interactions on the digital care platform. Adaptation may involve fine-tuning pre-trained weights to account for evolving user demographics or newly observed exercise patterns.

The machine learning model can be deployed in various environments, including edge devices such as tablet computers or smartphones that can be used in digital care. Deployment considerations include optimizing for latency and memory usage, ensuring compatibility with mobile operating systems (e.g., iOS or Android), and adhering to low-latency requirements for real-time feedback. For instance, the model may be containerized using Docker for scalability and portability across different systems.

FIG. 18 is a system architecture diagram showing a layered view of an AI integrated system 1800, according to some examples. The AI integrated system 1800 comprises six example layers: a client layer 1802, an API gateway layer 1804, an application layer 1806, an AI service layer 1808, a data layer 1810, and a monitoring layer 1812.

The client layer 1802 provides multiple access points for system interaction. It includes API clients 1814, which may facilitate programmatic access to the capabilities of the AI integrated system 1800 or integration with third-party systems and services. Mobile applications 1816 facilitate access from mobile applications and devices, for example implementing native mobile protocols while maintaining consistent communication patterns with backend systems. A web interface 1818 enables browser-based access to the capabilities of the AI integrated system 1800 and may communicate with other layers using, for example, Hypertext Transfer Protocol (HTTP) or Hypertext Transfer Protocol Secure (HTTPS) protocols.

The API gateway layer 1804 serves as an entry point for client communications. The API gateway layer 1804 comprises an API gateway 1820, which may implement routing logic to direct incoming requests to appropriate backend services. An authenticator 1822 validates client credentials, for example using industry-standard protocols, such as OAuth 2.0 (Open Authorization 2.0) or JWT (JSON Web Tokens). In some examples, a rate limiter 1824 of the API gateway layer 1804 operates to help reduce system abuse or ensure resource allocation among clients.

The application layer 1806 comprises various processing capabilities. In some examples, the application layer 1806 includes a load balancer 1826 that may distribute incoming requests across multiple application server instances to support resource utilization and system reliability. An application server 1828 may implement business or core functional logic of the AI integrated system 1800, processing requests and coordinating responses across various system components. In some examples, a message queue 1830 facilitates asynchronous processing capabilities, facilitating efficient handling of operations, and a cache 1832 operates within the application layer 1806 to improve response times for frequently requested data.

The AI service layer 1808 provides AI capabilities through a structured approach to model deployment and execution. In some examples, the AI service layer 1808 includes a model orchestrator 1834 that coordinates the execution of one or various AI models, managing resource allocation and implementing routing logic to direct requests to appropriate model instances. The model orchestrator 1834 may implement functionality such as container orchestration, model versioning, and dynamic scaling to efficiently manage model deployment and execution across computing resources. A preprocessor 1836 may prepare input data for model consumption, implementing transformations, validations, or other preprocessing operations.

FIG. 18 shows the AI service layer 1808 as including a model layer 1838. The model layer 1838 may include multiple model types, including, for example, one or more of: a language model 1840 for processing textual input, implementing natural language processing capabilities; a vision model 1842 for handling image or video processing tasks; and a multimodal model 1844 that combines multiple input types to provide comprehensive analysis capabilities. In some examples, a postprocessor 1846 of the AI service layer 1808 transforms model outputs into standardized formats suitable for client consumption.

The data layer 1810 provides persistent storage capabilities. While not detailed in FIG. 18, it is noted that the data layer 1810 may include various components such as a primary database for maintaining transactional data, a vector database for optimizing storage and retrieval of high-dimensional vectors used in AI applications and models of the AI service layer 1808, or a file storage component for managing binary data assets.

The monitoring layer 1812 may provide observability capabilities across the AI integrated system 1800. This may include logging for capturing system events, metrics collection for performance analysis, or distributed tracing for detailed analysis of request flow through the system.

Communication between layers of the AI integrated system 1800 may follow defined patterns. External communications may implement appropriate encryption protocols, for example utilizing Transport Layer Security (TLS) or Secure Sockets Layer (SSL) for data protection. Internal communications may use various protocols selected for specific use cases, for example, Hypertext Transfer Protocol version 2 (HTTP/2), gRPC (Google Remote Procedure Call), or proprietary protocols where appropriate.

Referring again to the model layer 1838, this layer may incorporate various types of machine learning models. Neural networks may be deployed to implement various architectures suited to specific processing needs.

A language model such as the language model 1840 may use transformer-based architectures (e.g., Bidirectional Encoder Representations from Transformers (BERT), Generative Pre-trained Transformer (GPT) variants, or Text-to-Text Transfer Transformer (T5)) for processing textual data and implementing natural language understanding capabilities. A vision model such as the vision model 1842 may employ specialized neural network architectures (e.g., CNNs, Vision Transformers (ViT), or Residual Neural Network (ResNet) variants) for processing visual information and extracting features from images or video streams. A multimodal model such as the multimodal model 1844 may implement hybrid architectures (e.g., Contrastive Language-Image Pre-training (CLIP), DALL-E variants, or multimodal transformers) designed to process and correlate information across different input modalities, leveraging ensemble approaches to combine multiple model types using model aggregation or weighted prediction strategies. A multimodal model may combine textual, visual, and other forms of input data to provide analysis and generate integrated outputs that leverage cross-modal understanding capabilities.

The AI service layer 1808 may provide both supervised learning models (e.g., decision trees, random forests, or support vector machines) for specific classification and prediction tasks, and unsupervised learning models (e.g., k-means clustering or principal component analysis) for pattern discovery and dimensionality reduction within the data processing pipeline. Probabilistic models (e.g., Bayesian networks or hidden Markov models) may be integrated within the AI service layer 1808 to handle uncertainty in decision-making processes, working in conjunction with the preprocessor 1836 and postprocessor 1846 components to provide probability estimates and confidence metrics for model outputs.

Each model type may be implemented using various deployment strategies, with the model orchestrator 1834 managing their execution and resource allocation to ensure adequate performance and efficient system operation. This may include coordinating the deployment and execution of various model types, ensuring efficient resource allocation, and appropriate model selection based on specific task requirements. While in some examples the model layer 1838 provides server-based access to one or more models, a model can alternatively (or additionally) be deployed so as to perform inference locally (e.g., at the client layer 1802).

Figure 19:
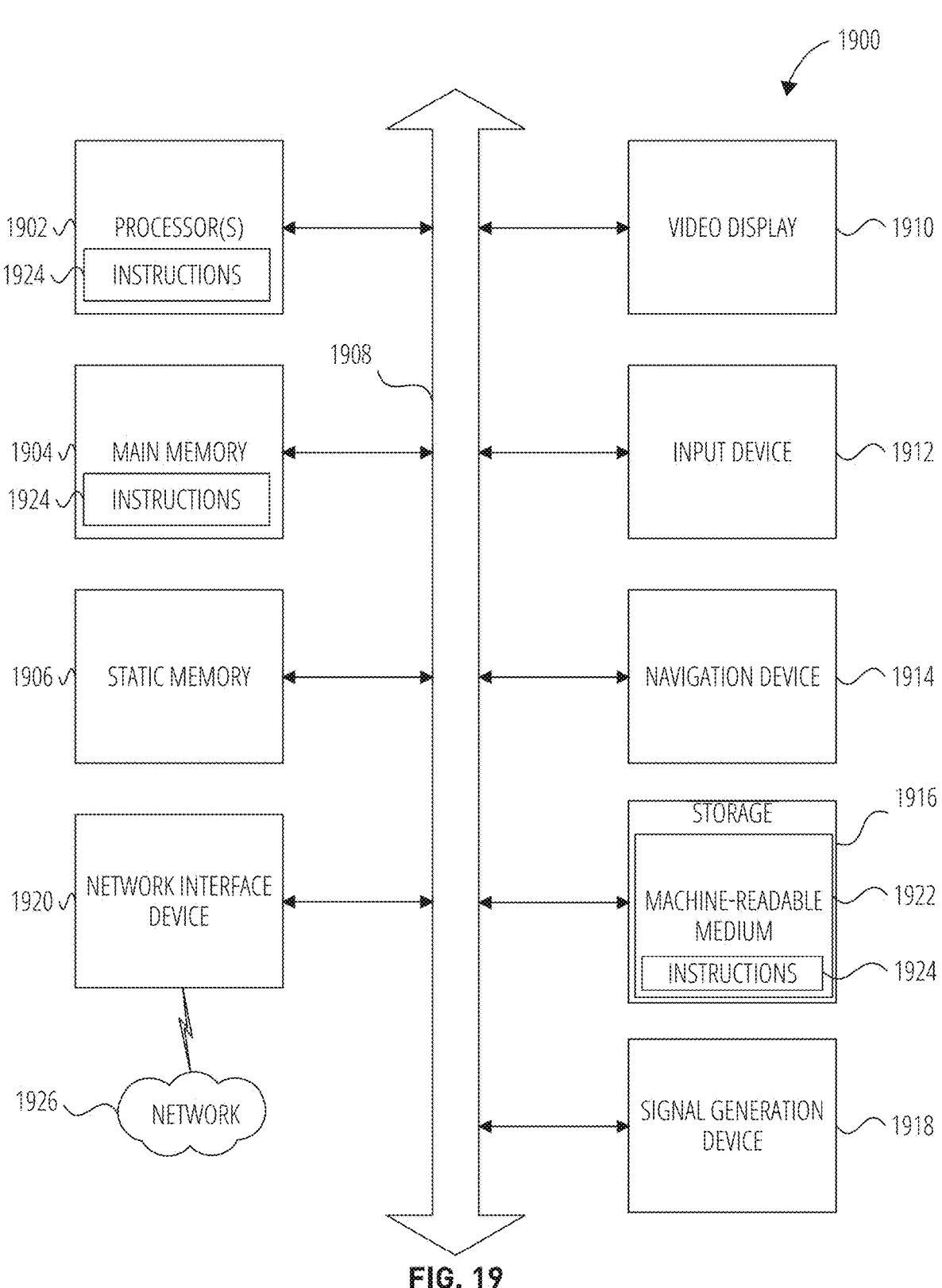
FIG. 19 is a block diagram of a computing system, according to some examples, within which instructions may be executed to perform one or more of the methodologies discussed herein.

Example Computing Systems (FIG. 19)

FIG. 19 is a block diagram of a machine in the example form of a computing system 1900, according to some examples, within which instructions 1924 may be executed for causing the computing system 1900 to perform one or more of the methodologies discussed herein. In some examples, the computing system 1900 includes a machine that operates as a standalone device, while in other examples the computing system 1900 includes a machine that is connected (e.g., networked) to other machines. The computing system 1900 can provide or form part of an operating environment in which aspects of the present disclosure are implemented.

In a networked deployment, a machine may operate in the capacity of a server or a client machine in server-client network environment, or as a peer machine in a peer-to-peer (or distributed) network environment. The machine may be a computer, a tablet, a cellular telephone, a web appliance, or other machine capable of executing instructions (sequential or otherwise) that specify actions to be taken by that machine. It is noted that while components typically related to only a single machine are illustrated in FIG. 19, the term "machine" shall also be taken to include any collection of machines that individually or jointly execute a set (or multiple sets) of instructions to perform any one or more of the methodologies discussed herein. The computing system 1900 may thus include multiple connected machines. Computing devices can be connected by a network.

The example computing system 1900 includes one or more processor(s) 1902 (e.g., a Central Processing Unit (CPU), a Graphics Processing Unit (GPU), or both), a primary or main memory 1904, and a static memory 1906, which communicate with each other via one or more communication connections 1908 (e.g., a bus, controller, or network connection). The computing system 1900 may further include one or more output devices, such as a display unit 1910 (e.g., an LCD or Light-emitting diode (LED) display).

The computing system 1900 also includes one or more input devices, such as an input device 1912 (e.g., a keyboard or a touch-sensitive display screen), a navigation device 1914 (e.g., a mouse), storage 1916, a signal generation device 1918 (e.g., a speaker), and a network interface device 1920. The storage 1916 includes a machine-readable medium 1922 on which is stored one or more sets of data structures and instructions 1924 (e.g., software) embodying or utilized by one or more of the methodologies or functions described herein. The instructions 1924 may also reside, completely or at least partially, within the main memory 1904 or within the processor(s) 1902 during execution thereof by the computing system 1900, with the main memory 1904 and the processor(s) 1902 also each constituting a machine-readable medium 1922.

While the machine-readable medium 1922 is shown in accordance with some examples to be a single medium, the term "machine-readable medium" may include a single medium or multiple media (e.g., a centralized or distributed database, or associated caches and servers) that store the one or more instructions 1924 or data structures. The term "machine-readable medium" shall also be taken to include any tangible medium that is capable of storing, encoding, or carrying instructions 1924 for execution by the machine and that cause the machine to perform any one or more of the methodologies of the present disclosure, or that is capable of storing, encoding, or carrying data structures utilized by or associated with such instructions 1924. The term "machine-readable medium" shall accordingly be taken to include, but not be limited to, solid-state memories, and optical and magnetic media. Specific examples of a machine-readable medium 1922 include non-volatile memory, including by way of example semiconductor memory devices, e.g., erasable programmable read-only memory (EPROM), electrically erasable programmable read-only memory (EEPROM), and flash memory devices; magnetic disks such as internal hard disks and removable disks; magneto-optical disks; and compact disc read-only memory (CD-ROM) and digital versatile disc read-only memory (DVD-ROM) disks. A machine-readable medium is not a transmission medium.

The instructions 1924 may further be transmitted or received over a communications network 1926 using a transmission medium. The instructions 1924 may be transmitted using the network interface device 1920 and any one of a number of well-known transfer protocols (e.g., hypertext transport protocol (HTTP)). Examples of communication networks include a local area network (LAN), a wide area network (WAN), the Internet, mobile telephone networks, plain old telephone (POTS) networks, and wireless data networks (e.g., Wi-Fi and Wi-Max networks). The term "transmission medium" shall be taken to include any intangible medium that is capable of storing, encoding, or carrying instructions 1924 for execution by the machine, and includes digital or analog communications signals or other intangible media to facilitate communication of such software.

Typically, operating system software (not shown) provides an operating environment for software executing in the computing system 1900, and coordinates activities of the components of the computing system 1900. One or more API calls may be made between components of the computing system 1900, or between a component of the computing system 1900 and an external component, based on user input received at the computing system 1900.

As used herein, the term "processor" may refer to any one or more circuits or virtual circuits (e.g., a physical circuit emulated by logic executing on an actual processor) that manipulates data values according to control signals (e.g., commands, opcodes, machine code, control words, macroinstructions, etc.) and which produces corresponding output signals that are applied to operate a machine. A processor may, for example, include at least one of a CPU, a Reduced Instruction Set Computing (RISC) Processor, a Complex Instruction Set Computing (CISC) Processor, a GPU, a Digital Signal Processor (DSP), a Tensor Processing Unit (TPU), a Neural Processing Unit (NPU), a Vision Processing Unit (VPU), a Machine Learning Accelerator, an Artificial Intelligence Accelerator, an Application Specific Integrated Circuit (ASIC), a Field Programmable Gate Array (FPGA), a Radio-Frequency Integrated Circuit (RFIC), a Neuromorphic Processor, a Quantum Processor, or any combination thereof. A processor may be a multi-core processor having two or more independent processors (sometimes referred to as "cores") that may execute instructions contemporaneously. Multi-core processors may contain multiple computational cores on a single integrated circuit die, each of which can independently execute program instructions in parallel. Parallel processing on multi-core processors may be implemented via architectures like superscalar, VLIW, vector processing, or SIMD that allow each core to run separate instruction streams concurrently. A processor may be emulated in software, running on a physical processor, as a virtual processor or virtual circuit. The virtual processor may behave like an independent processor but is implemented in software rather than hardware.

Operations of example methods described herein may be performed, at least partially, by one or more processors that are temporarily configured (e.g., by software) or permanently configured to perform the relevant operations. The performance of certain of the operations may be distributed among the one or more processors, not only residing within a single machine, but deployed across a number of machines. A hardware-implemented component for performing method operations may comprise dedicated circuitry or logic that is permanently configured (e.g., as a special-purpose processor, such as an FPGA or an ASIC) to perform certain operations. A hardware-implemented component may also comprise programmable logic or circuitry (e.g., as encompassed within a general-purpose processor or another programmable processor) that is temporarily configured by software to perform certain operations.

One or more processors may operate to support performance of the relevant operations in a "cloud computing" environment or as a "software as a service (SaaS)." For example, at least some of the operations may be performed by a group of computers (as examples of machines including processors), these operations being accessible via a network (e.g., the Internet) and via one or more appropriate interfaces (e.g., APIs). In practice, cloud-based, on-premises-based, or hybrid scenarios can be supported in some examples.

Examples may be implemented in digital electronic circuitry, or in computer hardware, firmware, or software, or in combinations of them. Examples may be implemented using a computer program product, such as a computer program tangibly embodied in an information carrier (e.g., in a machine-readable medium for execution by, or to control the operation of, data processing apparatus, such as a programmable processor, a computer, or multiple computers). A computer program can be written in any suitable form of programming language, including compiled or interpreted languages, and it can be deployed in any form, including as a standalone program or as a module, subroutine, or other unit suitable for use in a computing environment. A computer program can be deployed to be executed on one computer or on multiple computers at one site or distributed across multiple sites and interconnected by a communication network.

Although specific examples are described herein, it will be evident that various modifications and changes may be made to these examples without departing from the broader spirit and scope of the disclosure. Accordingly, the specification and drawings are to be regarded in an illustrative rather than a restrictive sense. Examples of the subject matter may be referred to herein, individually or collectively, by the term "example" merely for convenience and without intending to voluntarily limit the scope of this application to any single example or concept if more than one is in fact disclosed. Thus, although specific examples have been illustrated and described herein, it should be appreciated that the present disclosure can also cover adaptations, combinations, or variations of various examples, including structural or logical substitutions and changes.

Unless specifically stated otherwise, discussions herein using words such as "processing," "computing," "calculating," "determining," "presenting," "displaying," or the like may refer to actions or processes of a machine (e.g., a computer) that manipulates or transforms data represented as physical (e.g., electronic, magnetic, or optical) quantities within one or more memories (e.g., volatile memory, non-volatile memory, or any suitable combination thereof), registers, or other machine components that receive, store, transmit, or display information. Furthermore, unless specifically stated otherwise, the terms "a" and "an" are herein used, as is common in patent documents, to include one or more than one instance. Where the context permits, words using the singular or plural number may also include the plural or singular number, respectively. Except as otherwise indicated, the word "or" in reference to a list of two or more items, covers all of the following interpretations of the word: any one of the items in the list, all of the items in the list, and any combination of the items in the list.

As used in this disclosure, phrases of the form "at least one of an A, a B, or a C," "at least one of A, B, or C," "at least one of A, B, and C," and the like, should be interpreted to select at least one from the group that comprises "A, B, and C." Unless explicitly stated otherwise in connection with a particular instance in this disclosure, this manner of phrasing does not mean "at least one of A, at least one of B, and at least one of C." As used in this disclosure, the example "at least one of an A, a B, or a C," would cover any of the following selections: {A}, {B}, {C}, {A, B}, {A, C}, {B, C}, and {A, B, C}.

Although some examples, such as those depicted in the drawings, include a particular sequence of operations, the sequence may be altered without departing from the scope of the present disclosure. For example, some of the operations depicted may be performed in parallel or in a different sequence that does not materially affect the functions as described in the examples. In other examples, different components of an example device or system that implements an example method may perform functions at substantially the same time or in a specific sequence. The term "operation" is used to refer to elements in the drawings of this disclosure for ease of reference and it will be appreciated that each "operation" may identify one or more operations, processes, actions, or steps, and may be performed by one or multiple components.

EXAMPLES

In view of the above-described implementations of subject matter this application discloses the following list of examples, wherein one feature of an example in isolation or more than one feature of an example, taken in combination and, optionally, in combination with one or more features of one or more further examples are further examples also falling within the disclosure of this application.

Example 1 is a system comprising: a plurality of hardware devices associated with a plurality of tracked users of the system; one or more hardware processors; and memory storing instructions that, when executed by the one or more hardware processors, cause the one or more hardware processors to perform operations comprising: for each tracked user of the plurality of tracked users: maintaining, in at least one database, user data comprising at least one of user tracking data or user interaction data related to an activity program of the tracked user, the tracking data based at least partially on sensor data from one or more sensors of a hardware device from among the plurality of hardware devices that is associated with the tracked user; processing, by one or more machine learning models, the user data to obtain recommendation data comprising one or more automatically generated exploratory program elements of the activity program of the tracked user, generating validated activity program data based on user input, received from a supervising user from among a plurality of supervising users of the system, in response to the recommendation data, and updating, in the at least one database, the user data to record results of the activity program performed according to the validated activity program data; automatically modifying parameters of the one or more machine learning models based on both the validated activity program data of the plurality of tracked users and the results of the plurality of tracked users; and after modifying the parameters of the one or more machine learning models, generating further recommendation data for at least one the plurality of tracked users.

In Example 2, the subject matter of Example 1 includes, wherein the modifying of the parameters of the one or more machine learning models comprises performing at least one of supervised fine-tuning, reinforcement fine-tuning, or reinforcement learning with human feedback.

In Example 3, the subject matter of Examples 1-2 includes, wherein the modifying of the parameters of the one or more machine learning models comprises performing automated reinforcement learning by: updating a first reinforcement learning signal based on the recommendation data as validated by one or more of the plurality of supervising users; and updating a second reinforcement learning signal based on the results of the activity programs; and applying both the first reinforcement learning signal and the second reinforcement learning signal to the one or more machine learning models.

In Example 4, the subject matter of Example 3 includes, wherein the first reinforcement learning signal and the second reinforcement learning signal are derived from paired data comprising a supervising user-approved recommendation and a corresponding measured outcome in relation to a particular activity program.

In Example 5, the subject matter of Examples 3-4 includes, wherein generating the further recommendation data comprises, based on the automated reinforcement learning, automatically detecting and applying successful patterns for different user cohorts across the plurality of tracked users.

In Example 6, the subject matter of Examples 1-5 includes, wherein the modifying of the parameters of the one or more machine learning models is performed during a second stage using updated training data based on the validated activity program data of the plurality of tracked users and the results of the plurality of tracked users, the operations further comprising, in a first stage prior to the second stage: training the one or more machine learning models using base training data.

In Example 7, the subject matter of Examples 1-6 includes, wherein the one or more machine learning models has a transformer architecture, and the operations further comprise controlling generation of the automatically generated exploratory program elements at least in part by adjusting a temperature parameter of the one or more machine learning models.

In Example 8, the subject matter of Examples 1-7 includes, wherein the one or more automatically generated exploratory program elements comprise at least one of: a new activity not contained in the user data, an activity variation not contained in the user data, or a new activity sequence not contained in the user data.

In Example 9, the subject matter of Example 8 includes, wherein the one or more automatically generated exploratory program elements comprise the new activity sequence, and the recommendation data indicates a recommended change in an order of activities to be performed by a particular tracked user of the plurality of tracked users.

In Example 10, the subject matter of Examples 1-9 includes, the operations further comprising: transmitting the recommendation data to a user device of the supervising user; and receiving the user input from the user device of the supervising user, the user input indicating approval of the one or more automatically generated exploratory program elements in the recommendation data, wherein the validated activity program data is automatically generated to include the one or more automatically generated exploratory program elements in response to receiving the user input.

In Example 11, the subject matter of Examples 1-10 includes, the operations comprising: transmitting the recommendation data to a user device of the supervising user; and receiving the user input from the user device of the supervising user, the user input indicating an update to the one or more automatically generated exploratory program elements in the recommendation data, wherein the validated activity program data is generated by applying the update to the one or more automatically generated exploratory program elements in response to receiving the user input.

In Example 12, the subject matter of Examples 1-11 includes, wherein the user tracking data comprises at least one of: real-time tracking data from one or more activity sessions, performance data, biomechanical data, physiological data, behavioral data, or environmental data, and wherein the user interaction data comprises at least one of: clinical data, baseline assessment data, enrollment data, demographic data, activity session data, progress evaluation data, communication history data, user feedback data, or supervising user feedback data.

In Example 13, the subject matter of Examples 1-12 includes, wherein the one or more sensors comprise one or more image sensors and the one or more automatically generated exploratory program elements comprise one or more new exercises, the operations further comprising, for each tracked user of the plurality of tracked users: capturing, by the one or more image sensors, images of the tracked user while the tracked user performs the one or more new exercises; processing the images to generate real-time tracking data; updating the user tracking data based on the real-time tracking data; and generating, by the one or more machine learning models, the further recommendation data based at least partially on the updated user tracking data.

In Example 14, the subject matter of Example 13 includes, the operations further comprising: displaying a user interface comprising a digital video feed representing the images together with at least one of activity tracking output or instructions for performing the one or more new exercises.

In Example 15, the subject matter of Examples 1-14 includes, wherein the hardware device comprises at least one of: a tablet computing device, a mobile phone, a wearable device, or an intra-body device.

In Example 16, the subject matter of Examples 1-15 includes, wherein the one or more sensors comprise one or more tracking sensors and one or more environmental sensors.

In Example 17, the subject matter of Examples 1-16 includes, wherein the one or more machine learning models comprise one or more recommender machine learning models, the operations further comprising: executing one or more session analyzer AI agents to process the user tracking data associated with one or more activity sessions of the activity program; and executing one or more behavioral analyzer AI agents to process behavioral data associated with user behavior outside of the one or more activity sessions, wherein the one or more recommender machine learning models process outputs of the one or more session analyzer AI agents and the one or more behavioral analyzer AI agents to generate the recommendation data.

In Example 18, the subject matter of Examples 1-17 includes, the operations further comprising: executing one or more user engagement AI agents to generate personalized interactions with the plurality of tracked users; receiving, from a particular tracked user of the plurality of tracked users, feedback in response to a personalized interaction generated by the one or more user engagement AI agents;

and in response to receiving the feedback, automatically updating the activity program of the particular tracked user.

Example 19 is a computer-implemented method comprising: for each tracked user of a plurality of tracked users: maintaining, in at least one database, user data comprising at least one of user tracking data or user interaction data related to an activity program of the tracked user, the tracking data based at least partially on sensor data from one or more sensors of a hardware device associated with the tracked user; processing, by one or more machine learning models, the user data to obtain recommendation data comprising one or more automatically generated exploratory program elements of the activity program of the tracked user, generating validated activity program data based on user input, received from a supervising user, in response to the recommendation data, and updating, in the at least one database, the user data to record results of the activity program performed according to the validated activity program data; automatically modifying parameters of the one or more machine learning models based on both the validated activity program data of the plurality of tracked users and the results of the plurality of tracked users; and after modifying the parameters of the one or more machine learning models, generating further recommendation data for at least one of the plurality of tracked users.

Example 20 is one or more non-transitory machine-readable storage media including instructions that, when executed by one or more hardware processors, cause the one or more hardware processors to perform operations comprising: for each tracked user of a plurality of tracked users: maintaining, in at least one database, user data comprising at least one of user tracking data or user interaction data related to an activity program of the tracked user, the tracking data based at least partially on sensor data from one or more sensors of a hardware device associated with the tracked user; processing, by one or more machine learning models, the user data to obtain recommendation data comprising one or more automatically generated exploratory program elements of the activity program of the tracked user, generating validated activity program data based on user input, received from a supervising user, in response to the recommendation data, and updating, in the at least one database, the user data to record results of the activity program performed according to the validated activity program data; automatically modifying parameters of the one or more machine learning models based on both the validated activity program data of the plurality of tracked users and the results of the plurality of tracked users; and after modifying the parameters of the one or more machine learning models, generating further recommendation data for at least one of the plurality of tracked users.

Example 21 is at least one machine-readable medium including instructions that, when executed by processing circuitry, cause the processing circuitry to perform operations to implement any of Examples 1-20.

Example 22 is an apparatus comprising means to implement any of Examples 1-20.

Example 23 is a system to implement any of Examples 1-20.

Example 24 is a method to implement any of Examples 1-20.

What is claimed is:

1. A system comprising:

a plurality of hardware devices associated with a plurality of tracked users of the system; and one or more hardware processors; and memory storing instructions that, when executed by the one or more hardware processors, cause the one or more hardware processors to perform operations comprising:

for each tracked user of the plurality of tracked users:

maintaining, in at least one database, user data comprising at least one of user tracking data or user interaction data related to an activity program of the tracked user, the user tracking data based at least partially on sensor data from one or more sensors of a hardware device from among the plurality of hardware devices that is associated with the tracked user;

processing, by one or more generative machine learning models, the user data to obtain recommendation data comprising one or more automatically generated exploratory program elements of the activity program of the tracked user, the recommendation data being generated by the one or more generative machine learning models based on one or more prompts comprising the user data;

generating validated activity program data based on user input, received from a user device of a supervising user from among a plurality of supervising users of the system, in response to the recommendation data, the user input comprising at least one of an approval of the recommendation data or an update associated with the recommendation data; and updating, in the at least one database, the user data to record results of the activity program performed according to the validated activity program data;

automatically modifying parameters of the one or more generative machine learning models by training the one or more generative machine learning models based on both the validated activity program data of the plurality of tracked users and the results of the plurality of tracked users; and after modifying the parameters of the one or more generative machine learning models, generating further recommendation data for at least one of the plurality of tracked users, the further recommendation data being generated by the one or more generative machine learning models based on one or more further prompts comprising further user data.

2. The system of claim 1, wherein the training of the one or more generative machine learning models comprises performing at least one of supervised fine-tuning, reinforcement fine-tuning, or reinforcement learning with human feedback.

3. The system of claim 1, wherein the training of the one or more generative machine learning models comprises performing automated reinforcement learning by:

updating a first reinforcement learning signal based on the recommendation data as validated by one or more of the plurality of supervising users;

updating a second reinforcement learning signal based on the results of the activity programs; and training the one or more generative machine learning models by applying both the first reinforcement learning signal and the second reinforcement learning signal to the one or more generative machine learning models.

4. The system of claim 3, wherein the first reinforcement learning signal and the second reinforcement learning signal are derived from paired data comprising a supervising user-approved recommendation and a corresponding measured outcome in relation to a particular activity program.

5. The system of claim 3, wherein generating the further recommendation data comprises, based on the automated reinforcement learning, automatically detecting and applying successful patterns for different user cohorts across the plurality of tracked users.

6. The system of claim 1, wherein the training of the one or more generative machine learning models is performed during a second stage using updated training data based on the validated activity program data of the plurality of tracked users and the results of the plurality of tracked users, the operations further comprising, in a first stage prior to the second stage:

training the one or more generative machine learning models using base training data.

7. The system of claim 1, wherein at least one of the one or more generative machine learning models has a transformer architecture, and the operations further comprise controlling generation of the one or more automatically generated exploratory program elements at least in part by adjusting a temperature parameter of the one or more generative machine learning models.

8. The system of claim 1, wherein the one or more automatically generated exploratory program elements comprise at least one of: a new activity not contained in the user data, an activity variation not contained in the user data, or a new activity sequence not contained in the user data.

9. The system of claim 8, wherein the one or more automatically generated exploratory program elements comprise the new activity sequence, and the recommendation data indicates a recommended change in an order of activities to be performed by a particular tracked user of the plurality of tracked users.

10. The system of claim 1, the operations further comprising:

transmitting the recommendation data to the user device of the supervising user; and receiving the user input from the user device of the supervising user, the user input indicating approval of the one or more automatically generated exploratory program elements in the recommendation data, wherein the validated activity program data is automatically generated to include the one or more automatically generated exploratory program elements in response to receiving the user input.

11. The system of claim 1, the operations comprising:

transmitting the recommendation data to the user device of the supervising user; and receiving the user input from the user device of the supervising user, the user input indicating an update to the one or more automatically generated exploratory program elements in the recommendation data, wherein the validated activity program data is generated by applying the update to the one or more automatically generated exploratory program elements in response to receiving the user input.

12. The system of claim 1, wherein the user tracking data comprises at least one of: real-time tracking data from one or more activity sessions, performance data, biomechanical data, physiological data, behavioral data, or environmental data, and wherein the user interaction data comprises at least one of: clinical data, baseline assessment data, enrollment data, demographic data, activity session data, progress evaluation data, communication history data, user feedback data, or supervising user feedback data.

13. The system of claim 1, wherein the one or more sensors comprise one or more image sensors and the one or more automatically generated exploratory program elements comprise one or more new exercises, the operations further comprising, for each tracked user of the plurality of tracked users:

capturing, by the one or more image sensors, images of the tracked user while the tracked user performs the one or more new exercises;

processing the images to generate real-time tracking data;

updating the user tracking data based on the real-time tracking data; and generating, by the one or more generative machine learning models, the further recommendation data based at least partially on the updated user tracking data.

14. The system of claim 13, the operations further comprising:

displaying a user interface comprising a digital video feed representing the images together with at least one of activity tracking output or instructions for performing the one or more new exercises.

15. The system of claim 1, wherein the hardware device comprises at least one of: a tablet computing device, a mobile phone, a wearable device, or an intra-body device.

16. The system of claim 1, wherein the one or more sensors comprise one or more tracking sensors and one or more environmental sensors.

17. The system of claim 1, wherein the one or more generative machine learning models comprise one or more recommender machine learning models, the operations further comprising:

executing one or more session analyzer artificial intelligence (AI) agents to process the user tracking data associated with one or more activity sessions of the activity program; and executing one or more behavioral analyzer AI agents to process behavioral data associated with user behavior outside of the one or more activity sessions, wherein the one or more recommender machine learning models process outputs of the one or more session analyzer AI agents and the one or more behavioral analyzer AI agents to generate the recommendation data.

18. The system of claim 1, the operations further comprising:

executing one or more user engagement AI agents to generate personalized interactions with the plurality of tracked users;

receiving, from a particular tracked user of the plurality of tracked users, feedback in response to a personalized interaction generated by the one or more user engagement AI agents; and in response to receiving the feedback, automatically updating the activity program of the particular tracked user.

19. A computer-implemented method comprising:

for each tracked user of a plurality of tracked users:

maintaining, in at least one database, user data comprising at least one of user tracking data or user interaction data related to an activity program of the tracked user, the user tracking data based at least partially on sensor data from one or more sensors of a hardware device associated with the tracked user;

processing, by one or more generative machine learning models, the user data to obtain recommendation data comprising one or more automatically generated exploratory program elements of the activity program of the tracked user, the recommendation data being generated by the one or more generative machine learning models based on one or more prompts comprising the user data;

generating validated activity program data based on user input, received from a user device of a supervising user, in response to the recommendation data, the user input comprising at least one of an approval of the recommendation data or an update associated with the recommendation data; and updating, in the at least one database, the user data to record results of the activity program performed according to the validated activity program data;

automatically modifying parameters of the one or more generative machine learning models by training the one or more generative machine learning models based on both the validated activity program data of the plurality of tracked users and the results of the plurality of tracked users; and after modifying the parameters of the one or more generative machine learning models, generating further recommendation data for at least one of the plurality of tracked users, the further recommendation data being generated by the one or more generative machine learning models based on one or more further prompts comprising further user data.

20. One or more non-transitory machine-readable storage media including instructions that, when executed by one or more hardware processors, cause the one or more hardware processors to perform operations comprising:

for each tracked user of a plurality of tracked users:

maintaining, in at least one database, user data comprising at least one of user tracking data or user interaction data related to an activity program of the tracked user, the user tracking data based at least partially on sensor data from one or more sensors of a hardware device associated with the tracked user;

processing, by one or more generative machine learning models, the user data to obtain recommendation data comprising one or more automatically generated exploratory program elements of the activity program of the tracked user, the recommendation data being generated by the one or more generative machine learning models based on one or more prompts comprising the user data;

generating validated activity program data based on user input, received from a user device of a supervising user, in response to the recommendation data, the user input comprising at least one of an approval of the recommendation data or an update associated with the recommendation data; and updating, in the at least one database, the user data to record results of the activity program performed according to the validated activity program data;

automatically modifying parameters of the one or more generative machine learning models by training the one or more generative machine learning models based on both the validated activity program data of the plurality of tracked users and the results of the plurality of tracked users; and after modifying the parameters of the one or more generative machine learning models, generating further recommendation data for at least one of the plurality of tracked users, the further recommendation data being generated by the one or more generative machine learning models based on one or more further prompts comprising further user data.

* * * * *